United States Patent
Fang et al.

(10) Patent No.: US 10,208,119 B2
(45) Date of Patent: Feb. 19, 2019

(54) ANTI-PD-L1 ANTIBODIES AND USES THEREOF

(71) Applicant: I-MAB, Grand Cayman (KY)

(72) Inventors: Lei Fang, Shanghai (CN); Zhengyi Wang, Shanghai (CN); Bingshi Guo, Shanghai (CN); Jingwu Zang, Shanghai (CN)

(73) Assignee: I-MAB, Grand Cayman (KY)

( * ) Notice: Subject to any disclaimer, the term of this patent is extended or adjusted under 35 U.S.C. 154(b) by 0 days.

(21) Appl. No.: 16/100,019

(22) Filed: Aug. 9, 2018

(65) Prior Publication Data

US 2018/0346573 A1   Dec. 6, 2018

Related U.S. Application Data

(62) Division of application No. 15/744,737, filed as application No. PCT/CN2017/088033 on Jun. 13, 2017, now Pat. No. 10,059,769.

(30) Foreign Application Priority Data

Jun. 13, 2016 (CN) .......................... 2016 1 0414226
Jan. 25, 2017 (WO) ................ PCT/CN2017/072566

(51) Int. Cl.
| | |
|---|---|
| C07K 16/28 | (2006.01) |
| A61K 39/395 | (2006.01) |
| A61P 31/04 | (2006.01) |
| A61P 31/06 | (2006.01) |
| A61P 31/08 | (2006.01) |
| A61P 31/14 | (2006.01) |
| A61P 31/16 | (2006.01) |
| A61P 31/18 | (2006.01) |
| A61P 31/20 | (2006.01) |
| A61P 31/22 | (2006.01) |
| A61P 35/00 | (2006.01) |
| A61P 35/02 | (2006.01) |
| A61K 35/17 | (2015.01) |
| A61K 39/00 | (2006.01) |

(52) U.S. Cl.
CPC .......... *C07K 16/2827* (2013.01); *A61K 35/17* (2013.01); *A61P 31/04* (2018.01); *A61P 31/06* (2018.01); *A61P 31/08* (2018.01); *A61P 31/14* (2018.01); *A61P 31/16* (2018.01); *A61P 31/18* (2018.01); *A61P 31/20* (2018.01); *A61P 31/22* (2018.01); *A61P 35/00* (2018.01); *A61P 35/02* (2018.01); *A61K 2039/505* (2013.01); *A61K 2039/5158* (2013.01); *A61K 2039/575* (2013.01); *C07K 2317/21* (2013.01); *C07K 2317/24* (2013.01); *C07K 2317/32* (2013.01); *C07K 2317/33* (2013.01); *C07K 2317/52* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS 10,059,769 B2 * 8/2018 Fang ...................... A61K 35/17

FOREIGN PATENT DOCUMENTS

| WO | WO 2007/005874 | 1/2007 |
|---|---|---|
| WO | WO 2016/024228 | 2/2016 |

OTHER PUBLICATIONS

International Search Report and Written Opinion of PCT/CN2017/088033 dated Sep. 13, 2017 (12 pages).
Boyerinas, B. et al., "Antibody-Dependent Cellular Cytotoxicity Activity of a Novel Anti-PD-L1 Antibody Avelumab (MSB0010718C) on Human Tumor Cells." Cancer Immunology Research, vol. 3, No. 10, May 26, 2015. pp. 1148-1157.
Ishida et al., "Differential expression of PD-L1 and PD-L2, ligands for an inhibitory receptor PD-1, in the cells of lymphohematopoietic tissues," Immunol Lett. 2002; 84: pp. 57-62.
Li, B et al., "Cloning, prokaryotic expression of human PD-L1 and preparation of its antibody." Med J Chin PLA, vol. 35, No. 8, Aug. 1, 2010 , pp. 997-999 (English Abstract).
Taube et al., Colocalization of inflammatory response with B7-h1 expression in human melanocytic lesions supports an adaptive resistance mechanism of immune escape. Sci Transl Med. 2012:4(127): 127ra37; p. 1-22.
Zhou, Y. "Preparation and characterization of three novel monoclonal antibodies against human PD-L1." Chinese Master's Theses Full-text Database Medicine and Health Sciences., Jun. 15, 2012 (English Abstract).

* cited by examiner

*Primary Examiner* — Ilia I Ouspenski
(74) *Attorney, Agent, or Firm* — Sheppard Mullin Richter & Hampton LLP

(57) ABSTRACT

Provided are anti-PD-L1 antibodies or fragments thereof. The antibodies or fragments thereof specifically bind to the immunoglobulin C domain of the PD-L1 protein. In various example, the antibodies or fragments thereof include a VH CDR1 of SEQ ID NO: 1, a VH CDR2 of SEQ ID NO: 2, a VH CDR3 of SEQ ID NO: 3, a VL CDR1 of SEQ ID NO: 4, a VL CDR2 of SEQ ID NO: 5, and a VL CDR3 of SEQ ID NO: 6, or variants of each thereof. Methods of using the antibodies or fragments thereof for treating and diagnosing diseases such as cancer and infectious diseases are also provided.

18 Claims, 17 Drawing Sheets
Specification includes a Sequence Listing.

SEQUENCE LISTING

<160> NUMBER OF SEQ ID NOS: 115

<210> SEQ ID NO 1
<211> LENGTH: 5
<212> TYPE: PRT
<213> ORGANISM: Artificial Sequence
<220> FEATURE:
<223> OTHER INFORMATION: Synthetic

<400> SEQUENCE: 1

Ser Tyr Asp Met Ser
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic

```
<400> SEQUENCE: 2

Thr Ile Ser Asp Gly Gly Gly Tyr Ile Tyr Tyr Ser Asp Ser Val Lys
1               5                   10                  15

Gly

<210> SEQ ID NO 3
<211> LENGTH: 10
<212> TYPE: PRT
<213> ORGANISM: Artificial Sequence
<220> FEATURE:
<223> OTHER INFORMATION: Synthetic

<400> SEQUENCE: 3

Glu Phe Gly Lys Arg Tyr Ala Leu Asp Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic

<400> SEQUENCE: 4

Lys Ala Ser Gln Asp Val Thr Pro Ala Val Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

Ser Thr Ser Ser Arg Tyr Thr
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

Gln Gln His Tyr Thr Thr Pro Leu Thr
1               5

<210> SEQ ID NO 7
<211> LENGTH: 119
<212> TYPE: PRT
<213> ORGANISM: Artificial Sequence
<220> FEATURE:
<223> OTHER INFORMATION: Synthetic

<400> SEQUENCE: 7

Glu Val Lys Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
                20                  25                  30

Asp Met Ser Trp Val Arg Gln Thr Pro Glu Lys Ser Leu Glu Trp Val
            35                  40                  45
```

Ala Thr Ile Ser Asp Gly Gly Gly Tyr Ile Tyr Tyr Ser Asp Ser Val
        50                  55                  60

Lys Gly Arg Phe Thr Ile Ser Arg Asp Asn Ala Lys Asn Asn Leu Tyr
 65                  70                  75                  80

Leu Gln Met Ser Ser Leu Arg Ser Glu Asp Thr Ala Leu Tyr Ile Cys
                85                  90                  95

Ala Arg Glu Phe Gly Lys Arg Tyr Ala Leu Asp Tyr Trp Gly Gln Gly
                    100                 105                 110

Thr Ser Val Thr Val Ser Ser
            115

<210> SEQ ID NO 8
<211> LENGTH: 119
<212> TYPE: PRT
<213> ORGANISM: Artificial Sequence
<220> FEATURE:
<223> OTHER INFORMATION: Synthetic'

<400> SEQUENCE: 8

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Ser Tyr
                 20                  25                  30

Asp Met Ser Trp Val Arg Gln Ala Pro Gly Lys Gly Leu Glu Trp Val
             35                  40                  45

Ser Thr Ile Ser Asp Gly Gly Gly Tyr Ile Tyr Tyr Ser Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Glu Phe Gly Lys Arg Tyr Ala Leu Asp Tyr Trp Gly Gln Gly
                    100                 105                 110

Thr Thr Val Thr Val Ser Ser
            115

<210> SEQ ID NO 9
<211> LENGTH: 119
<212> TYPE: PRT
<213> ORGANISM: Artificial Sequence
<220> FEATURE:
<223> OTHER INFORMATION: Synthetic

<400> SEQUENCE: 9

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Ser Tyr
                 20                  25                  30

Asp Met Ser Trp Val Arg Gln Ala Pro Gly Lys Gly Leu Glu Trp Val
             35                  40                  45

Ala Thr Ile Ser Asp Gly Gly Gly Tyr Ile Tyr Tyr Ser Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Glu Phe Gly Lys Arg Tyr Ala Leu Asp Tyr Trp Gly Gln Gly
                    100                 105                 110

```
Thr Thr Val Thr Val Ser Ser
        115

<210> SEQ ID NO 10
<211> LENGTH: 119
<212> TYPE: PRT
<213> ORGANISM: Artificial Sequence
<220> FEATURE:
<223> OTHER INFORMATION: Synthetic

<400> SEQUENCE: 10

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Gly Gly Tyr Ile Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Ile Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser
        115

<210> SEQ ID NO 11
<211> LENGTH: 119
<212> TYPE: PRT
<213> ORGANISM: Artificial Sequence
<220> FEATURE:
<223> OTHER INFORMATION: Synthetic

<400> SEQUENCE: 11

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Ile Arg Gln Ala Pro Gly Lys Gly Leu Glu Trp Val
        35                  40                  45

Ser Thr Ile Ser Asp Gly Gly Tyr Ile Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser
        115

<210> SEQ ID NO 12
<211> LENGTH: 119
<212> TYPE: PRT
<213> ORGANISM: Artificial Sequence
<220> FEATURE:
<223> OTHER INFORMATION: Synthetic
```

<400> SEQUENCE: 12

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Ile Arg Gln Ala Pro Gly Lys Gly Leu Glu Trp Val
        35                  40                  45

Ala Thr Ile Ser Asp Gly Gly Tyr Ile Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser
            115

<210> SEQ ID NO 13
<211> LENGTH: 119
<212> TYPE: PRT
<213> ORGANISM: Artificial Sequence
<220> FEATURE:
<223> OTHER INFORMATION: Synthetic

<400> SEQUENCE: 13

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Gly Gly Tyr Ile Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Ile Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser
            115

<210> SEQ ID NO 14
<211> LENGTH: 119
<212> TYPE: PRT
<213> ORGANISM: Artificial Sequence
<220> FEATURE:
<223> OTHER INFORMATION: Synthetic

<400> SEQUENCE: 14

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Thr Ile Ser Asp Gly Gly Gly Tyr Ile Tyr Tyr Ser Asp Ser Val
       50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Phe Gly Lys Arg Tyr Ala Leu Asp Tyr Trp Gly Gln Gly
                100                 105                 110

Thr Thr Val Thr Val Ser Ser
        115

<210> SEQ ID NO 15
<211> LENGTH: 119
<212> TYPE: PRT
<213> ORGANISM: Artificial Sequence
<220> FEATURE:
<223> OTHER INFORMATION: Synthetic

<400> SEQUENCE: 15

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
                20                  25                  30

Asp Met Ser Trp Val Arg Gln Ala Pro Gly Lys Ser Leu Glu Trp Val
             35                  40                  45

Ala Thr Ile Ser Asp Gly Gly Gly Tyr Ile Tyr Tyr Ser Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Ile Cys
                 85                  90                  95

Ala Arg Glu Phe Gly Lys Arg Tyr Ala Leu Asp Tyr Trp Gly Gln Gly
                100                 105                 110

Thr Thr Val Thr Val Ser Ser
        115

<210> SEQ ID NO 16
<211> LENGTH: 119
<212> TYPE: PRT
<213> ORGANISM: Artificial Sequence
<220> FEATURE:
<223> OTHER INFORMATION: Synthetic

<400> SEQUENCE: 16

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
                20                  25                  30

Asp Met Ser Trp Val Arg Gln Ala Pro Gly Lys Gly Leu Glu Trp Val
             35                  40                  45

Ser Thr Ile Ser Asp Gly Gly Gly Tyr Ile Tyr Tyr Ser Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                 85                  90                  95

Ala Arg Glu Phe Gly Lys Arg Tyr Ala Leu Asp Tyr Trp Gly Gln Gly

Thr Thr Val Thr Val Ser Ser
        115

<210> SEQ ID NO 17
<211> LENGTH: 119
<212> TYPE: PRT
<213> ORGANISM: Artificial Sequence
<220> FEATURE:
<223> OTHER INFORMATION: Synthetic

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ala Thr Ile Ser Asp Gly Gly Tyr Ile Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser
        115

<210> SEQ ID NO 18
<211> LENGTH: 119
<212> TYPE: PRT
<213> ORGANISM: Artificial Sequence
<220> FEATURE:
<223> OTHER INFORMATION: Synthetic

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Gly Gly Tyr Ile Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser
        115

<210> SEQ ID NO 19
<211> LENGTH: 119
<212> TYPE: PRT
<213> ORGANISM: Artificial Sequence
<220> FEATURE:

<223> OTHER INFORMATION: Synthetic

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Glu Gly Gly Tyr Ile Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser
        115

<210> SEQ ID NO 20
<211> LENGTH: 119
<212> TYPE: PRT
<213> ORGANISM: Artificial Sequence
<220> FEATURE:
<223> OTHER INFORMATION: Synthetic

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Ala Gly Gly Tyr Ile Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser
        115

<210> SEQ ID NO 21
<211> LENGTH: 119
<212> TYPE: PRT
<213> ORGANISM: Artificial Sequence
<220> FEATURE:
<223> OTHER INFORMATION: Synthetic

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val

```
                 35                  40                  45
Ala Thr Ile Ser Asp Val Gly Gly Tyr Ile Tyr Tyr Ser Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Ile Cys
                 85                  90                  95

Ala Arg Glu Phe Gly Lys Arg Tyr Ala Leu Asp Tyr Trp Gly Gln Gly
                100                 105                 110

Thr Thr Val Thr Val Ser Ser
        115

<210> SEQ ID NO 22
<211> LENGTH: 119
<212> TYPE: PRT
<213> ORGANISM: Artificial Sequence
<220> FEATURE:
<223> OTHER INFORMATION: Synthetic

<400> SEQUENCE: 22

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Asp Met Ser Trp Val Arg Gln Ala Pro Gly Lys Gly Leu Glu Trp Val
                 35                  40                  45

Ala Thr Ile Ser Asp Gly Gly Gly Tyr Ile Tyr Tyr Ser Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Phe Gly Lys Arg Tyr Ala Leu Asp Tyr Trp Gly Gln Gly
                100                 105                 110

Thr Leu Val Thr Val Ser Ser
        115

<210> SEQ ID NO 23
<211> LENGTH: 119
<212> TYPE: PRT
<213> ORGANISM: Artificial Sequence
<220> FEATURE:
<223> OTHER INFORMATION: Synthetic

<400> SEQUENCE: 23

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Asp Met Ser Trp Val Arg Gln Ala Pro Gly Lys Gly Leu Glu Trp Val
                 35                  40                  45

Ala Thr Ile Ser Asp Gly Gly Gly Tyr Ile Tyr Tyr Ser Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Ile Cys
                 85                  90                  95
```

```
Ala Arg Glu Phe Gly Lys Arg Tyr Ala Leu Asp Tyr Trp Gly Gln Gly
            100                 105                 110

Thr Leu Val Thr Val Ser Ser
        115

<210> SEQ ID NO 24
<211> LENGTH: 119
<212> TYPE: PRT
<213> ORGANISM: Artificial Sequence
<220> FEATURE:
<223> OTHER INFORMATION: Synthetic

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ala Thr Ile Ser Asp Gly Gly Gly Tyr Ile Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Ile Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser
        115

<210> SEQ ID NO 25
<211> LENGTH: 119
<212> TYPE: PRT
<213> ORGANISM: Artificial Sequence
<220> FEATURE:
<223> OTHER INFORMATION: Synthetic

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ala Thr Ile Ser Asp Gly Gly Gly Tyr Ile Tyr Tyr Ser Asp Ser Val
    50                  55                  60

Lys Gly Arg Phe Thr Ile Ser Arg Asp Asn Ala Lys Asn Asn Leu Tyr
65                  70                  75                  80

Leu Gln Met Asn Ser Leu Arg Ala Glu Asp Thr Ala Val Tyr Ile Cys
                85                  90                  95

Ala Arg Glu Phe Gly Lys Arg Tyr Ala Leu Asp Tyr Trp Gly Gln Gly
            100                 105                 110

Thr Leu Val Thr Val Ser Ser
        115

<210> SEQ ID NO 26
<211> LENGTH: 119
<212> TYPE: PRT
<213> ORGANISM: Artificial Sequence
```

<220> FEATURE:
<223> OTHER INFORMATION: Synthetic

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Thr Pro Glu Lys Ser Leu Glu Trp Val
        35                  40                  45

Ala Thr Ile Ser Asp Gly Gly Tyr Ile Tyr Tyr Ser Asp Ser Val
    50                  55                  60

Lys Gly Arg Phe Thr Ile Ser Arg Asp Asn Ala Lys Asn Asn Leu Tyr
65                  70                  75                  80

Leu Gln Met Asn Ser Leu Arg Ala Glu Asp Thr Ala Val Tyr Ile Cys
                85                  90                  95

Ala Arg Glu Phe Gly Lys Arg Tyr Ala Leu Asp Tyr Trp Gly Gln Gly
            100                 105                 110

Thr Leu Val Thr Val Ser Ser
        115

<210> SEQ ID NO 27
<211> LENGTH: 107
<212> TYPE: PRT
<213> ORGANISM: Artificial Sequence
<220> FEATURE:
<223> OTHER INFORMATION: Synthetic

<400> SEQUENCE: 27

Asp Ile Val Met Thr Gln Ser His Lys Phe Met Ser Thr Ser Val Gly
1               5                   10                  15

Asp Arg Val Ser Ile Ser Cys Lys Ala Ser Gln Asp Val Thr Pro Ala
            20                  25                  30

Val Ala Trp Tyr Gln Gln Lys Pro Gly Gln Ser Pro Lys Leu Leu Ile
        35                  40                  45

Tyr Ser Thr Ser Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Thr Thr Pro Leu
                85                  90                  95

Thr Phe Gly Ala Gly Thr Lys Leu Glu Leu Lys
            100                 105

<210> SEQ ID NO 28
<211> LENGTH: 107
<212> TYPE: PRT
<213> ORGANISM: Artificial Sequence
<220> FEATURE:
<223> OTHER INFORMATION: Synthetic

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Gln Lys Pro Gly Lys Ala Pro Lys Leu Leu Ile
        35                  40                  45

```
Tyr Ser Thr Ser Ser Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Thr Thr Pro Leu
                85                  90                  95

Thr Phe Gly Gln Gly Thr Lys Leu Glu Ile Lys
                100                 105

<210> SEQ ID NO 29
<211> LENGTH: 107
<212> TYPE: PRT
<213> ORGANISM: Artificial Sequence
<220> FEATURE:
<223> OTHER INFORMATION: Synthetic

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
                20                  25                  30

Val Ala Trp Tyr Gln Gln Lys Pro Gly Lys Ser Pro Lys Leu Leu Ile
            35                  40                  45

Tyr Ser Thr Ser Ser Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Thr Thr Pro Leu
                85                  90                  95

Thr Phe Gly Gln Gly Thr Lys Leu Glu Ile Lys
                100                 105

<210> SEQ ID NO 30
<211> LENGTH: 108
<212> TYPE: PRT
<213> ORGANISM: Artificial Sequence
<220> FEATURE:
<223> OTHER INFORMATION: Synthetic

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
                20                  25                  30

Val Ala Trp Tyr Gln Gln Lys Pro Gly Lys Ala Pro Lys Leu Leu Ile
            35                  40                  45

Tyr Ser Thr Ser Ser Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Leu
                85                  90                  95

Thr Phe Gly Gln Gly Thr Lys Leu Glu Ile Lys Arg
                100                 105

<210> SEQ ID NO 31
<211> LENGTH: 108
<212> TYPE: PRT
<213> ORGANISM: Artificial Sequence
```

<220> FEATURE:
<223> OTHER INFORMATION: Synthetic

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Gln Lys Pro Gly Lys Ala Pro Lys Leu Leu Ile
        35                  40                  45

Tyr Ser Thr Ser Ser Arg Tyr Thr Gly Val Pro Asp Arg Phe Thr Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Leu
                85                  90                  95

Thr Phe Gly Gln Gly Thr Lys Leu Glu Ile Lys Arg
            100                 105

<210> SEQ ID NO 32
<211> LENGTH: 108
<212> TYPE: PRT
<213> ORGANISM: Artificial Sequence
<220> FEATURE:
<223> OTHER INFORMATION: Synthetic

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Gln Lys Pro Gly Gln Ser Pro Lys Leu Leu Ile
        35                  40                  45

Tyr Ser Thr Ser Ser Arg Tyr Thr Gly Val Pro Asp Arg Phe Thr Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Leu
                85                  90                  95

Thr Phe Gly Gln Gly Thr Lys Leu Glu Ile Lys Arg
            100                 105

<210> SEQ ID NO 33
<211> LENGTH: 108
<212> TYPE: PRT
<213> ORGANISM: Artificial Sequence
<220> FEATURE:
<223> OTHER INFORMATION: Synthetic

<400> SEQUENCE: 33

Asp Ile Gln Met Thr Gln Ser Pro Ser Ser Leu Ser Ala Ser Val Gly
1               5                   10                  15

Asp Arg Val Thr Ile Ser Cys Lys Ala Ser Gln Asp Val Thr Pro Ala
            20                  25                  30

Val Ala Trp Tyr Gln Gln Lys Pro Gly Gln Ser Pro Lys Leu Leu Ile
        35                  40                  45

Tyr Ser Thr Ser Ser Arg Tyr Thr Gly Val Pro Asp Arg Phe Thr Gly
    50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Leu
                 85                  90                  95

Thr Phe Gly Gln Gly Thr Lys Leu Glu Ile Lys Arg
            100                 105

<210> SEQ ID NO 34
<211> LENGTH: 356
<212> TYPE: PRT
<213> ORGANISM: Artificial Sequence
<220> FEATURE:
<223> OTHER INFORMATION: Synthetic

<400> SEQUENCE: 34

Ala Gly Gly Thr Gly Ala Ala Gly Cys Thr Gly Gly Thr Gly Gly Ala
 1               5                  10                  15

Gly Ala Gly Cys Gly Gly Cys Gly Gly Ala Gly Ala Thr Cys Thr Gly
                20                  25                  30

Gly Thr Gly Ala Ala Gly Cys Cys Thr Gly Gly Cys Gly Gly Cys Ala
             35                  40                  45

Gly Cys Cys Thr Gly Ala Ala Gly Cys Thr Gly Ala Gly Cys Thr Gly
         50                  55                  60

Thr Gly Cys Cys Gly Cys Cys Ala Gly Cys Gly Cys Thr Thr Cys
 65                  70                  75                  80

Ala Cys Cys Thr Thr Cys Ala Gly Cys Ala Gly Cys Thr Ala Cys Gly
                 85                  90                  95

Ala Cys Ala Thr Gly Ala Gly Cys Thr Gly Gly Thr Gly Ala Gly Gly
                100                 105                 110

Gly Cys Ala Gly Ala Cys Cys Cys Cys Gly Ala Gly Ala Ala Gly
            115                 120                 125

Ala Gly Cys Cys Thr Gly Gly Ala Gly Thr Gly Gly Gly Thr Gly Gly
            130                 135                 140

Cys Cys Ala Cys Cys Ala Thr Cys Ala Gly Cys Gly Ala Thr Gly Gly
145                 150                 155                 160

Cys Gly Gly Cys Gly Gly Cys Thr Ala Cys Ala Thr Cys Thr Ala Cys
                165                 170                 175

Thr Ala Cys Ala Gly Cys Gly Ala Cys Ala Gly Cys Gly Thr Gly Ala
            180                 185                 190

Ala Gly Gly Gly Cys Ala Gly Gly Thr Thr Cys Ala Cys Cys Ala Thr
            195                 200                 205

Cys Ala Gly Cys Ala Gly Gly Ala Cys Ala Cys Gly Cys Cys
        210                 215                 220

Ala Ala Gly Ala Ala Cys Ala Cys Cys Thr Gly Thr Ala Cys Cys
225                 230                 235                 240

Thr Gly Cys Ala Gly Ala Thr Gly Ala Gly Cys Ala Gly Cys Cys Thr
                245                 250                 255

Gly Ala Gly Gly Ala Gly Cys Gly Gly Ala Cys Ala Cys Cys
            260                 265                 270

Gly Cys Cys Cys Thr Gly Thr Ala Cys Ala Thr Cys Thr Gly Cys Gly
        275                 280                 285

Cys Cys Ala Gly Gly Gly Ala Gly Thr Thr Cys Gly Gly Cys Ala Ala
        290                 295                 300

Gly Ala Gly Gly Thr Ala Cys Gly Cys Cys Thr Gly Gly Ala Cys
305                 310                 315                 320

Thr Ala Cys Thr Gly Gly Gly Gly Ala Cys Ala Gly Gly Cys Ala
                    325                 330                 335

Cys Cys Ala Gly Cys Gly Thr Gly Ala Cys Cys Gly Thr Gly Ala Gly
                340                 345                 350

Cys Ala Gly Cys
        355

<210> SEQ ID NO 35
<211> LENGTH: 357
<212> TYPE: PRT
<213> ORGANISM: Artificial Sequence
<220> FEATURE:
<223> OTHER INFORMATION: Synthetic

<400> SEQUENCE: 35

Gly Ala Gly Gly Thr Gly Cys Ala Gly Cys Thr Gly Gly Thr Gly Gly
1               5                   10                  15

Ala Gly Ala Gly Cys Gly Gly Ala Gly Ala Gly Gly Ala Cys Thr
            20                  25                  30

Gly Gly Thr Gly Ala Ala Gly Cys Cys Gly Gly Ala Gly Gly Cys
        35                  40                  45

Ala Gly Cys Cys Thr Gly Ala Gly Ala Cys Thr Gly Ala Gly Cys Thr
50                  55                  60

Gly Cys Gly Cys Thr Gly Cys Cys Ala Gly Gly Gly Cys Thr Thr
65                  70                  75                  80

Cys Ala Cys Cys Thr Thr Cys Ala Gly Cys Ala Gly Cys Thr Ala Cys
                85                  90                  95

Gly Ala Cys Ala Thr Gly Ala Gly Cys Thr Gly Gly Thr Gly Ala
            100                 105                 110

Gly Ala Cys Ala Gly Gly Cys Cys Cys Cys Thr Gly Gly Cys Ala Ala
            115                 120                 125

Ala Gly Gly Cys Cys Thr Gly Gly Ala Gly Thr Gly Gly Gly Thr Gly
        130                 135                 140

Ala Gly Cys Ala Cys Cys Ala Thr Cys Thr Cys Cys Gly Ala Thr Gly
145                 150                 155                 160

Gly Cys Gly Gly Cys Gly Gly Cys Thr Ala Cys Ala Thr Cys Thr Ala
                165                 170                 175

Thr Thr Ala Cys Thr Cys Cys Gly Ala Cys Ala Gly Cys Gly Thr
            180                 185                 190

Ala Ala Gly Gly Gly Cys Ala Gly Gly Thr Thr Cys Ala Cys Cys Ala
            195                 200                 205

Thr Cys Ala Gly Cys Ala Gly Gly Gly Ala Cys Ala Ala Cys Gly Cys
        210                 215                 220

Cys Ala Ala Gly Ala Ala Cys Ala Gly Cys Cys Thr Gly Thr Ala Cys
225                 230                 235                 240

Cys Thr Gly Cys Ala Gly Ala Thr Gly Ala Ala Cys Ala Gly Cys Cys
                245                 250                 255

Thr Gly Ala Gly Gly Gly Cys Cys Gly Ala Gly Gly Ala Cys Ala Cys
            260                 265                 270

Cys Gly Cys Cys Gly Thr Gly Thr Ala Cys Thr Ala Cys Thr Gly Cys
            275                 280                 285

Gly Cys Cys Ala Gly Gly Gly Ala Gly Thr Thr Cys Gly Gly Cys Ala
        290                 295                 300

Ala Ala Ala Gly Gly Thr Ala Cys Gly Cys Cys Cys Thr Gly Gly Ala
305                 310                 315                 320

Cys Thr Ala Cys Thr Gly Gly Gly Gly Cys Ala Gly Gly Cys
                325                 330                 335

Ala Cys Ala Ala Cys Cys Gly Thr Gly Ala Cys Cys Thr Gly Ala
            340                 345                 350

Gly Cys Ala Gly Cys
        355

<210> SEQ ID NO 36
<211> LENGTH: 357
<212> TYPE: PRT
<213> ORGANISM: Artificial Sequence
<220> FEATURE:
<223> OTHER INFORMATION: Synthetic

<400> SEQUENCE: 36

Gly Ala Gly Gly Thr Gly Cys Ala Gly Cys Thr Gly Gly Thr Gly
1               5                   10                  15

Ala Gly Ala Gly Cys Gly Gly Ala Gly Gly Ala Gly Gly Cys Thr
            20                  25                  30

Gly Gly Thr Gly Ala Ala Gly Cys Cys Gly Gly Ala Gly Gly Cys
        35                  40                  45

Ala Gly Cys Cys Thr Gly Ala Gly Ala Cys Thr Gly Ala Gly Cys
50                  55                  60

Gly Cys Gly Cys Thr Gly Cys Cys Ala Gly Gly Cys Thr Thr
65                  70                  75                  80

Cys Ala Cys Cys Thr Thr Cys Ala Gly Cys Ala Gly Cys Ala Cys
                85                  90                  95

Gly Ala Cys Ala Thr Gly Ala Gly Cys Thr Gly Gly Thr Gly Ala
                100                 105                 110

Gly Ala Cys Ala Gly Gly Cys Cys Cys Thr Gly Gly Cys Ala Ala
                115                 120                 125

Ala Gly Gly Cys Cys Thr Gly Ala Gly Thr Gly Gly Gly Thr Gly
            130                 135                 140

Gly Cys Cys Ala Cys Cys Ala Thr Cys Thr Cys Gly Ala Thr Gly
145                 150                 155                 160

Gly Cys Gly Gly Cys Gly Gly Cys Thr Ala Cys Ala Thr Cys Ala
                165                 170                 175

Thr Thr Ala Cys Thr Cys Cys Gly Ala Cys Ala Gly Cys Gly Thr
                180                 185                 190

Ala Ala Gly Gly Gly Cys Ala Gly Gly Thr Thr Cys Ala Cys Cys
            195                 200                 205

Thr Cys Ala Gly Cys Ala Gly Gly Ala Cys Ala Ala Cys Gly Cys
        210                 215                 220

Cys Ala Ala Gly Ala Ala Cys Ala Gly Cys Cys Thr Gly Thr Ala
225                 230                 235                 240

Cys Thr Gly Cys Ala Gly Ala Thr Gly Ala Ala Cys Ala Gly Cys
                245                 250                 255

Thr Gly Ala Gly Gly Gly Cys Cys Gly Ala Gly Gly Ala Cys Ala
                260                 265                 270

Cys Gly Cys Cys Gly Thr Gly Thr Ala Cys Thr Ala Cys Thr Gly
                275                 280                 285

Gly Cys Cys Ala Gly Gly Gly Ala Gly Thr Thr Cys Gly Gly Cys Ala
        290                 295                 300

Ala Ala Ala Gly Gly Thr Ala Cys Gly Cys Cys Cys Thr Gly Gly Ala
305                 310                 315                 320

```
Cys Thr Ala Cys Thr Gly Gly Gly Gly Cys Ala Gly Gly Cys
                325                 330                 335

Ala Cys Ala Ala Cys Cys Gly Thr Gly Ala Cys Cys Thr Gly Ala
            340                 345                 350

Gly Cys Ala Gly Cys
        355

<210> SEQ ID NO 37
<211> LENGTH: 357
<212> TYPE: PRT
<213> ORGANISM: Artificial Sequence
<220> FEATURE:
<223> OTHER INFORMATION: Synthetic

<400> SEQUENCE: 37

Gly Ala Gly Gly Thr Gly Cys Ala Gly Cys Thr Gly Gly Thr Gly
1               5                   10                  15

Ala Gly Ala Gly Cys Gly Gly Ala Gly Gly Ala Gly Gly Cys Thr
            20                  25                  30

Gly Gly Thr Gly Ala Ala Gly Cys Cys Cys Gly Gly Ala Gly Gly
            35                  40                  45

Ala Gly Cys Cys Thr Gly Ala Gly Ala Cys Thr Gly Ala Gly Cys
50                  55                  60

Gly Cys Gly Cys Thr Gly Cys Cys Ala Cys Gly Gly Cys Thr Thr
65                  70                  75                  80

Cys Ala Cys Cys Thr Thr Cys Ala Gly Cys Ala Gly Cys Thr Ala
            85                  90                  95

Gly Ala Cys Ala Thr Gly Ala Gly Cys Thr Gly Gly Thr Gly Ala
            100                 105                 110

Gly Ala Cys Ala Gly Gly Cys Cys Cys Thr Gly Gly Cys Ala Ala
            115                 120                 125

Ala Ala Gly Cys Cys Thr Gly Gly Ala Gly Thr Gly Gly Thr Gly
        130                 135                 140

Gly Cys Cys Ala Cys Cys Ala Thr Cys Thr Cys Cys Gly Ala Thr
145                 150                 155                 160

Gly Cys Gly Gly Cys Gly Gly Cys Thr Ala Cys Ala Thr Cys Ala
            165                 170                 175

Thr Thr Ala Cys Thr Cys Cys Gly Ala Cys Ala Gly Cys Gly Thr
            180                 185                 190

Ala Ala Gly Gly Gly Cys Ala Gly Gly Thr Thr Cys Ala Cys Cys
        195                 200                 205

Thr Cys Ala Gly Cys Ala Gly Gly Ala Cys Ala Ala Cys Gly Cys
        210                 215                 220

Cys Ala Ala Gly Ala Ala Cys Ala Gly Cys Cys Thr Gly Thr Ala
225                 230                 235                 240

Cys Thr Gly Cys Ala Gly Ala Thr Gly Ala Ala Cys Ala Gly Cys
            245                 250                 255

Thr Gly Ala Gly Gly Gly Cys Cys Gly Ala Gly Gly Ala Cys Ala
            260                 265                 270

Cys Gly Cys Cys Gly Thr Gly Thr Ala Cys Ala Thr Cys Thr Gly
            275                 280                 285

Gly Cys Cys Ala Gly Gly Gly Ala Cys Thr Thr Cys Gly Gly Cys
        290                 295                 300

Ala Ala Ala Gly Gly Thr Ala Cys Gly Cys Cys Cys Thr Gly Ala
305                 310                 315                 320
```

```
Cys Thr Ala Cys Thr Gly Gly Gly Cys Ala Gly Gly Cys
            325                 330             335

Ala Cys Ala Ala Cys Cys Gly Thr Gly Ala Cys Cys Thr Gly Ala
        340                 345             350

Gly Cys Ala Gly Cys
        355

<210> SEQ ID NO 38
<211> LENGTH: 357
<212> TYPE: PRT
<213> ORGANISM: Artificial Sequence
<220> FEATURE:
<223> OTHER INFORMATION: Synthetic

<400> SEQUENCE: 38

Gly Ala Gly Gly Thr Gly Cys Ala Gly Cys Thr Gly Thr Gly Gly
1               5                   10                  15

Ala Gly Ala Gly Cys Gly Gly Ala Gly Ala Gly Gly Ala Cys Thr
            20                  25                  30

Gly Gly Thr Gly Ala Ala Gly Cys Cys Gly Gly Ala Gly Gly Cys
        35                  40                  45

Ala Gly Cys Cys Thr Gly Ala Gly Ala Cys Thr Gly Ala Gly Cys
    50                  55                  60

Gly Cys Gly Cys Thr Gly Cys Cys Ala Gly Gly Gly Cys Thr Thr
65                  70                  75                  80

Cys Ala Cys Cys Thr Thr Cys Ala Gly Cys Ala Gly Cys Thr Ala
            85                  90                  95

Gly Ala Cys Ala Thr Gly Ala Gly Cys Thr Gly Gly Ala Thr Cys
            100                 105                 110

Gly Ala Cys Ala Gly Cys Cys Cys Thr Gly Gly Cys Ala Ala Gly
        115                 120                 125

Ala Gly Gly Cys Cys Thr Gly Gly Ala Gly Thr Gly Gly Thr Gly
        130                 135                 140

Ala Gly Cys Ala Cys Cys Ala Thr Cys Thr Cys Cys Gly Ala Thr
145                 150                 155                 160

Gly Cys Gly Gly Cys Gly Gly Cys Thr Ala Cys Ala Cys Thr Ala
            165                 170                 175

Thr Thr Ala Cys Thr Cys Cys Gly Ala Cys Ala Gly Cys Gly Thr
            180                 185                 190

Ala Ala Gly Gly Gly Cys Ala Gly Gly Thr Thr Cys Ala Cys Cys
        195                 200                 205

Thr Cys Ala Gly Cys Ala Gly Gly Ala Cys Ala Ala Cys Gly Cys
        210                 215                 220

Cys Ala Ala Gly Ala Ala Cys Ala Gly Cys Cys Thr Gly Thr Ala
225                 230                 235                 240

Cys Thr Gly Cys Ala Gly Ala Thr Gly Ala Ala Cys Ala Gly Cys
            245                 250                 255

Thr Gly Ala Gly Gly Gly Cys Cys Gly Ala Gly Gly Ala Cys Ala
        260                 265                 270

Cys Gly Cys Cys Gly Thr Gly Thr Ala Cys Thr Ala Cys Thr Gly
        275                 280                 285

Gly Cys Cys Ala Gly Gly Gly Ala Cys Thr Cys Gly Gly Cys Ala
        290                 295                 300

Ala Ala Ala Gly Gly Thr Ala Cys Gly Cys Cys Cys Thr Gly Ala
305                 310                 315                 320
```

```
Cys Thr Ala Cys Thr Gly Gly Gly Gly Cys Ala Gly Gly Cys
                325                 330                 335

Ala Cys Ala Ala Cys Cys Gly Thr Gly Ala Cys Gly Thr Gly Ala
            340                 345                 350

Gly Cys Ala Gly Cys
        355

<210> SEQ ID NO 39
<211> LENGTH: 357
<212> TYPE: PRT
<213> ORGANISM: Artificial Sequence
<220> FEATURE:
<223> OTHER INFORMATION: Synthetic

<400> SEQUENCE: 39

Gly Ala Gly Gly Thr Gly Cys Ala Gly Cys Thr Gly Gly Thr Gly
1               5                   10                  15

Ala Gly Ala Gly Cys Gly Gly Ala Gly Gly Ala Gly Gly Ala Cys Thr
            20                  25                  30

Gly Gly Thr Gly Ala Ala Gly Cys Cys Cys Gly Gly Ala Gly Gly Cys
        35                  40                  45

Ala Gly Cys Cys Thr Gly Ala Gly Ala Cys Thr Gly Ala Gly Cys Thr
50                  55                  60

Gly Cys Gly Cys Thr Gly Cys Cys Ala Gly Gly Cys Thr Thr
65                  70                  75                  80

Cys Ala Cys Cys Thr Thr Cys Ala Gly Cys Ala Gly Cys Thr Ala Cys
                85                  90                  95

Gly Ala Cys Ala Thr Gly Ala Gly Cys Thr Gly Gly Ala Thr Cys Ala
                100                 105                 110

Gly Ala Cys Ala Gly Gly Cys Cys Cys Cys Thr Gly Gly Cys Ala Ala
                115                 120                 125

Ala Gly Gly Cys Cys Thr Gly Gly Ala Gly Thr Gly Gly Gly Thr Gly
            130                 135                 140

Gly Cys Cys Ala Cys Ala Thr Cys Thr Cys Gly Ala Thr Gly
145                 150                 155                 160

Gly Cys Gly Gly Cys Gly Gly Cys Thr Ala Cys Ala Thr Cys Thr Ala
                165                 170                 175

Thr Thr Ala Cys Thr Cys Cys Gly Ala Cys Ala Gly Cys Gly Thr Gly
            180                 185                 190

Ala Ala Gly Gly Gly Cys Ala Gly Gly Thr Thr Cys Ala Cys Cys Ala
            195                 200                 205

Thr Cys Ala Gly Cys Ala Gly Gly Ala Cys Ala Ala Cys Gly Cys
        210                 215                 220

Cys Ala Ala Gly Ala Ala Cys Ala Gly Cys Cys Thr Gly Thr Ala Cys
225                 230                 235                 240

Cys Thr Gly Cys Ala Gly Ala Thr Gly Ala Ala Cys Ala Gly Cys Cys
                245                 250                 255

Thr Gly Ala Gly Gly Gly Cys Cys Gly Ala Gly Gly Ala Cys Ala Cys
            260                 265                 270

Cys Gly Cys Cys Gly Thr Gly Thr Ala Cys Thr Ala Cys Thr Gly Cys
                275                 280                 285

Gly Cys Cys Ala Gly Gly Gly Ala Thr Thr Cys Gly Gly Cys Ala
        290                 295                 300

Ala Ala Ala Gly Gly Thr Ala Cys Gly Cys Cys Cys Thr Gly Gly Ala
305                 310                 315                 320
```

```
Cys Thr Ala Cys Thr Gly Gly Gly Gly Cys Ala Gly Gly Cys
                325                 330                 335

Ala Cys Ala Ala Cys Cys Gly Thr Gly Ala Cys Gly Thr Gly Ala
            340                 345                 350

Gly Cys Ala Gly Cys
        355

<210> SEQ ID NO 40
<211> LENGTH: 357
<212> TYPE: PRT
<213> ORGANISM: Artificial Sequence
<220> FEATURE:
<223> OTHER INFORMATION: Synthetic

<400> SEQUENCE: 40

Gly Ala Gly Gly Thr Gly Cys Ala Gly Cys Thr Gly Thr Gly Gly
1               5                   10                  15

Ala Gly Ala Gly Cys Gly Gly Ala Gly Gly Ala Gly Ala Cys Thr
            20                  25                  30

Gly Gly Thr Gly Ala Ala Gly Cys Cys Gly Gly Ala Gly Gly Cys
        35                  40                  45

Ala Gly Cys Cys Thr Gly Ala Gly Ala Cys Thr Gly Ala Gly Cys
50                  55                  60

Gly Cys Gly Cys Thr Gly Cys Cys Ala Gly Gly Gly Cys Thr Thr
65                  70                  75                  80

Cys Ala Cys Cys Thr Thr Cys Ala Gly Cys Ala Gly Cys Ala Cys
                85                  90                  95

Gly Ala Cys Ala Thr Gly Ala Gly Cys Thr Gly Gly Thr Gly Ala
                100                 105                 110

Gly Ala Cys Ala Gly Gly Cys Cys Cys Cys Thr Gly Gly Cys Ala
                115                 120                 125

Ala Ala Gly Cys Cys Thr Gly Gly Ala Gly Thr Gly Gly Gly Thr
            130                 135                 140

Gly Cys Cys Ala Cys Cys Ala Thr Cys Thr Cys Cys Gly Ala Thr
145                 150                 155                 160

Gly Cys Gly Gly Cys Gly Gly Cys Thr Ala Cys Ala Thr Cys Thr
                165                 170                 175

Thr Thr Ala Cys Thr Cys Cys Gly Ala Cys Ala Gly Cys Gly Thr
                180                 185                 190

Ala Ala Gly Gly Gly Cys Ala Gly Gly Thr Thr Cys Ala Cys Cys
            195                 200                 205

Thr Cys Ala Gly Cys Ala Gly Gly Ala Cys Ala Ala Cys Gly Cys
        210                 215                 220

Cys Ala Ala Gly Ala Ala Cys Ala Gly Cys Cys Thr Gly Thr Ala
225                 230                 235                 240

Cys Thr Gly Cys Ala Gly Ala Thr Gly Ala Ala Cys Ala Gly Cys
                245                 250                 255

Thr Gly Ala Gly Gly Gly Cys Cys Gly Ala Gly Gly Ala Cys Ala
                260                 265                 270

Cys Gly Cys Cys Gly Thr Gly Thr Ala Cys Ala Thr Cys Thr Gly
                275                 280                 285

Gly Cys Cys Ala Gly Gly Gly Ala Gly Thr Cys Gly Gly Cys Ala
            290                 295                 300

Ala Ala Ala Gly Gly Thr Ala Cys Gly Cys Cys Cys Thr Gly Ala
305                 310                 315                 320
```

```
Cys Thr Ala Cys Thr Gly Gly Gly Gly Cys Ala Gly Gly Cys
                325                 330                 335

Ala Cys Ala Ala Cys Cys Gly Thr Gly Ala Cys Cys Gly Thr Gly Ala
            340                 345                 350

Gly Cys Ala Gly Cys
        355

<210> SEQ ID NO 41
<211> LENGTH: 357
<212> TYPE: PRT
<213> ORGANISM: Artificial Sequence
<220> FEATURE:
<223> OTHER INFORMATION: Synthetic

<400> SEQUENCE: 41

Gly Ala Gly Gly Thr Gly Cys Ala Gly Cys Thr Gly Cys Thr Gly Gly
1               5                   10                  15

Ala Gly Ala Gly Cys Gly Gly Ala Gly Gly Ala Gly Gly Ala Cys Thr
            20                  25                  30

Gly Gly Thr Gly Cys Ala Ala Cys Cys Gly Gly Ala Gly Gly Cys
        35                  40                  45

Ala Gly Cys Cys Thr Gly Ala Gly Ala Cys Thr Gly Ala Gly Cys Thr
50                  55                  60

Gly Cys Gly Cys Thr Gly Cys Cys Ala Gly Gly Cys Thr Thr
65                  70                  75              80

Cys Ala Cys Cys Thr Thr Cys Ala Gly Cys Ala Gly Cys Thr Ala Cys
                85                  90                  95

Gly Ala Cys Ala Thr Gly Ala Gly Cys Thr Gly Gly Gly Thr Gly Ala
                100                 105                 110

Gly Ala Cys Ala Gly Gly Cys Cys Cys Cys Thr Gly Gly Cys Ala Ala
            115                 120                 125

Ala Gly Gly Cys Cys Thr Gly Gly Ala Gly Thr Gly Gly Gly Thr Gly
            130                 135                 140

Ala Gly Cys Ala Cys Cys Ala Thr Cys Thr Cys Cys Gly Ala Thr Gly
145                 150                 155                 160

Gly Cys Gly Gly Cys Gly Gly Cys Thr Ala Cys Ala Cys Cys Thr Ala
                165                 170                 175

Thr Thr Ala Cys Thr Cys Cys Gly Ala Cys Ala Gly Cys Gly Thr Gly
                180                 185                 190

Ala Ala Gly Gly Gly Cys Ala Gly Gly Thr Thr Cys Ala Cys Cys Ala
            195                 200                 205

Thr Cys Ala Gly Cys Ala Gly Gly Gly Ala Cys Ala Ala Cys Ala Gly
        210                 215                 220

Cys Ala Ala Gly Ala Ala Cys Ala Cys Cys Cys Thr Gly Thr Ala Cys
225                 230                 235                 240

Cys Thr Gly Cys Ala Gly Ala Thr Gly Ala Ala Cys Ala Gly Cys Cys
                245                 250                 255

Thr Gly Ala Gly Gly Gly Cys Cys Gly Ala Gly Gly Ala Cys Ala Cys
            260                 265                 270

Cys Gly Cys Cys Gly Thr Gly Thr Ala Cys Thr Ala Cys Thr Gly Cys
        275                 280                 285

Gly Cys Cys Ala Gly Gly Gly Ala Gly Thr Cys Gly Gly Cys Ala
        290                 295                 300

Ala Ala Ala Gly Gly Thr Ala Cys Gly Cys Cys Cys Thr Gly Gly Ala
305                 310                 315                 320
```

```
Cys Thr Ala Cys Thr Gly Gly Gly Gly Cys Ala Gly Gly Cys
                325                 330                 335

Ala Cys Ala Ala Cys Cys Gly Thr Gly Ala Cys Cys Gly Thr Gly Ala
            340                 345                 350

Gly Cys Ala Gly Cys
        355

<210> SEQ ID NO 42
<211> LENGTH: 357
<212> TYPE: PRT
<213> ORGANISM: Artificial Sequence
<220> FEATURE:
<223> OTHER INFORMATION: Synthetic

<400> SEQUENCE: 42

Gly Ala Gly Gly Thr Gly Cys Ala Gly Cys Thr Gly Cys Thr Gly Gly
1               5                   10                  15

Ala Gly Ala Gly Cys Gly Gly Ala Gly Gly Ala Gly Gly Ala Cys Thr
            20                  25                  30

Gly Gly Thr Gly Cys Ala Ala Cys Cys Cys Gly Gly Ala Gly Gly Cys
        35                  40                  45

Ala Gly Cys Cys Thr Gly Ala Gly Ala Cys Thr Gly Ala Gly Cys Thr
50                  55                  60

Gly Cys Gly Cys Thr Gly Cys Cys Ala Gly Cys Gly Cys Thr Thr
65                  70                  75                  80

Cys Ala Cys Cys Thr Thr Cys Ala Gly Cys Ala Gly Cys Thr Ala Cys
                85                  90                  95

Gly Ala Cys Ala Thr Gly Ala Gly Cys Thr Gly Gly Gly Thr Gly Ala
                100                 105                 110

Gly Ala Cys Ala Gly Gly Cys Cys Cys Thr Gly Gly Cys Ala Ala
                115                 120                 125

Ala Ala Gly Cys Cys Thr Gly Gly Ala Gly Thr Gly Gly Gly Thr Gly
            130                 135                 140

Gly Cys Cys Ala Cys Cys Ala Thr Cys Thr Cys Cys Gly Ala Thr Gly
145                 150                 155                 160

Gly Cys Gly Gly Cys Gly Gly Cys Thr Ala Cys Ala Thr Cys Thr Ala
                165                 170                 175

Thr Thr Ala Cys Thr Cys Cys Gly Ala Cys Ala Gly Cys Gly Thr Gly
            180                 185                 190

Ala Ala Gly Gly Gly Cys Ala Gly Gly Thr Thr Cys Ala Cys Cys Ala
            195                 200                 205

Thr Cys Ala Gly Cys Ala Gly Gly Ala Cys Ala Ala Cys Ala Gly
        210                 215                 220

Cys Ala Ala Gly Ala Ala Cys Ala Cys Cys Thr Gly Thr Ala Cys
225                 230                 235                 240

Cys Thr Gly Cys Ala Gly Ala Thr Gly Ala Ala Cys Ala Gly Cys Cys
                245                 250                 255

Thr Gly Ala Gly Gly Cys Cys Gly Ala Gly Gly Ala Cys Ala Cys
            260                 265                 270

Cys Gly Cys Cys Gly Thr Gly Thr Ala Cys Ala Thr Cys Thr Gly Cys
                275                 280                 285

Gly Cys Cys Ala Gly Gly Gly Ala Thr Thr Cys Gly Gly Cys Ala
            290                 295                 300

Ala Ala Ala Gly Gly Thr Ala Cys Gly Cys Cys Cys Thr Gly Gly Ala
305                 310                 315                 320
```

```
Cys Thr Ala Cys Thr Gly Gly Gly Gly Cys Ala Gly Gly Cys
                325                 330                 335

Ala Cys Ala Ala Cys Cys Gly Thr Gly Ala Cys Gly Thr Gly Ala
            340                 345                 350

Gly Cys Ala Gly Cys
        355

<210> SEQ ID NO 43
<211> LENGTH: 357
<212> TYPE: PRT
<213> ORGANISM: Artificial Sequence
<220> FEATURE:
<223> OTHER INFORMATION: Synthetic

<400> SEQUENCE: 43

Gly Ala Gly Gly Thr Gly Cys Ala Gly Cys Thr Gly Gly Thr Gly
1               5                   10                  15

Ala Gly Ala Gly Cys Gly Gly Ala Gly Gly Ala Gly Gly Cys Thr
            20                  25                  30

Gly Gly Thr Gly Cys Ala Ala Cys Cys Gly Gly Ala Gly Gly Cys
        35                  40                  45

Ala Gly Cys Cys Thr Gly Ala Gly Ala Cys Thr Gly Ala Gly Cys
50                  55                  60

Gly Cys Gly Cys Thr Gly Cys Cys Ala Gly Cys Gly Cys Thr Thr
65                  70                  75                  80

Cys Ala Cys Cys Thr Thr Cys Ala Gly Cys Ala Gly Cys Thr Ala
                85                  90                  95

Gly Ala Cys Ala Thr Gly Ala Gly Cys Thr Gly Gly Thr Gly Ala
            100                 105                 110

Gly Ala Cys Ala Gly Gly Cys Cys Cys Thr Gly Gly Cys Ala Ala
            115                 120                 125

Ala Gly Gly Cys Cys Thr Gly Gly Ala Gly Thr Gly Gly Gly Thr
            130                 135                 140

Ala Gly Cys Ala Cys Cys Ala Thr Cys Thr Cys Gly Ala Thr Gly
145                 150                 155                 160

Gly Cys Gly Gly Cys Gly Gly Cys Thr Ala Cys Ala Thr Cys Ala
            165                 170                 175

Thr Thr Ala Cys Thr Cys Cys Gly Ala Cys Ala Gly Cys Gly Thr
            180                 185                 190

Ala Ala Gly Gly Gly Cys Ala Gly Gly Thr Thr Cys Ala Cys Cys
            195                 200                 205

Thr Cys Ala Gly Cys Ala Gly Gly Ala Cys Ala Ala Cys Gly Cys
            210                 215                 220

Cys Ala Ala Gly Ala Ala Cys Ala Gly Cys Cys Thr Gly Thr Ala
225                 230                 235                 240

Cys Thr Gly Cys Ala Gly Ala Thr Gly Ala Ala Cys Ala Gly Cys
            245                 250                 255

Thr Gly Ala Gly Gly Ala Thr Gly Ala Gly Gly Ala Cys Ala Cys
            260                 265                 270

Cys Gly Cys Cys Gly Thr Gly Thr Ala Cys Thr Ala Cys Thr Gly
            275                 280                 285

Gly Cys Cys Ala Gly Gly Gly Ala Thr Thr Cys Gly Gly Cys Ala
        290                 295                 300

Ala Ala Ala Gly Gly Thr Ala Cys Gly Cys Cys Cys Thr Gly Ala
305                 310                 315                 320
```

Cys Thr Ala Cys Thr Gly Gly Gly Gly Cys Ala Gly Gly Cys
                    325                 330                 335

Ala Cys Ala Ala Cys Cys Gly Thr Gly Ala Cys Gly Thr Gly Ala
                340                 345                 350

Gly Cys Ala Gly Cys
            355

<210> SEQ ID NO 44
<211> LENGTH: 357
<212> TYPE: PRT
<213> ORGANISM: Artificial Sequence
<220> FEATURE:
<223> OTHER INFORMATION: Synthetic

<400> SEQUENCE: 44

Gly Ala Gly Gly Thr Gly Cys Ala Gly Cys Thr Gly Thr Gly Gly
1               5                   10                  15

Ala Gly Ala Gly Cys Gly Gly Ala Gly Gly Ala Gly Gly Ala Cys Thr
                20                  25                  30

Gly Gly Thr Gly Cys Ala Ala Cys Cys Gly Gly Ala Gly Gly Cys
            35                  40                  45

Ala Gly Cys Cys Thr Gly Ala Gly Ala Cys Thr Gly Ala Gly Cys Thr
50                  55                  60

Gly Cys Gly Cys Thr Gly Cys Cys Ala Gly Cys Gly Cys Thr Thr
65                  70                  75                  80

Cys Ala Cys Cys Thr Thr Cys Ala Gly Cys Ala Gly Cys Ala Cys
                85                  90                  95

Gly Ala Cys Ala Thr Gly Ala Gly Cys Thr Gly Gly Gly Thr Gly Ala
                100                 105                 110

Gly Ala Cys Ala Gly Gly Cys Cys Cys Cys Thr Gly Gly Cys Ala Ala
                115                 120                 125

Ala Gly Gly Cys Cys Thr Gly Gly Ala Gly Thr Gly Gly Gly Thr Gly
                130                 135                 140

Gly Cys Cys Ala Cys Cys Ala Thr Cys Thr Cys Cys Gly Ala Thr Gly
145                 150                 155                 160

Gly Cys Gly Gly Cys Gly Gly Cys Thr Ala Cys Ala Cys Thr Ala
                165                 170                 175

Thr Thr Ala Cys Thr Cys Cys Gly Ala Cys Ala Gly Cys Gly Thr Gly
                180                 185                 190

Ala Ala Gly Gly Gly Cys Ala Gly Gly Thr Thr Cys Ala Cys Cys Ala
                195                 200                 205

Thr Cys Ala Gly Cys Ala Gly Gly Ala Cys Ala Ala Cys Gly Cys
                210                 215                 220

Cys Ala Ala Gly Ala Ala Cys Ala Gly Cys Cys Thr Gly Thr Ala Cys
225                 230                 235                 240

Cys Thr Gly Cys Ala Gly Ala Thr Gly Ala Ala Cys Ala Gly Cys Cys
                245                 250                 255

Thr Gly Ala Gly Gly Ala Thr Gly Ala Gly Gly Ala Cys Ala Cys
                260                 265                 270

Cys Gly Cys Cys Gly Thr Gly Thr Ala Cys Thr Ala Cys Thr Gly Cys
                275                 280                 285

Gly Cys Cys Ala Gly Gly Ala Gly Thr Thr Cys Gly Gly Cys Ala
                290                 295                 300

Ala Ala Ala Gly Gly Thr Ala Cys Gly Cys Cys Cys Thr Gly Gly Ala
305                 310                 315                 320

-continued

```
Cys Thr Ala Cys Thr Gly Gly Gly Gly Cys Ala Gly Gly Cys
                325                 330                 335

Ala Cys Ala Ala Cys Cys Gly Thr Gly Ala Cys Cys Gly Thr Gly Ala
        340                 345                 350

Gly Cys Ala Gly Cys
        355

<210> SEQ ID NO 45
<211> LENGTH: 357
<212> TYPE: PRT
<213> ORGANISM: Artificial Sequence
<220> FEATURE:
<223> OTHER INFORMATION: Synthetic

<400> SEQUENCE: 45

Gly Ala Gly Gly Thr Gly Cys Ala Gly Cys Thr Gly Thr Gly Gly
1               5                   10                  15

Ala Gly Ala Gly Cys Gly Gly Ala Gly Ala Gly Gly Ala Cys Thr
                20                  25                  30

Gly Gly Thr Gly Cys Ala Ala Cys Cys Gly Gly Ala Gly Gly Cys
        35                  40                  45

Ala Gly Cys Cys Thr Gly Ala Gly Ala Cys Thr Gly Ala Gly Cys Thr
50                  55                  60

Gly Cys Gly Cys Thr Gly Cys Cys Ala Gly Gly Gly Cys Thr Thr
65                  70                  75                  80

Cys Ala Cys Cys Thr Thr Cys Ala Gly Cys Ala Gly Cys Thr Ala Cys
                85                  90                  95

Gly Ala Cys Ala Thr Gly Ala Gly Cys Thr Gly Gly Thr Gly Ala
                100                 105                 110

Gly Ala Cys Ala Gly Gly Cys Cys Cys Cys Thr Gly Gly Cys Ala Ala
                115                 120                 125

Ala Ala Gly Cys Cys Thr Gly Gly Ala Gly Thr Gly Gly Gly Thr Gly
        130                 135                 140

Gly Cys Cys Ala Cys Cys Ala Thr Cys Thr Cys Cys Gly Ala Thr Gly
145                 150                 155                 160

Gly Cys Gly Gly Cys Gly Gly Cys Thr Ala Cys Ala Thr Cys Thr Ala
                165                 170                 175

Thr Thr Ala Cys Thr Cys Cys Gly Ala Cys Ala Gly Cys Gly Thr Gly
                180                 185                 190

Ala Ala Gly Gly Gly Cys Ala Gly Gly Thr Thr Cys Ala Cys Cys Ala
                195                 200                 205

Thr Cys Ala Gly Cys Ala Gly Gly Ala Cys Ala Ala Cys Gly Cys
        210                 215                 220

Cys Ala Ala Gly Ala Ala Cys Ala Gly Cys Cys Thr Gly Thr Ala Cys
225                 230                 235                 240

Cys Thr Gly Cys Ala Gly Ala Thr Gly Ala Ala Cys Ala Gly Cys Cys
                245                 250                 255

Thr Gly Ala Gly Gly Gly Ala Thr Gly Ala Gly Gly Ala Cys Ala Cys
                260                 265                 270

Cys Gly Cys Cys Gly Thr Gly Thr Ala Cys Ala Thr Cys Thr Gly Cys
                275                 280                 285

Gly Cys Cys Ala Gly Gly Gly Ala Thr Thr Cys Gly Gly Cys Ala
        290                 295                 300

Ala Ala Ala Gly Gly Thr Ala Cys Gly Cys Cys Cys Thr Gly Gly Ala
305                 310                 315                 320
```

```
Cys Thr Ala Cys Thr Gly Gly Gly Gly Cys Ala Gly Gly Cys
                325                 330                 335

Ala Cys Ala Ala Cys Cys Gly Thr Gly Ala Cys Gly Thr Gly Ala
            340                 345                 350

Gly Cys Ala Gly Cys
        355

<210> SEQ ID NO 46
<211> LENGTH: 357
<212> TYPE: PRT
<213> ORGANISM: Artificial Sequence
<220> FEATURE:
<223> OTHER INFORMATION: Synthetic

<400> SEQUENCE: 46

Gly Ala Gly Gly Thr Gly Cys Ala Gly Cys Thr Gly Thr Gly Gly
1               5                   10                  15

Ala Gly Ala Gly Cys Gly Gly Ala Gly Gly Ala Gly Gly Ala Cys Thr
            20                  25                  30

Gly Gly Thr Gly Cys Ala Ala Cys Cys Gly Gly Ala Gly Gly Cys
        35                  40                  45

Ala Gly Cys Cys Thr Gly Ala Gly Ala Cys Thr Gly Ala Gly Cys
50                  55                  60

Gly Cys Gly Cys Thr Gly Cys Cys Ala Cys Gly Gly Cys Thr Thr
65                  70                  75                  80

Cys Ala Cys Cys Thr Thr Cys Ala Gly Cys Ala Gly Cys Thr Ala Cys
                85                  90                  95

Gly Ala Cys Ala Thr Gly Ala Gly Cys Thr Gly Gly Thr Gly Ala
            100                 105                 110

Gly Ala Cys Ala Gly Gly Cys Cys Cys Cys Thr Gly Gly Cys Ala Ala
            115                 120                 125

Ala Ala Gly Cys Cys Thr Gly Gly Ala Gly Thr Gly Gly Gly Thr Gly
        130                 135                 140

Gly Cys Cys Ala Cys Cys Ala Thr Cys Thr Cys Cys Gly Ala Ala Gly
145                 150                 155                 160

Gly Cys Gly Gly Cys Gly Gly Cys Thr Ala Cys Ala Thr Cys Thr Ala
                165                 170                 175

Thr Thr Ala Cys Thr Cys Cys Gly Ala Cys Ala Gly Cys Gly Thr Gly
            180                 185                 190

Ala Ala Gly Gly Gly Cys Ala Gly Gly Thr Thr Cys Ala Cys Cys Ala
        195                 200                 205

Thr Cys Ala Gly Cys Ala Gly Gly Ala Cys Ala Ala Cys Gly Cys
210                 215                 220

Cys Ala Ala Gly Ala Ala Cys Ala Gly Cys Cys Thr Gly Thr Ala Cys
225                 230                 235                 240

Cys Thr Gly Cys Ala Gly Ala Thr Gly Ala Ala Cys Ala Gly Cys Cys
                245                 250                 255

Thr Gly Ala Gly Gly Ala Thr Gly Ala Gly Gly Ala Cys Ala Cys
            260                 265                 270

Cys Gly Cys Cys Gly Thr Gly Thr Ala Cys Ala Thr Cys Thr Gly Cys
        275                 280                 285

Gly Cys Cys Ala Gly Gly Gly Ala Thr Thr Cys Gly Gly Cys Ala
290                 295                 300

Ala Ala Ala Gly Gly Thr

```
Cys Thr Ala Cys Thr Gly Gly Gly Cys Ala Gly Gly Cys
                325                 330             335

Ala Cys Ala Ala Cys Cys Gly Thr Gly Ala Cys Gly Thr Gly Ala
        340                 345                 350

Gly Cys Ala Gly Cys
        355

<210> SEQ ID NO 47
<211> LENGTH: 357
<212> TYPE: PRT
<213> ORGANISM: Artificial Sequence
<220> FEATURE:
<223> OTHER INFORMATION: Synthetic

<400> SEQUENCE: 47

Gly Ala Gly Gly Thr Gly Cys Ala Gly Cys Thr Gly Gly Thr Gly
1               5                   10                  15

Ala Gly Ala Gly Cys Gly Gly Ala Gly Gly Ala Gly Gly Cys Thr
            20                  25                  30

Gly Gly Thr Gly Cys Ala Ala Cys Cys Gly Gly Ala Gly Gly Cys
            35                  40                  45

Ala Gly Cys Cys Thr Gly Ala Gly Ala Cys Thr Gly Ala Gly Cys
50                  55                  60

Gly Cys Gly Cys Thr Gly Cys Cys Ala Gly Gly Gly Cys Thr Thr
65                  70                  75                  80

Cys Ala Cys Cys Thr Thr Cys Ala Gly Cys Ala Gly Cys Ala Cys
                85                  90                  95

Gly Ala Cys Ala Thr Gly Ala Gly Cys Thr Gly Gly Thr Gly Ala
                100                 105                 110

Gly Ala Cys Ala Gly Gly Cys Cys Cys Thr Gly Gly Cys Ala Ala
                115                 120                 125

Ala Ala Gly Cys Cys Thr Gly Gly Ala Gly Thr Gly Gly Thr Gly
            130                 135                 140

Gly Cys Cys Ala Cys Cys Ala Thr Cys Thr Cys Gly Ala Thr Gly
145                 150                 155                 160

Cys Gly Gly Gly Cys Gly Gly Cys Thr Ala Cys Ala Thr Cys Thr
                165                 170                 175

Thr Thr Ala Cys Thr Cys Cys Gly Ala Cys Ala Gly Cys Gly Thr
                180                 185                 190

Ala Ala Gly Gly Gly Cys Ala Gly Gly Thr Thr Cys Ala Cys Cys
            195                 200                 205

Thr Cys Ala Gly Cys Ala Gly Gly Ala Cys Ala Ala Cys Gly Cys
        210                 215                 220

Cys Ala Ala Gly Ala Ala Cys Ala Gly Cys Cys Thr Gly Thr Ala
225                 230                 235                 240

Cys Thr Gly Cys Ala Gly Ala Thr Gly Ala Ala Cys Ala Gly Cys
            245                 250                 255

Thr Gly Ala Gly Gly Ala Thr Gly Ala Gly Gly Ala Cys Ala Cys
            260                 265                 270

Cys Gly Cys Cys Gly Thr Gly Thr Ala Cys Ala Thr Cys Thr Gly
            275                 280                 285

Gly Cys Cys Ala Gly Gly Gly Ala Cys Cys Gly Gly Cys Ala
        290                 295                 300

Ala Ala Ala Gly Gly Thr Ala Cys Gly Cys Cys Cys Thr Gly Ala
305                 310                 315                 320
```

```
Cys Thr Ala Cys Thr Gly Gly Gly Gly Cys Ala Gly Gly Cys
                325                 330                 335

Ala Cys Ala Ala Cys Cys Gly Thr Gly Ala Cys Cys Gly Thr Gly Ala
            340                 345                 350

Gly Cys Ala Gly Cys
        355

<210> SEQ ID NO 48
<211> LENGTH: 357
<212> TYPE: PRT
<213> ORGANISM: Artificial Sequence
<220> FEATURE:
<223> OTHER INFORMATION: Synthetic

<400> SEQUENCE: 48

Gly Ala Gly Gly Thr Gly Cys Ala Gly Cys Thr Gly Gly Thr Gly Gly
1               5                   10                  15

Ala Gly Ala Gly Cys Gly Gly Ala Gly Gly Ala Gly Gly Ala Cys Thr
            20                  25                  30

Gly Gly Thr Gly Cys Ala Ala Cys Cys Gly Gly Ala Gly Gly Cys
        35                  40                  45

Ala Gly Cys Cys Thr Gly Ala Gly Ala Cys Thr Gly Ala Gly Cys Thr
50                  55                  60

Gly Cys Gly Cys Thr Gly Cys Cys Ala Gly Cys Gly Gly Cys Thr Thr
65                  70                  75                  80

Cys Ala Cys Cys Thr Thr Cys Ala Gly Cys Ala Gly Cys Thr Ala Cys
                85                  90                  95

Gly Ala Cys Ala Thr Gly Ala Gly Cys Thr Gly Gly Gly Thr Gly Ala
            100                 105                 110

Gly Ala Cys Ala Gly Gly Cys Cys Cys Cys Thr Gly Gly Cys Ala Ala
            115                 120                 125

Ala Ala Gly Cys Cys Thr Gly Gly Ala Gly Thr Gly Gly Gly Thr Gly
        130                 135                 140

Gly Cys Cys Ala Cys Cys Ala Thr Cys Thr Cys Cys Gly Ala Thr Gly
145                 150                 155                 160

Thr Thr Gly Gly Cys Gly Gly Cys Thr Ala Cys Ala Thr Cys Thr Ala
                165                 170                 175

Thr Thr Ala Cys Thr Cys Cys Gly Ala Cys Ala Gly Cys Gly Thr Gly
            180                 185                 190

Ala Ala Gly Gly Gly Cys Ala Gly Gly Thr Thr Cys Ala Cys Cys Ala
            195                 200                 205

Thr Cys Ala Gly Cys Ala Gly Gly Ala Cys Ala Ala Cys Gly Cys
        210                 215                 220

Cys Ala Ala Gly Ala Ala Cys Ala Gly Cys Cys Thr Gly Thr Ala Cys
225                 230                 235                 240

Cys Thr Gly Cys Ala Gly Ala Thr Gly Ala Ala Cys Ala Gly Cys Cys
                245                 250                 255

Thr Gly Ala Gly Gly Gly Ala Thr Gly Ala Gly Gly Ala Cys Ala Cys
            260                 265                 270

Cys Gly Cys Cys Gly Thr Gly Thr Ala Cys Ala Thr Cys Thr Gly Cys
            275                 280                 285

Gly Cys Cys Ala Gly Gly Gly Ala Thr Thr Cys Gly Gly Cys Ala
        290                 295                 300

Ala Ala Ala Gly Gly Thr Ala Cys Gly Cys Cys Cys Thr Gly Gly Ala
305                 310                 315                 320
```

Cys Thr Ala Cys Thr Gly Gly Gly Gly Cys Ala Gly Gly Cys
                325                 330                 335

Ala Cys Ala Ala Cys Cys Gly Thr Gly Ala Cys Gly Thr Gly Ala
            340                 345                 350

Gly Cys Ala Gly Cys
        355

<210> SEQ ID NO 49
<211> LENGTH: 357
<212> TYPE: PRT
<213> ORGANISM: Artificial Sequence
<220> FEATURE:
<223> OTHER INFORMATION: Synthetic

<400> SEQUENCE: 49

Gly Ala Gly Gly Thr Gly Cys Ala Gly Cys Thr Gly Thr Gly Gly
1               5                   10                  15

Ala Gly Thr Cys Cys Gly Gly Ala Gly Ala Gly Gly Cys Cys Thr
            20                  25                  30

Gly Gly Thr Gly Cys Ala Ala Cys Thr Gly Gly Ala Gly Gly Cys
            35                  40                  45

Thr Cys Cys Cys Thr Gly Ala Gly Gly Cys Thr Gly Thr Cys Thr
    50                  55                  60

Gly Thr Gly Cys Cys Gly Cys Thr Thr Cys Gly Gly Cys Thr Thr
65                  70                  75                  80

Cys Ala Cys Cys Thr Thr Cys Ala Gly Cys Thr Cys Thr Ala Cys
            85                  90                  95

Gly Ala Thr Ala Thr Gly Ala Gly Cys Thr Gly Gly Thr Gly Ala
            100                 105                 110

Gly Gly Cys Ala Gly Gly Cys Thr Cys Cys Thr Gly Gly Ala Ala
            115                 120                 125

Gly Gly Gly Cys Cys Thr Gly Gly Ala Gly Thr Gly Gly Gly Thr
        130                 135                 140

Gly Cys Cys Ala Cys Cys Ala Thr Cys Thr Cys Gly Ala Cys Gly
145                 150                 155                 160

Gly Ala Gly Gly Cys Gly Gly Cys Thr Ala Cys Ala Thr Cys Thr
            165                 170                 175

Cys Thr Ala Cys Thr Cys Cys Gly Ala Cys Thr Cys Gly Thr Gly
            180                 185                 190

Ala Ala Gly Gly Gly Cys Ala Gly Gly Thr Thr Cys Ala Cys Cys
            195                 200                 205

Thr Cys Thr Cys Cys Gly Gly Ala Cys Ala Ala Cys Gly Cys
    210                 215                 220

Cys Ala Ala Gly Ala Ala Cys Thr Cys Cys Cys Thr Gly Thr Ala
225                 230                 235                 240

Cys Thr Gly Cys Ala Gly Ala Thr Gly Ala Ala Cys Thr Cys Thr
            245                 250                 255

Thr Cys Ala Gly Gly Cys Thr Gly Ala Gly Gly Ala Cys Ala Cys
            260                 265                 270

Cys Gly Cys Cys Gly Thr Gly Thr Ala Thr Thr Ala Cys Thr Gly
        275                 280                 285

Gly Cys Cys Ala Gly Gly Gly Ala Thr Thr Thr Gly Gly Cys Ala
        290                 295                 300

Ala Gly Ala Gly Gly Thr Ala Cys Gly Cys Cys Cys Thr Gly Ala
305                 310                 315                 320

```
Thr Thr Ala Cys Thr Gly Gly Gly Cys Ala Gly Gly Cys
            325                 330             335

Ala Cys Ala Cys Thr Gly Gly Thr Gly Ala Cys Ala Gly Thr Gly Ala
            340                 345             350

Gly Cys Thr Cys Cys
        355

<210> SEQ ID NO 50
<211> LENGTH: 357
<212> TYPE: PRT
<213> ORGANISM: Artificial Sequence
<220> FEATURE:
<223> OTHER INFORMATION: Synthetic

<400> SEQUENCE: 50

Gly Ala Gly Gly Thr Gly Cys Ala Gly Cys Thr Gly Thr Gly Gly
1               5                   10                  15

Ala Gly Thr Cys Cys Gly Gly Ala Gly Ala Gly Gly Cys Cys Thr
                20                  25                  30

Gly Gly Thr Gly Cys Ala Ala Cys Cys Thr Gly Gly Ala Gly Gly Cys
            35                  40                  45

Thr Cys Cys Cys Thr Gly Ala Gly Gly Cys Thr Gly Thr Cys Cys Thr
50                      55                  60

Gly Thr Gly Cys Cys Gly Cys Thr Thr Cys Cys Gly Gly Cys Thr Thr
65                  70                  75                  80

Cys Ala Cys Cys Thr Thr Cys Ala Gly Cys Thr Cys Thr Ala Cys
                85                  90                  95

Gly Ala Thr Ala Thr Gly Ala Gly Cys Thr Gly Gly Gly Thr Gly Ala
                100                 105                 110

Gly Gly Cys Ala Gly Gly Cys Thr Cys Cys Thr Gly Gly Ala Ala Ala
            115                 120                 125

Gly Gly Gly Cys Cys Thr Gly Gly Ala Gly Thr Gly Gly Gly Thr Gly
            130                 135                 140

Gly Cys Cys Ala Cys Ala Thr Cys Thr Cys Gly Ala Cys Gly
145                 150                 155                 160

Gly Ala Gly Gly Cys Gly Gly Cys Thr Ala Cys Ala Thr Cys Thr Ala
                165                 170                 175

Cys Thr Ala Cys Thr Cys Cys Gly Ala Cys Thr Cys Cys Gly Thr Gly
            180                 185                 190

Ala Ala Gly Gly Gly Cys Ala Gly Gly Thr Thr Cys Ala Cys Cys Ala
            195                 200                 205

Thr Cys Thr Cys Cys Gly Gly Ala Cys Ala Ala Cys Gly Cys
            210                 215                 220

Cys Ala Ala Gly Ala Ala Cys Thr Cys Cys Thr Gly Thr Ala Cys
225                 230                 235                 240

Cys Thr Gly Cys Ala Gly Ala Thr Gly Ala Ala Cys Thr Cys Thr Cys
            245                 250                 255

Thr Cys Ala Gly Gly Cys Thr Gly Ala Gly Gly Ala Cys Ala Cys
            260                 265                 270

Cys Gly Cys Cys Gly Thr Gly Thr Ala Thr Cys Thr Gly Cys
        275                 280                 285

Gly Cys Cys Ala Gly Gly Ala Thr Thr Thr Gly Gly Cys Ala
        290                 295                 300

Ala Gly Ala Gly Gly Thr Ala Cys Gly Cys Cys Cys Thr Gly Gly Ala
305                 310                 315                 320
```

```
Thr Thr Ala Cys Thr Gly Gly Gly Gly Cys Ala Gly Gly Cys
                325                 330                 335

Ala Cys Ala Cys Thr Gly Gly Thr Gly Ala Cys Ala Gly Thr Gly Ala
            340                 345                 350

Gly Cys Thr Cys Cys
        355

<210> SEQ ID NO 51
<211> LENGTH: 357
<212> TYPE: PRT
<213> ORGANISM: Artificial Sequence
<220> FEATURE:
<223> OTHER INFORMATION: Synthetic

<400> SEQUENCE: 51

Gly Ala Gly Gly Thr Gly Cys Ala Gly Cys Thr Gly Gly Thr Gly Gly
1               5                   10                  15

Ala Gly Thr Cys Cys Gly Gly Ala Gly Gly Ala Gly Gly Cys Cys Thr
            20                  25                  30

Gly Gly Thr Gly Cys Ala Ala Cys Cys Thr Gly Gly Ala Gly Gly Cys
        35                  40                  45

Thr Cys Cys Cys Thr Gly Ala Gly Gly Cys Thr Gly Thr Cys Cys Thr
50                  55                  60

Gly Thr Gly Cys Cys Gly Cys Thr Thr Cys Cys Gly Gly Cys Thr Thr
65                  70                  75                  80

Cys Ala Cys Cys Thr Thr Cys Ala Gly Cys Thr Cys Cys Thr Ala Cys
                85                  90                  95

Gly Ala Thr Ala Thr Gly Ala Gly Cys Thr Gly Gly Gly Thr Gly Ala
            100                 105                 110

Gly Gly Cys Ala Gly Gly Cys Thr Cys Cys Thr Gly Gly Ala Ala Ala
        115                 120                 125

Gly Gly Gly Cys Cys Thr Gly Gly Ala Gly Thr Gly Gly Gly Thr Gly
    130                 135                 140

Gly Cys Cys Ala Cys Ala Thr Cys Thr Cys Cys Gly Ala Cys Gly
145                 150                 155                 160

Gly Ala Gly Gly Cys Gly Gly Cys Thr Ala Cys Ala Thr Cys Thr Ala
                165                 170                 175

Cys Thr Ala Cys Thr Cys Cys Gly Ala Cys Thr Cys Cys Gly Thr Gly
            180                 185                 190

Ala Ala Gly Gly Gly Cys Ala Gly Gly Thr Thr Cys Ala Cys Cys Ala
        195                 200                 205

Thr Cys Thr Cys Cys Gly Gly Ala Cys Ala Ala Cys Gly Cys Cys
    210                 215                 220

Cys Ala Ala Gly Ala Ala Cys Ala Cys Cys Thr Gly Thr Ala Cys
225                 230                 235                 240

Cys Thr Gly Cys Ala Gly Ala Thr Gly Ala Ala Cys Thr Cys Thr Cys
                245                 250                 255

Thr Cys Ala Gly Gly Gly Cys Thr Gly Ala Gly Gly Ala Cys Ala Cys
            260                 265                 270

Cys Gly Cys Cys Gly Thr Gly Thr Ala Thr Ala Cys Thr Gly Cys
        275                 280                 285

Gly Cys Cys Ala Gly Gly Gly Ala Thr Thr Thr Gly Gly Cys Ala
    290                 295                 300

Ala Gly Ala Gly Gly Thr Ala Cys Gly Cys Cys Cys Thr Gly Gly Ala
305                 310                 315                 320
```

```
Thr Thr Ala Cys Thr Gly Gly Gly Gly Cys Ala Gly Gly Cys
                325                 330                 335

Ala Cys Ala Cys Thr Gly Gly Thr Gly Ala Cys Ala Gly Thr Gly Ala
                340                 345                 350

Gly Cys Thr Cys Cys
        355

<210> SEQ ID NO 52
<211> LENGTH: 357
<212> TYPE: PRT
<213> ORGANISM: Artificial Sequence
<220> FEATURE:
<223> OTHER INFORMATION: Synthetic

<400> SEQUENCE: 52

Gly Ala Gly Gly Thr Gly Cys Ala Gly Cys Thr Gly Gly Thr Gly Gly
1               5                   10                  15

Ala Gly Thr Cys Cys Gly Gly Ala Gly Gly Ala Gly Gly Cys Cys Thr
                20                  25                  30

Gly Gly Thr Gly Cys Ala Ala Cys Cys Thr Gly Gly Ala Gly Gly Cys
                35                  40                  45

Thr Cys Cys Cys Thr Gly Ala Gly Gly Cys Thr Gly Thr Cys Cys Thr
    50                  55                  60

Gly Thr Gly Cys Cys Gly Cys Thr Thr Cys Cys Gly Gly Cys Thr Thr
65                  70                  75                  80

Cys Ala Cys Cys Thr Thr Cys Ala Gly Cys Thr Cys Cys Thr Ala Cys
                85                  90                  95

Gly Ala Thr Ala Thr Gly Ala Gly Cys Thr Gly Gly Gly Thr Gly Ala
                100                 105                 110

Gly Gly Cys Ala Gly Ala Cys Cys Cys Cys Thr Gly Gly Ala Ala Ala
                115                 120                 125

Gly Ala Gly Cys Cys Thr Gly Gly Ala Gly Thr Gly Gly Gly Thr Gly
                130                 135                 140

Gly Cys Cys Ala Cys Ala Thr Cys Thr Cys Cys Gly Gly Ala Cys Gly
145                 150                 155                 160

Gly Ala Gly Gly Cys Gly Gly Cys Thr Ala Cys Ala Thr Cys Thr Ala
                165                 170                 175

Cys Thr Ala Cys Thr Cys Cys Gly Ala Cys Thr Cys Cys Gly Thr Gly
                180                 185                 190

Ala Ala Gly Gly Gly Cys Ala Gly Gly Thr Thr Cys Ala Cys Cys Ala
                195                 200                 205

Thr Cys Thr Cys Cys Cys Gly Gly Gly Ala Cys Ala Ala Cys Gly Cys
                210                 215                 220

Cys Ala Ala Gly Ala Ala Cys Ala Ala Cys Cys Thr Gly Thr Ala Cys
225                 230                 235                 240

Cys Thr Gly Cys Ala Gly Ala Thr Gly Ala Ala Cys Thr Cys Thr Cys
                245                 250                 255

Thr Cys Ala Gly Gly Gly Cys Thr Gly Ala Gly Gly Ala Cys Ala Cys
                260                 265                 270

Cys Gly Cys Cys Gly Thr Gly Thr Ala Thr Ala Cys Thr Gly Cys
                275                 280                 285

Gly Cys Cys Ala Gly Gly Gly Ala Thr Thr Thr Gly Gly Cys Ala
            290                 295                 300

Ala Gly Ala Gly Gly Thr Ala Cys Gly Cys Cys Cys Thr Gly Gly Ala
305                 310                 315                 320
```

```
Thr Thr Ala Cys Thr Gly Gly Gly Gly Cys Ala Gly Gly Cys
                325                 330                 335

Ala Cys Ala Cys Thr Gly Gly Thr Gly Ala Cys Ala Gly Thr Gly Ala
                340                 345                 350

Gly Cys Thr Cys Cys
        355

<210> SEQ ID NO 53
<211> LENGTH: 357
<212> TYPE: PRT
<213> ORGANISM: Artificial Sequence
<220> FEATURE:
<223> OTHER INFORMATION: Synthetic

<400> SEQUENCE: 53

Gly Ala Gly Gly Thr Gly Cys Ala Gly Cys Thr Gly Gly Thr Gly Gly
1               5                   10                  15

Ala Gly Thr Cys Cys Gly Gly Ala Gly Gly Ala Gly Gly Cys Cys Thr
                20                  25                  30

Gly Gly Thr Gly Cys Ala Ala Cys Cys Thr Gly Gly Ala Gly Gly Cys
                35                  40                  45

Thr Cys Cys Cys Thr Gly Ala Gly Gly Cys Thr Gly Thr Cys Cys Thr
50                  55                  60

Gly Thr Gly Cys Cys Gly Cys Thr Thr Cys Cys Gly Gly Cys Thr Thr
65                  70                  75                  80

Cys Ala Cys Cys Thr Thr Cys Ala Gly Cys Thr Cys Cys Thr Ala Cys
                85                  90                  95

Gly Ala Thr Ala Thr Gly Ala Gly Cys Thr Gly Gly Gly Thr Gly Ala
                100                 105                 110

Gly Gly Cys Ala Gly Gly Cys Thr Cys Cys Thr Gly Gly Ala Ala Ala
                115                 120                 125

Gly Gly Gly Cys Cys Thr Gly Gly Ala Gly Thr Gly Gly Gly Thr Gly
        130                 135                 140

Gly Cys Cys Ala Cys Cys Ala Thr Cys Thr Cys Gly Ala Cys Gly Gly
145                 150                 155                 160

Gly Ala Gly Gly Cys Gly Gly Cys Thr Ala Cys Ala Thr Cys Thr Ala
                165                 170                 175

Cys Thr Ala Cys Thr Cys Cys Gly Ala Cys Thr Cys Gly Thr Gly
                180                 185                 190

Ala Ala Gly Gly Gly Cys Ala Gly Gly Thr Thr Cys Ala Cys Cys Ala
                195                 200                 205

Thr Cys Thr Cys Cys Gly Gly Ala Cys Ala Ala Cys Gly Cys
                210                 215                 220

Cys Ala Ala Gly Ala Ala Cys Thr Cys Cys Thr Gly Thr Ala Cys
225                 230                 235                 240

Cys Thr Gly Cys Ala Gly Ala Thr Gly Ala Ala Cys Thr Cys Thr Cys
                245                 250                 255

Thr Cys Ala Gly Gly Cys Thr Gly Ala Gly Gly Ala Cys Ala Cys
                260                 265                 270

Cys Gly Cys Cys Gly Thr Gly Thr Ala Thr Cys Thr Gly Cys
        275                 280                 285

Gly Cys Cys Ala Gly Gly Gly Ala Thr Thr Thr Gly Gly Cys Ala
        290                 295                 300

Ala Gly Ala Gly Gly Thr Ala Cys Gly Cys Cys Cys Thr Gly Gly Ala
305                 310                 315                 320
```

```
Thr Thr Ala Cys Thr Gly Gly Gly Gly Cys Ala Gly Gly Cys
            325                 330                 335

Ala Cys Ala Ala Cys Cys Gly Thr Gly Ala Cys Ala Gly Thr Gly Ala
            340                 345                 350

Gly Cys Thr Cys Cys
            355

<210> SEQ ID NO 54
<211> LENGTH: 321
<212> TYPE: PRT
<213> ORGANISM: Artificial Sequence
<220> FEATURE:
<223> OTHER INFORMATION: Synthetic

<400> SEQUENCE: 54

Gly Ala Cys Ala Thr Cys Gly Thr Gly Ala Thr Gly Ala Cys Cys Cys
1               5                   10                  15

Ala Gly Ala Gly Cys Cys Ala Cys Ala Ala Gly Thr Thr Cys Ala Thr
                20                  25                  30

Gly Ala Gly Cys Ala Cys Cys Ala Cys Gly Thr Gly Gly Gly Cys
            35                  40                  45

Gly Ala Thr Ala Gly Gly Thr Gly Ala Gly Cys Ala Thr Cys Ala
            50                  55                  60

Gly Cys Thr Gly Cys Ala Ala Gly Gly Cys Cys Ala Gly Cys Cys Ala
65                  70                  75                  80

Gly Gly Ala Thr Gly Thr Gly Ala Cys Cys Cys Thr Gly Cys Cys
                85                  90                  95

Gly Thr Gly Gly Cys Cys Thr Gly Thr Ala Cys Cys Ala Gly Cys
            100                 105                 110

Ala Gly Ala Ala Gly Cys Cys Gly Gly Cys Cys Ala Gly Ala Gly
            115                 120                 125

Cys Cys Cys Cys Ala Ala Gly Cys Thr Gly Cys Thr Gly Ala Thr Cys
130                 135                 140

Thr Ala Cys Ala Gly Cys Ala Cys Cys Ala Gly Cys Ala Gly Cys Ala
145                 150                 155                 160

Gly Gly Thr Ala Cys Ala Cys Cys Gly Gly Cys Gly Thr Gly Cys Cys
                165                 170                 175

Cys Gly Ala Cys Ala Gly Gly Thr Thr Cys Ala Cys Gly Gly Ala
            180                 185                 190

Ala Gly Cys Gly Gly Cys Ala Gly Cys Gly Gly Cys Ala Cys Cys Gly
                195                 200                 205

Ala Cys Thr Thr Cys Ala Cys Cys Thr Thr Cys Ala Cys Cys Ala Thr
            210                 215                 220

Cys Ala Gly Cys Ala Gly Cys Cys Thr Gly Cys Ala Gly Cys Cys
225                 230                 235                 240

Gly Ala Gly Gly Ala Cys Cys Thr Gly Cys Cys Gly Thr Gly Thr
                245                 250                 255

Ala Cys Thr Ala Cys Thr Gly Cys Cys Ala Gly Cys Ala Gly Cys Ala
            260                 265                 270

Cys Thr Ala Cys Ala Cys Cys Ala Cys Cys Cys Thr Cys Thr Gly
            275                 280                 285

Ala Cys Cys Thr Thr Cys Gly Gly Cys Gly Gly Cys Ala
            290                 295                 300

Cys Cys Ala Ala Gly Cys Thr Gly Gly Ala Gly Cys Thr Gly Ala Ala
305                 310                 315                 320
```

-continued

Gly

<210> SEQ ID NO 55
<211> LENGTH: 321
<212> TYPE: PRT
<213> ORGANISM: Artificial Sequence
<220> FEATURE:
<223> OTHER INFORMATION: Synthetic

<400> SEQUENCE: 55

```
Gly Ala Cys Ala Thr Cys Cys Ala Gly Ala Thr Gly Ala Cys Cys Cys
1               5                   10                  15
Ala Gly Ala Gly Cys Cys Cys Thr Ala Gly Cys Ala Gly Cys Cys Thr
            20                  25                  30
Gly Ala Gly Cys Gly Cys Thr Ala Gly Cys Gly Thr Gly Gly Gly Cys
        35                  40                  45
Gly Ala Cys Ala Gly Gly Thr Gly Ala Cys Cys Ala Thr Cys Ala
    50                  55                  60
Cys Cys Thr Gly Cys Ala Ala Gly Gly Cys Cys Ala Gly Cys Cys Ala
65                  70                  75                  80
Gly Gly Ala Thr Gly Thr Gly Ala Cys Cys Cys Thr Gly Cys Cys
            85                  90                  95
Gly Thr Gly Gly Cys Cys Thr Gly Gly Thr Ala Cys Ala Gly Cys
            100                 105                 110
Ala Gly Ala Ala Gly Cys Cys Cys Gly Gly Cys Ala Ala Gly Gly Cys
        115                 120                 125
Cys Cys Cys Cys Ala Ala Gly Cys Thr Gly Cys Thr Gly Ala Thr Cys
130                 135                 140
Thr Ala Cys Ala Gly Cys Ala Cys Cys Ala Gly Cys Ala Gly Cys Ala
145                 150                 155                 160
Gly Gly Thr Ala Cys Ala Cys Cys Gly Gly Cys Gly Thr Gly Cys Cys
            165                 170                 175
Cys Ala Gly Cys Ala Gly Gly Thr Thr Thr Ala Gly Cys Gly Gly Ala
        180                 185                 190
Ala Gly Cys Gly Gly Cys Ala Gly Cys Gly Gly Cys Ala Cys Cys Gly
        195                 200                 205
Ala Cys Thr Thr Cys Ala Cys Cys Thr Cys Ala Cys Cys Ala Thr
        210                 215                 220
Cys Ala Gly Cys Ala Gly Cys Cys Thr Gly Cys Ala Gly Cys Cys Cys
225                 230                 235                 240
Gly Ala Gly Gly Ala Cys Ala Thr Cys Gly Cys Cys Ala Cys Thr
        245                 250                 255
Ala Cys Thr Ala Cys Thr Gly Cys Cys Ala Gly Cys Ala Gly Cys Ala
            260                 265                 270
Cys Thr Ala Cys Ala Cys Cys Ala Cys Cys Cys Thr Cys Thr Gly
        275                 280                 285
Ala Cys Cys Thr Thr Cys Gly Gly Cys Cys Ala Gly Gly Gly Cys Ala
            290                 295                 300
Cys Cys Ala Ala Gly Cys Thr Gly Gly Ala Gly Ala Thr Cys Ala Ala
305                 310                 315                 320
Gly
```

<210> SEQ ID NO 56
<211> LENGTH: 321
<212> TYPE: PRT
<213> ORGANISM: Artificial Sequence

```
<220> FEATURE:
<223> OTHER INFORMATION: Synthetic

<400> SEQUENCE: 56

Gly Ala Cys Ala Thr Cys Cys Ala Gly Ala Thr Gly Ala Cys Cys Cys
1               5                   10                  15

Ala Gly Ala Gly Cys Cys Cys Thr Ala Gly Cys Ala Gly Cys Cys Thr
            20                  25                  30

Gly Ala Gly Cys Gly Cys Thr Ala Gly Cys Gly Thr Gly Gly Gly Cys
            35                  40                  45

Gly Ala Cys Ala Gly Gly Thr Gly Ala Cys Cys Ala Thr Cys Ala
            50              55                  60

Cys Cys Thr Gly Cys Ala Ala Gly Gly Cys Cys Ala Gly Cys Cys Ala
65                  70                  75                  80

Gly Gly Ala Thr Gly Thr Gly Ala Cys Cys Cys Thr Gly Cys Cys
                85                  90                  95

Gly Thr Gly Gly Cys Cys Thr Gly Gly Thr Ala Cys Ala Gly Cys
            100                 105                 110

Ala Gly Ala Ala Gly Cys Cys Cys Gly Gly Cys Ala Ala Gly Thr Cys
            115                 120                 125

Cys Cys Cys Ala Ala Gly Cys Thr Gly Cys Thr Gly Ala Thr Cys Tyr
130                 135                 140

Thr Ala Cys Ala Gly Cys Ala Cys Cys Ala Gly Cys Ala Gly Cys Ala
145                 150                 155                 160

Gly Gly Thr Ala Cys Ala Cys Gly Gly Cys Gly Thr Gly Cys Cys Cys
                165                 170                 175

Cys Ala Gly Cys Ala Gly Gly Thr Thr Ala Gly Cys Gly Gly Ala
                180                 185                 190

Ala Gly Cys Gly Gly Cys Ala Gly Cys Gly Gly Cys Ala Cys Cys Gly
            195                 200                 205

Ala Cys Thr Thr Cys Ala

```
Ala Gly Thr Cys Cys Cys Thr Ala Gly Cys Ala Gly Cys Cys Thr
            20                  25                  30

Gly Thr Cys Cys Gly Cys Thr Thr Cys Cys Gly Thr Gly Gly Cys
            35                  40                  45

Gly Ala Cys Ala Gly Gly Thr Gly Ala Cys Cys Ala Thr Cys Ala
            50                  55                  60

Cys Cys Thr Gly Cys Ala Ala Gly Gly Cys Ala Gly Cys Cys Ala
65                  70                  75                  80

Gly Gly Ala Cys Gly Thr Gly Ala Cys Cys Thr Gly Cys Thr
            85                  90                  95

Gly Thr Gly Gly Cys Cys Thr Gly Thr Ala Thr Cys Ala Ala Cys
            100                 105                 110

Ala Gly Ala Ala Gly Cys Cys Thr Gly Cys Ala Ala Gly Gly Cys
            115                 120                 125

Th

Gly Ala Cys Ala Gly Gly Thr Gly Ala Cys Ala Thr Cys Ala
            50                  55                  60
Cys Cys Thr Gly Cys Ala Ala Gly Gly Cys Ala Gly Cys Cys Ala
65                  70                  75                  80
Gly Gly Ala Cys Gly Thr Gly Ala Cys Ala Cys Thr Gly Cys Thr
                85                  90                  95
Gly Thr Gly Gly Cys Cys Thr Gly Thr Ala Thr Cys Ala Ala Cys
                100                 105                 110
Ala Gly Ala Ala Gly Cys Cys Thr Gly Gly Cys Ala Ala Gly G

Gly Thr Gly Gly Cys Cys Thr Gly Thr Ala Thr Cys Ala Ala Cys
                85                  90                  95

Ala Gly Ala Ala Gly Cys Cys Thr Gly Gly Cys Cys Ala Gly Ala Gly
            100                 105                 110

Cys Cys Cys Thr Ala Ala Gly Cys Thr Cys Cys Thr Gly Ala Thr Cys
            115                 120                 125

Thr Ala Cys Ala Gly Cys Ala Cys Ala Thr Cys Cys Thr Cys Cys Cys
130                 135                 140

Gly Gly Thr Ala Cys Ala Cys Cys Gly Gly Ala Gly Thr Gly Cys Cys
145                 150                 155                 160

Cys Gly Ala Cys Ala Gly Gly Thr Thr Thr Ala Cys Cys Gly Gly Cys
            165                 170                 175

Ala Gly Cys Gly Gly Cys Thr Cys Cys Gly Gly Cys Ala Cys Cys Gly
            180                 185                 190

Ala Thr Thr Thr Cys Ala Cys Cys Cys Thr Gly Ala Cys Cys Ala Thr
            195                 200                 205

Thr Thr Cys Cys Thr Cys Cys Cys Thr Gly Cys Ala Gly Cys Cys Cys
225                 230                 235                 240

Gly Ala Gly Gly Ala Cys Thr Thr Cys Gly Cys Cys Ala Cys Cys Thr
            245                 250                 255

Ala Cys Thr Ala Cys Thr Gly Cys Cys Ala Gly Cys Ala Gly Cys Ala
            260                 265                 270

Cys Thr Ala Cys Ala Cys Cys Ala Cys Cys Cys Cys Cys Th

Cys Cys Cys Thr Ala Ala Gly Cys Thr Cys Thr Gly Ala Thr Cys
130                 135                 140

Thr Ala Cys Ala Gly Cys Ala Cys Ala Thr Cys Thr Cys Cys Cys
145                 150                 155                 160

Gly Gly Thr Ala Cys Ala Cys Cys Gly Ala Gly Thr Gly Cys Cys
                165                 170                 175

Cys Gly Ala Cys Ala Gly Gly Thr Thr Ala Cys Cys Gly Gly Cys
                180                 185                 190

Ala Gly Cys Gly Gly Cys Thr Cys Cys Gly Gly Cys Ala Cys Cys Gly
            195                 200                 205

Ala Thr Thr Thr Cys Ala Cys Cys Cys Thr Gly Ala Cys Cys Ala Thr
        210                 215                 220

Thr Thr Cys Cys Thr Cys Cys Cys Thr Gly Cys Ala Gly Cys Cys Cys
225                 230                 235                 240

Gly Ala Gly Gly Ala Cys Thr Thr Cys Gly Cys Cys Ala Cys Cys Thr
                245                 250                 255

Ala Cys Thr Ala Cys Thr Gly Cys Cys Ala Gly Cys Ala Gly Cys Ala
                260                 265                 270

Cys Thr Ala Cys Ala Cys Ala Cys Ala Cys Cys Cys Thr Gly
            275                 280                 285

Ala Cys Cys Thr Thr Cys Gly Gly Cys Cys Ala Gly Gly Gly Cys Ala
        290                 295                 300

Cys Cys Ala Ala Gly Cys Thr Gly Gly Ala Gly Ala Thr Cys Ala Ala
305                 310                 315                 320

Gly Cys Gly Gly

<210> SEQ ID NO 61
<211> LENGTH: 5
<212> TYPE: PRT
<213> ORGANISM: Artificial Sequence
<220> FEATURE:
<223> OTHER INFORMATION: Synthetic

<400> SEQUENCE: 61

Thr Tyr Asp Met Ser
1               5

<210> SEQ ID NO 62
<211> LENGTH: 5
<212> TYPE: PRT
<213> ORGANISM: Artificial Sequence
<220> FEATURE:
<223> OTHER INFORMATION: Synthetic

<400> SEQUENCE: 62

Cys Tyr Asp Met Ser
1               5

<210> SEQ ID NO 63
<211> LENGTH: 5
<212> TYPE: PRT
<213> ORGANISM: Artificial Sequence
<220> FEATURE:
<223> OTHER INFORMATION: Synthetic

<400> SEQUENCE: 63

Ser Phe Asp Met Ser
1               5

```
<210> SEQ ID NO 64
<211> LENGTH: 5
<212> TYPE: PRT
<213> ORGANISM: Artificial Sequence
<220> FEATURE:
<223> OTHER INFORMATION: Synthetic

<400> SEQUENCE: 64

Ser His Asp Met Ser
1               5

<210> SEQ ID NO 65
<211> LENGTH: 5
<212> TYPE: PRT
<213> ORGANISM: Artificial Sequence
<220> FEATURE:
<223> OTHER INFORMATION: Synthetic

<400> SEQUENCE: 65

Ser Trp Asp Met Ser
1               5

<210> SEQ ID NO 66
<211> LENGTH: 5
<212> TYPE: PRT
<213> ORGANISM: Artificial Sequence
<220> FEATURE:
<223> OTHER INFORMATION: Synthetic

<400> SEQUENCE: 66

Ser Tyr Asp Met Thr
1               5

<210> SEQ ID NO 67
<211> LENGTH: 5
<212> TYPE: PRT
<213> ORGANISM: Artificial Sequence
<220> FEATURE:
<223> OTHER INFORMATION: Synthetic

<400> SEQUENCE: 67

Ser Tyr Asp Met Cys
1               5

<210> SEQ ID NO 68
<211> LENGTH: 17
<212> TYPE: PRT
<213> ORGANISM: Artificial Sequence
<220> FEATURE:
<223> OTHER INFORMATION: Synthetic

<400> SEQUENCE: 68

Thr Ile Ser Asp Gly Gly Ala Tyr Ile Tyr Tyr Ser Asp Ser Val Lys
1               5                   10                  15

Gly

<210> SEQ ID NO 69
<211> LENGTH: 17
<212> TYPE: PRT
<213> ORGANISM: Artificial Sequence
<220> FEATURE:
<223> OTHER INFORMATION: Synthetic

<400> SEQUENCE: 69

Thr Ile Ser Asp Gly Gly Pro Tyr Ile Tyr Tyr Ser Asp Ser Val Lys
1               5                   10                  15
```

Gly

<210> SEQ ID NO 70
<211> LENGTH: 17
<212> TYPE: PRT
<213> ORGANISM: Artificial Sequence
<220> FEATURE:
<223> OTHER INFORMATION: Synthetic

<400> SEQUENCE: 70

Thr Ile Ser Asp Gly Gly Gly Phe Ile Tyr Tyr Ser Asp Ser Val Lys
1               5                   10                  15

Gly

<210> SEQ ID NO 71
<211> LENGTH: 17
<212> TYPE: PRT
<213> ORGANISM: Artificial Sequence
<220> FEATURE:
<223> OTHER INFORMATION: Synthetic

<400> SEQUENCE: 71

Thr Ile Ser Asp Gly Gly Gly His Ile Tyr Tyr Ser Asp Ser Val Lys
1               5                   10                  15

Gly

<210> SEQ ID NO 72
<211> LENGTH: 17
<212> TYPE: PRT
<213> ORGANISM: Artificial Sequence
<220> FEATURE:
<223> OTHER INFORMATION: Synthetic

<400> SEQUENCE: 72

Thr Ile Ser Asp Gly Gly Gly Trp Ile Tyr Tyr Ser Asp Ser Val Lys
1               5                   10                  15

Gly

<210> SEQ ID NO 73
<211> LENGTH: 17
<212> TYPE: PRT
<213> ORGANISM: Artificial Sequence
<220> FEATURE:
<223> OTHER INFORMATION: Synthetic

<400> SEQUENCE: 73

Thr Ile Ser Asp Gly Gly Gly Tyr Ile Tyr Tyr Ser Asp Thr Val Lys
1               5                   10                  15

Gly

<210> SEQ ID NO 74
<211> LENGTH: 17
<212> TYPE: PRT
<213> ORGANISM: Artificial Sequence
<220> FEATURE:
<223> OTHER INFORMATION: Synthetic

<400> SEQUENCE: 74

Thr Ile Ser Asp Gly Gly Gly Tyr Ile Tyr Tyr Ser Asp Cys Val Lys
1               5                   10                  15

Gly

<210> SEQ ID NO 75

```
<211> LENGTH: 17
<212> TYPE: PRT
<213> ORGANISM: Artificial Sequence
<220> FEATURE:
<223> OTHER INFORMATION: Synthetic

<400> SEQUENCE: 75

Thr Ile Ser Asp Gly Gly Gly Tyr Ile Tyr Tyr Ser Asp Ser Leu Lys
1               5                   10                  15

Gly

<210> SEQ ID NO 76
<211> LENGTH: 17
<212> TYPE: PRT
<213> ORGANISM: Artificial Sequence
<220> FEATURE:
<223> OTHER INFORMATION: Synthetic

<400> SEQUENCE: 76

Thr Ile Ser Asp Gly Gly Gly Tyr Ile Tyr Tyr Ser Asp Ser Ile Lys
1               5                   10                  15

Gly

<210> SEQ ID NO 77
<211> LENGTH: 17
<212> TYPE: PRT
<213> ORGANISM: Artificial Sequence
<220> FEATURE:
<223> OTHER INFORMATION: Synthetic

<400> SEQUENCE: 77

Thr Ile Ser Asp Gly Gly Gly Tyr Ile Tyr Tyr Ser Asp Ser Met Lys
1               5                   10                  15

Gly

<210> SEQ ID NO 78
<211> LENGTH: 10
<212> TYPE: PRT
<213> ORGANISM: Artificial Sequence
<220> FEATURE:
<223> OTHER INFORMATION: Synthetic

<400> SEQUENCE: 78

Gln Phe Gly Lys Arg Tyr Ala Leu Asp Tyr
1               5                   10

<210> SEQ ID NO 79
<211> LENGTH: 10
<212> TYPE: PRT
<213> ORGANISM: Artificial Sequence
<220> FEATURE:
<223> OTHER INFORMATION: Synthetic

<400> SEQUENCE: 79

Asp Phe Gly Lys Arg Tyr Ala Leu Asp Tyr
1               5                   10

<210> SEQ ID NO 80
<211> LENGTH: 10
<212> TYPE: PRT
<213> ORGANISM: Artificial Sequence
<220> FEATURE:
<223> OTHER INFORMATION: Synthetic

<400> SEQUENCE: 80
```

```
Asn Phe Gly Lys Arg Tyr Ala Leu Asp Tyr
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Synthetic

<400> SEQUENCE: 81

Glu Tyr Gly Lys Arg Tyr Ala Leu Asp Tyr
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Synthetic

<400> SEQUENCE: 82

Glu His Gly Lys Arg Tyr Ala Leu Asp Tyr
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Synthetic

<400> SEQUENCE: 83

Glu Trp Gly Lys Arg Tyr Ala Leu Asp Tyr
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Synthetic

<400> SEQUENCE: 84

Glu Phe Ala Lys Arg Tyr Ala Leu Asp Tyr
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Synthetic

<400> SEQUENCE: 85

Glu Phe Pro Lys Arg Tyr Ala Leu Asp Tyr
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Synthetic

<400> SEQUENCE: 86

Glu Phe Gly Arg Arg Tyr Ala Leu Asp Tyr
```

```
<210> SEQ ID NO 87
<211> LENGTH: 10
<212> TYPE: PRT
<213> ORGANISM: Artificial Sequence
<220> FEATURE:
<223> OTHER INFORMATION: Synthetic

<400> SEQUENCE: 87

Glu Phe Gly Lys Lys Tyr Ala Leu Asp Tyr
1               5                   10

<210> SEQ ID NO 88
<211> LENGTH: 10
<212> TYPE: PRT
<213> ORGANISM: Artificial Sequence
<220> FEATURE:
<223> OTHER INFORMATION: Synthetic

<400> SEQUENCE: 88

Glu Phe Gly Lys Arg Phe Ala Leu Asp Tyr
1               5                   10

<210> SEQ ID NO 89
<211> LENGTH: 10
<212> TYPE: PRT
<213> ORGANISM: Artificial Sequence
<220> FEATURE:
<223> OTHER INFORMATION: Synthetic

<400> SEQUENCE: 89

Glu Phe Gly Lys Arg His Ala Leu Asp Tyr
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Synthetic

<400> SEQUENCE: 90

Glu Phe Gly Lys Arg Trp Ala Leu Asp Tyr
1               5                   10

<210> SEQ ID NO 91
<211> LENGTH: 11
<212> TYPE: PRT
<213> ORGANISM: Artificial Sequence
<220> FEATURE:
<223> OTHER INFORMATION: Synthetic

<400> SEQUENCE: 91

Lys Ala Thr Gln Asp Val Thr Pro Ala Val Ala
1               5                   10

<210> SEQ ID NO 92
<211> LENGTH: 11
<212> TYPE: PRT
<213> ORGANISM: Artificial Sequence
<220> FEATURE:
<223> OTHER INFORMATION: Synthetic

<400> SEQUENCE: 92

Lys Ala Cys Gln Asp Val Thr Pro Ala Val Ala
1               5                   10
```

```
<210> SEQ ID NO 93
<211> LENGTH: 7
<212> TYPE: PRT
<213> ORGANISM: Artificial Sequence
<220> FEATURE:
<223> OTHER INFORMATION: Synthetic

<400> SEQUENCE: 93

Thr Thr Ser Ser Arg Tyr Thr
1               5

<210> SEQ ID NO 94
<211> LENGTH: 7
<212> TYPE: PRT
<213> ORGANISM: Artificial Sequence
<220> FEATURE:
<223> OTHER INFORMATION: Synthetic

<400> SEQUENCE: 94

Cys Thr Ser Ser Arg Tyr Thr
1               5

<210> SEQ ID NO 95
<211> LENGTH: 7
<212> TYPE: PRT
<213> ORGANISM: Artificial Sequence
<220> FEATURE:
<223> OTHER INFORMATION: Synthetic

<400> SEQUENCE: 95

Ser Ser Ser Ser Arg Tyr Thr
1               5

<210> SEQ ID NO 96
<211> LENGTH: 7
<212> TYPE: PRT
<213> ORGANISM: Artificial Sequence
<220> FEATURE:
<223> OTHER INFORMATION: Synthetic

<400> SEQUENCE: 96

Ser Met Ser Ser Arg Tyr Thr
1               5

<210> SEQ ID NO 97
<211> LENGTH: 7
<212> TYPE: PRT
<213> ORGANISM: Artificial Sequence
<220> FEATURE:
<223> OTHER INFORMATION: Synthetic

<400> SEQUENCE: 97

Ser Val Ser Ser Arg Tyr Thr
1               5

<210> SEQ ID NO 98
<211> LENGTH: 7
<212> TYPE: PRT
<213> ORGANISM: Artificial Sequence
<220> FEATURE:
<223> OTHER INFORMATION: Synthetic

<400> SEQUENCE: 98

Ser Thr Thr Ser Arg Tyr Thr
1               5
```

```
<210> SEQ ID NO 99
<211> LENGTH: 7
<212> TYPE: PRT
<213> ORGANISM: Artificial Sequence
<220> FEATURE:
<223> OTHER INFORMATION: Synthetic

<400> SEQUENCE: 99

Ser Thr Cys Ser Arg Tyr Thr
1               5

<210> SEQ ID NO 100
<211> LENGTH: 7
<212> TYPE: PRT
<213> ORGANISM: Artificial Sequence
<220> FEATURE:
<223> OTHER INFORMATION: Synthetic

<400> SEQUENCE: 100

Ser Thr Ser Thr Arg Tyr Thr
1               5

<210> SEQ ID NO 101
<211> LENGTH: 7
<212> TYPE: PRT
<213> ORGANISM: Artificial Sequence
<220> FEATURE:
<223> OTHER INFORMATION: Synthetic

<400> SEQUENCE: 101

Ser Thr Ser Cys Arg Tyr Thr
1               5

<210> SEQ ID NO 102
<211> LENGTH: 7
<212> TYPE: PRT
<213> ORGANISM: Artificial Sequence
<220> FEATURE:
<223> OTHER INFORMATION: Synthetic

<400> SEQUENCE: 102

Ser Thr Ser Ser Lys Tyr Thr
1               5

<210> SEQ ID NO 103
<211> LENGTH: 7
<212> TYPE: PRT
<213> ORGANISM: Artificial Sequence
<220> FEATURE:
<223> OTHER INFORMATION: Synthetic

<400> SEQUENCE: 103

Ser Thr Ser Ser Arg Phe Thr
1               5

<210> SEQ ID NO 104
<211> LENGTH: 7
<212> TYPE: PRT
<213> ORGANISM: Artificial Sequence
<220> FEATURE:
<223> OTHER INFORMATION: Synthetic

<400> SEQUENCE: 104

Ser Thr Ser Ser Arg His Thr
1               5
```

```
<210> SEQ ID NO 105
<211> LENGTH: 7
<212> TYPE: PRT
<213> ORGANISM: Artificial Sequence
<220> FEATURE:
<223> OTHER INFORMATION: Synthetic

<400> SEQUENCE: 105

Ser Thr Ser Ser Arg Trp Thr
1               5

<210> SEQ ID NO 106
<211> LENGTH: 9
<212> TYPE: PRT
<213> ORGANISM: Artificial Sequence
<220> FEATURE:
<223> OTHER INFORMATION: Synthetic

<400> SEQUENCE: 106

Glu Gln His Tyr Thr Thr Pro Leu Thr
1               5

<210> SEQ ID NO 107
<211> LENGTH: 9
<212> TYPE: PRT
<213> ORGANISM: Artificial Sequence
<220> FEATURE:
<223> OTHER INFORMATION: Synthetic

<400> SEQUENCE: 107

Asp Gln His Tyr Thr Thr Pro Leu Thr
1               5

<210> SEQ ID NO 108
<211> LENGTH: 9
<212> TYPE: PRT
<213> ORGANISM: Artificial Sequence
<220> FEATURE:
<223> OTHER INFORMATION: Synthetic

<400> SEQUENCE: 108

Asn Gln His Tyr Thr Thr Pro Leu Thr
1               5

<210> SEQ ID NO 109
<211> LENGTH: 9
<212> TYPE: PRT
<213> ORGANISM: Artificial Sequence
<220> FEATURE:
<223> OTHER INFORMATION: Synthetic

<400> SEQUENCE: 109

Gln Glu His Tyr Thr Thr Pro Leu Thr
1               5

<210> SEQ ID NO 110
<211> LENGTH: 9
<212> TYPE: PRT
<213> ORGANISM: Artificial Sequence
<220> FEATURE:
<223> OTHER INFORMATION: Synthetic

<400> SEQUENCE: 110

Gln Asp His Tyr Thr Thr Pro Leu Thr
1               5

<210> SEQ ID NO 111
```

```
<211> LENGTH: 9
<212> TYPE: PRT
<213> ORGANISM: Artificial Sequence
<220> FEATURE:
<223> OTHER INFORMATION: Synthetic

<400> SEQUENCE: 111

Gln Asn His Tyr Thr Thr Pro Leu Thr
1               5

<210> SEQ ID NO 112
<211> LENGTH: 357
<212> TYPE: PRT
<213> ORGANISM: Artificial Sequence
<220> FEATURE:
<223> OTHER INFORMATION: Synthetic

<400> SEQUENCE: 112

Gly Ala Ala Gly Thr Gly Ala Ala Cys Thr Gly Thr Gly Gly
1               5                   10                  15

Ala Gly Thr Cys Thr Gly Gly Gly Ala Gly Ala Cys Thr Thr
                20                  25                  30

Ala Gly Thr Gly Ala Ala Gly Cys Cys Thr Gly Ala Gly Gly
            35                  40                  45

Thr Cys Cys Cys Thr Gly Ala Ala Cys Thr Cys Thr Cys Thr
    50                  55                  60

Gly Thr Gly Cys Ala Gly Cys Cys Thr Cys Thr Gly Gly Ala Thr Thr
65                  70                  75                  80

Cys Ala Cys Thr Thr Thr Cys Ala Gly Thr Ala Gly Cys Thr Ala Thr
                85                  90                  95

Gly Ala Cys Ala Thr Gly Thr Cys Thr Thr Gly Gly Thr Thr Cys
                100                 105                 110

Gly Cys Cys Ala Gly Ala Cys Thr Cys Cys Gly Gly Ala Gly Ala Ala
            115                 120                 125

Gly Ala Gly Thr Cys Thr Gly Gly Ala Gly Thr Gly Gly Gly Thr Cys
        130                 135                 140

Gly Cys Ala Ala Cys Cys Ala Thr Thr Ala Gly Thr Gly Ala Thr Gly
145                 150                 155                 160

Gly Thr Gly Gly Thr Gly Gly Thr Thr Ala Cys Ala Cys Thr Thr Ala
                165                 170                 175

Cys Thr Ala Thr Thr Cys Ala Gly Ala Cys Ala Gly Thr Gly Thr Gly
                180                 185                 190

Ala Ala Gly Gly Gly Cys Gly Ala Thr Thr Thr Ala Cys Cys Ala
            195                 200                 205

Thr Cys Thr Cys Cys Ala Gly Ala Gly Ala Cys Ala Ala Thr Gly Cys
    210                 215                 220

Cys Ala Ala Gly Ala Ala Cys Ala Cys Cys Thr Gly Thr Ala Cys
225                 230                 235                 240

Cys Thr Gly Cys Ala Ala Ala Thr Gly Ala Gly Cys Ala Gly Thr Cys
                245                 250                 255

Thr Gly Ala Gly Gly Thr Cys Thr Gly Ala Gly Gly Ala Cys Ala Cys
                260                 265                 270

Gly Gly Cys Cys Thr Thr Gly Thr Ala Thr Thr Thr Gly Thr
        275                 280                 285

Gly Cys Ala Ala Gly Ala Gly Ala Ala Thr Thr Gly Gly Thr Ala
        290                 295                 300

Ala Gly Cys Gly Cys Thr Ala Thr Gly Cys Thr Thr Thr Gly Gly Ala
```

```
                305                 310                 315                 320
Cys Thr Ala Cys Thr Gly Gly Gly Thr Cys Ala Ala Gly Ala
                325                 330                 335

Ala Cys Cys Thr Cys Ala Gly Thr Cys Ala Cys Cys Gly Thr Cys Thr
                340                 345                 350

Cys Cys Thr Cys Ala
                355

<210> SEQ ID NO 113
<211> LENGTH: 116
<212> TYPE: PRT
<213> ORGANISM: Artificial Sequence
<220> FEATURE:
<223> OTHER INFORMATION: Synthetic

<400> SEQUENCE: 113

Glu Val Lys Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
                20                  25                  30

Asp Met Ser Trp Val Arg Gln Thr Pro Glu Lys Ser Leu Glu Trp Val
            35                  40                  45

Ala Thr Ile Ser Asp Gly Gly Tyr Ile Tyr Tyr Ser Asp Ser Val
        50                  55                  60

Lys Gly Arg Phe Thr Ile Ser Arg Asp Asn Ala Lys Asn Asn Leu Tyr
65                  70                  75                  80

Leu Gln Met Ser Ser Leu Arg Ser Glu Asp Thr Ala Leu Tyr Ile Cys
                85                  90                  95

Ala Arg Glu Phe Gly Lys Arg Tyr Ala Leu Asp Tyr Trp Gly Gln Gly
            100                 105                 110

Thr Ser Val Thr
        115

<210> SEQ ID NO 114
<211> LENGTH: 321
<212> TYPE: PRT
<213> ORGANISM: Artificial Sequence
<220> FEATURE:
<223> OTHER INFORMATION: Synthetic

<400> SEQUENCE: 114

Gly Ala Cys Ala Thr Thr Gly Thr Gly Ala Thr Gly Ala Cys Cys Cys
1               5                   10                  15

Ala Gly Thr Cys Thr Cys Ala Cys Ala Ala Thr Thr Cys Ala Thr
                20                  25                  30

Gly Thr Cys Cys Ala Cys Ala Thr Cys Gly Gly Thr Ala Gly Gly Ala
            35                  40                  45

Gly Ala Cys Ala Gly Gly Gly Thr Cys Ala Gly Cys Ala Thr Cys Thr
        50                  55                  60

Cys Cys Thr Gly Cys Ala Ala Gly Gly Cys Cys Ala Gly Thr Cys Ala
65                  70                  75                  80

Gly Gly Ala Thr Gly Thr Gly Ala Cys Thr Cys Thr Gly Cys Thr
                85                  90                  95

Gly Thr Cys Gly Cys Cys Thr Gly Gly Thr Ala Thr Cys Ala Ala Cys
            100                 105                 110

Ala Gly Ala Ala Gly Cys Cys Ala Gly Gly Ala Cys Ala Ala Thr Cys
        115                 120                 125
```

```
Thr Cys Cys Thr Ala Ala Ala Cys Thr Ala Cys Thr Gly Ala Thr Thr
    130                 135                 140
Thr Ala Cys Thr Cys Cys Ala Cys Ala Thr Cys Cys Thr Cys Cys Cys
145                 150                 155                 160
Gly Gly Thr Ala Cys Ala Cys Thr Gly Ala Gly Thr Cys Cys Cys
                165                 170                 175
Thr Gly Ala Thr Cys Gly Cys Thr Thr Cys Ala Cys Thr Gly Gly Cys
                180                 185                 190
Ala Gly Thr Gly Gly Ala Thr Cys Thr Gly Gly Gly Ala Cys Gly Gly
                195                 200                 205
Ala Thr Thr Thr Cys Ala Cys Thr Thr Cys Ala Cys Cys Ala Thr
            210                 215                 220
Cys Ala Gly Cys Ala Gly Thr Gly Thr Gly Cys Ala Gly Gly Cys Thr
225                 230                 235                 240
Gly Ala Ala Gly Ala Cys Cys Thr Gly Gly Cys Ala Gly Thr Thr Thr
                245                 250                 255
Ala Thr Thr Ala Cys Thr Gly Thr Cys Ala Gly Cys Ala Ala Cys Ala
            260                 265                 270
Thr Thr Ala Thr Ala Cys Thr Ala Cys Thr Cys Cys Gly Cys Thr Cys
            275                 280                 285
Ala Cys Gly Thr Thr Cys Gly Gly Thr Gly Cys Thr Gly Gly Gly Ala
290                 295                 300
Cys Cys Ala Ala Gly Cys Thr Gly Gly Ala Gly Cys Thr Gly Ala Ala
305                 310                 315                 320
Ala
```

```
<210> SEQ ID NO 115
<211> LENGTH: 107
<212> TYPE: PRT
<213> ORGANISM: Artificial Sequence
<220> FEATURE:
<223> OTHER INFORMATION: Synthetic

<400> SEQUENCE: 115

Asp Ile Val Met Thr Gln Ser His Lys Phe Met Ser Thr Ser Val Gly
1               5                   10                  15
Asp Arg Val Ser Ile Ser Cys Lys Ala Ser Gln Asp Val Thr Pro Ala
                20                  25                  30
Val Ala Trp Tyr Gln Gln Lys Pro Gly Gln Ser Pro Lys Leu Leu Ile
            35                  40                  45
Tyr Ser Thr Ser Ser Arg Tyr Thr Gly Val Pro Asp Arg Phe Thr Gly
    50                  55                  60
Ser Gly Ser Gly Thr Asp Phe Thr Phe Thr Ile Ser Ser Val Gln Ala
65                  70                  75                  80
Glu Asp Leu Ala Val Tyr Tyr Cys Gln Gln His Tyr Thr Thr Pro Leu
                85                  90                  95
Thr Phe Gly Ala Gly Thr Lys Leu Glu Leu Lys
                100                 105
```

ANTI-PD-L1 ANTIBODIES AND USES THEREOF

CROSS REFERENCE TO RELATED APPLICATIONS

The present application is a divisional application of U.S. application Ser. No. 15/744,737, filed Jan. 12, 2018, which is the U.S. national stage application of International Application PCT/CN2017/088033, filed Jun. 13, 2017, which claims priority to International Application PCT/CN2017/072566, filed Jan. 25, 2017 and Chinese Patent Application No. 201610414226.5, filed Jun. 13, 2016, the contents of which are incorporated herein by reference in their entireties in the present disclosure.

BACKGROUND

Programmed death-ligand 1 (PD-L1), also known as cluster of differentiation 274 (CD274) or B7 homolog 1 (B7-H1), is a 40 kDa type 1 transmembrane protein believed to play a major role in suppressing the immune system during particular events such as pregnancy, tissue allografts, autoimmune disease and other disease states such as hepatitis. The binding of PD-L1 to PD-1 or B7.1 transmits an inhibitory signal which reduces the proliferation of CD8+ T cells at the lymph nodes and supplementary to that PD-1 is also able to control the accumulation of foreign antigen specific T cells in the lymph nodes through apoptosis which is further mediated by a lower regulation of the gene Bcl-2.

It has been shown that upregulation of PD-L1 may allow cancers to evade the host immune system. An analysis of tumor specimens from patients with renal cell carcinoma found that high tumor expression of PD-L1 was associated with increased tumor aggressiveness and an increased risk of death. Many PD-L1 inhibitors are in development as immuno-oncology therapies and are showing good results in clinical trials.

In addition to treatment of cancers, PD-L1 inhibition has also shown promises in treating infectious diseases. In a mouse model of intracellular infection, *L. monocytogenes* induced PD-L1 protein expression in T cells, NK cells, and macrophages. PD-L1 blockade (e.g., using blocking antibodies) resulted in increased mortality for infected mice. Blockade reduced TNFα and nitric oxide production by macrophages, reduced granzyme B production by NK cells, and decreased proliferation of *L. monocytogenes* antigen-specific CD8 T cells (but not CD4 T cells). This evidence suggests that PD-L1 acts as a positive costimulatory molecule in intracellular infection.

SUMMARY

The present disclosure provides anti-PD-L1 antibody having high binding affinity to human PD-L1 proteins and can effectively block the interaction between PD-L1 and its receptor PD-1. Also importantly, the examples demonstrate that these anti-PD-L1 antibodies promote T cell immune response and inhibit tumor growth. Different from known anti-PD-L1 antibodies that bind to the immunoglobulin V domain of the extracellular portion of the PD-L1 protein, these antibodies bind to the immunoglobulin C domain, in particular amino acid residues Y134, K162, and N183. These anti-PD-L1 antibodies are useful for therapeutic purposes such as treating various types of cancer, as well as infections, and can also be used for diagnostic and prognostic purposes.

One embodiment of the present disclosure provides an anti-PD-L1 antibody or fragment thereof, which antibody or fragment thereof can specifically bind to an immunoglobulin C (Ig C) domain of a human Programmed death-ligand 1 (PD-L1) protein. In some embodiments, the Ig C domain consists of amino acid residues 133-225. In some embodiments, the antibody or fragment thereof can bind to at least one of amino acid residues Y134, K162, or N183 of the PD-L1 protein. In some embodiments, the antibody or fragment thereof can bind to at least one of amino acid residues Y134, K162, and N183 of the PD-L1 protein. In some embodiments, the antibody or fragment thereof does not bind to an immunoglobulin V (Ig V) domain of the PD-L1 protein, wherein the Ig V domain consists of amino acid residues 19-127.

One embodiment of the present disclosure provides an anti-PD-L1 antibody or fragment thereof, wherein the antibody or fragment thereof has specificity to a human Programmed death-ligand 1 (PD-L1) protein and comprises a VH CDR1 of SEQ ID NO: 1, a VH CDR2 of SEQ ID NO: 2, a VH CDR3 of SEQ ID NO: 3, a VL CDR1 of SEQ ID NO: 4, a VL CDR2 of SEQ ID NO: 5, and a VL CDR3 of SEQ ID NO: 6. In some embodiments, the antibody or fragment thereof further comprises a heavy chain constant region, a light chain constant region, an Fc region, or the combination thereof. In some embodiments, the light chain constant region is a kappa or lambda chain constant region. In some embodiments, the antibody or fragment thereof is of an isotype of IgG, IgM, IgA, IgE or IgD. In some embodiments, the isotype is IgG1, IgG2, IgG3 or IgG4. Without limitation, the antibody or fragment thereof is a chimeric antibody, a humanized antibody, or a fully human antibody. In one aspect, antibody or fragment thereof is a humanized antibody.

In some embodiments, the antibody or fragment thereof comprises a heavy chain variable region comprising one or more amino acid residues selected from the group consisting of (a) Ser at position 44, (b) Ala at position 49, (c) Ala at position 53, (d) Ile at position 91, (e) Glu at position 1, (f) Val at position 37, (g) Thr at position 40 (h) Val at position 53, (i) Glu at position 54, (j) Asn at position 77, (k) Arg at position 94, and (l) Thr at position 108, according to Kabat numbering, and combinations thereof. In some embodiments, the antibody or fragment thereof comprises a heavy chain variable region comprising (a) Ser at position 44, (b) Ala at position 49, (c) Ala at position 53, and/or (d) Ile at position 91, according to Kabat numbering, and combinations thereof.

In some embodiments, the antibody or fragment thereof comprises a light chain variable region comprising one or more amino acid residues selected from the group consisting of: (a) Ser at position 22, (b) Gln at position 42, (c) Ser at position 43, (d) Asp at position 60, and (e) Thr at position 63, according to Kabat numbering, and combinations thereof.

Non-limiting examples of antibody or fragment thereof include those having a heavy chain variable region comprising an amino acid sequence selected from the group consisting of SEQ ID NO: 7-26, or a peptide having at least 90% sequence identity to an amino acid sequence selected from the group consisting of SEQ ID NO: 7-26. Non-limiting examples of antibody or fragment thereof include those having a light chain variable region comprising an amino acid sequence selected from the group consisting of SEQ ID NO: 27-33, or a peptide having at least 90% sequence identity to an amino acid sequence selected from the group consisting of SEQ ID NO: 27-33. Non-limiting examples of antibody or fragment thereof include those having a heavy chain variable region comprising the amino acid sequence of SEQ ID NO: 20 and a light chain variable region comprising the amino acid sequence of SEQ ID NO: 28.

Biologically equivalent variants of the antibodies and fragments thereof are also described. In some embodiments, provided is an isolated antibody or fragment thereof, wherein the antibody or fragment thereof has specificity to a human PD-L1 protein and comprises: (a) a VH CDR1 of SEQ ID NO: 1, or a variant of SEQ ID NO: 1 having a single substitution, deletion or insertion at location 1, 2 or 5 of SEQ ID NO: 1; (b) a VH CDR2 of SEQ ID NO: 2, or a variant of SEQ ID NO: 2 having a single substitution, deletion or insertion at location 7, 8, 14 or 15 of SEQ ID NO: 2; (c) a VH CDR3 of SEQ ID NO: 3, or a variant of SEQ ID NO: 3 having a single substitution, deletion or insertion at location 1, 2, 3, 4, 5 or 6 of SEQ ID NO: 3; (d) a VL CDR1 of SEQ ID NO: 4, or a variant of SEQ ID NO: 4 having a single substitution, deletion or insertion at location 3 of SEQ ID NO: 4; (e) a VL CDR2 of SEQ ID NO: 5, or a variant of SEQ ID NO: 5 having a single substitution, deletion or insertion at location 1, 2, 3, 4, 5 or 6 of SEQ ID NO: 5 and (f) a VL CDR3 of SEQ ID NO: 6, or a variant of SEQ ID NO: 6 having a single substitution, deletion or insertion at location 11 or 2 of SEQ ID NO: 6.

In some embodiments, the variant of SEQ ID NO: 1 is selected from the group consisting of SEQ ID NO: 61-67. In some embodiments, the variant of SEQ ID NO: 2 is selected from the group consisting of SEQ ID NO: 68-77. In some embodiments, the variant of SEQ ID NO: 3 is selected from the group consisting of SEQ ID NO: 78-90. In some embodiments, the variant of SEQ ID NO: 4 is selected from the group consisting of SEQ ID NO: 91-92. In some embodiments, the variant of SEQ ID NO: 5 is selected from the group consisting of SEQ ID NO: 93-105. In some embodiments, the variant of SEQ ID NO: 6 is selected from the group consisting of SEQ ID NO: 106-111.

In some embodiments, the antibody or fragment thereof comprises a heavy chain variable region comprising one or more amino acid residues selected from the group consisting of: (a) Ser at position 44, (b) Ala at position 49, (c) Ala at position 53, (d) Ile at position 91, (e) Glu at position 1, (f) Val at position 37, (g) Thr at position 40 (h) Val at position 53, (i) Glu at position 54, (j) Asn at position 77, (k) Arg at position 94, and (l) Thr at position 108, according to Kabat numbering, and combinations thereof. In some embodiments, the antibody or fragment thereof comprises a heavy chain variable region comprising (a) Ser at position 44, (b) Ala at position 49, (c) Ala at position 53, and/or (d) Ile at position 91, according to Kabat numbering, and combinations thereof.

In some embodiments, the antibody or fragment thereof comprises a light chain variable region comprising one or more amino acid residues selected from the group consisting of: (a) Ser at position 22, (b) Gln at position 42, (c) Ser at position 43, (d) Asp at position 60, and (e) Thr at position 63, according to Kabat numbering, and combinations thereof.

Also provided, in some embodiments, is a composition comprising the antibody or fragment thereof of the present disclosure and a pharmaceutically acceptable carrier. Still also provided, in some embodiments, is an isolated cell comprising one or more polynucleotide encoding the antibody or fragment thereof of the present disclosure.

Treatment methods and uses are also provided. In one embodiment, a method of treating cancer or infection in a patient in need thereof is provided, comprising administering to the patient an effective amount of the antibody or fragment thereof of the present disclosure. In some embodiments, the cancer is a solid tumor. In some embodiments, the cancer is selected from the group consisting of bladder cancer, liver cancer, colon cancer, rectal cancer, endometrial cancer, leukemia, lymphoma, pancreatic cancer, small cell lung cancer, non-small cell lung cancer, breast cancer, urethral cancer, head and neck cancer, gastrointestinal cancer, stomach cancer, oesophageal cancer, ovarian cancer, renal cancer, melanoma, prostate cancer and thyroid cancer. In some embodiments, the cancer is selected from the group consisting of bladder cancer, liver cancer, pancreatic cancer, non-small cell lung cancer, breast cancer, urethral cancer, colorectal cancer, head and neck cancer, squamous cell cancer, Merkel cell carcinoma, gastrointestinal cancer, stomach cancer, oesophageal cancer, ovarian cancer, renal cancer, and small cell lung cancer. In some embodiments, the method further comprises administering to the patient a second cancer therapeutic agent. In some embodiments, the infection is viral infection, bacterial infection, fungal infection or infection by a parasite.

In another embodiment, a method of treating cancer or infection in a patient in need thereof is provided, comprising: (a) treating a cell, in vitro, with the antibody or fragment thereof of the present disclosure; and (b) administering the treated cell to the patient. In some embodiments, the method further comprises, prior to step (a), isolating the cell from an individual. In some embodiments, the cell is isolated from the patient. In some embodiments, the cell is isolated from a donor individual different from the patient. In some embodiments, the cell is a T cell, non-limiting examples of which include a tumor-infiltrating T lymphocyte, a CD4+ T cell, a CD8+ T cell, or the combination thereof.

Diagnostic methods and uses are also provided. In one embodiment, a method of detecting expression of PD-L1 in a sample is provided, comprising contacting the sample with an antibody or fragment thereof under conditions for the antibody or fragment thereof to bind to the PD-L1, and detecting the binding which indicates expression of PD-L1 in the sample. In some embodiments, the sample comprises a tumor cell, a tumor tissue, an infected tissue, or a blood sample.

Antibodies and fragment of the present disclosure can be used to prepare bispecific antibodies. In one embodiment, an isolated bispecific antibody is provided, comprising a fragment of the present disclosure and a second antigen-binding fragment having specificity to a molecular on an immune cell. In some embodiments, the molecule is selected from the group consisting of PD-1, CTLA-4, LAG-3, CD28, CD122, 4-1BB, TIM3, OX-40, OX40L, CD40, CD40L, LIGHT, ICOS, ICOSL, GITR, GITRL, TIGIT, CD27, VISTA, B7H3, B7H4, HEVM or BTLA, CD47 and CD73. In some embodiments, the fragment and the second fragment each is independently selected from a Fab fragment, a single-chain variable fragment (scFv), or a single-domain antibody. In some embodiments, the bispecific antibody further comprises a Fc fragment.

DETAILED DESCRIPTION

Definitions

Figure 1:
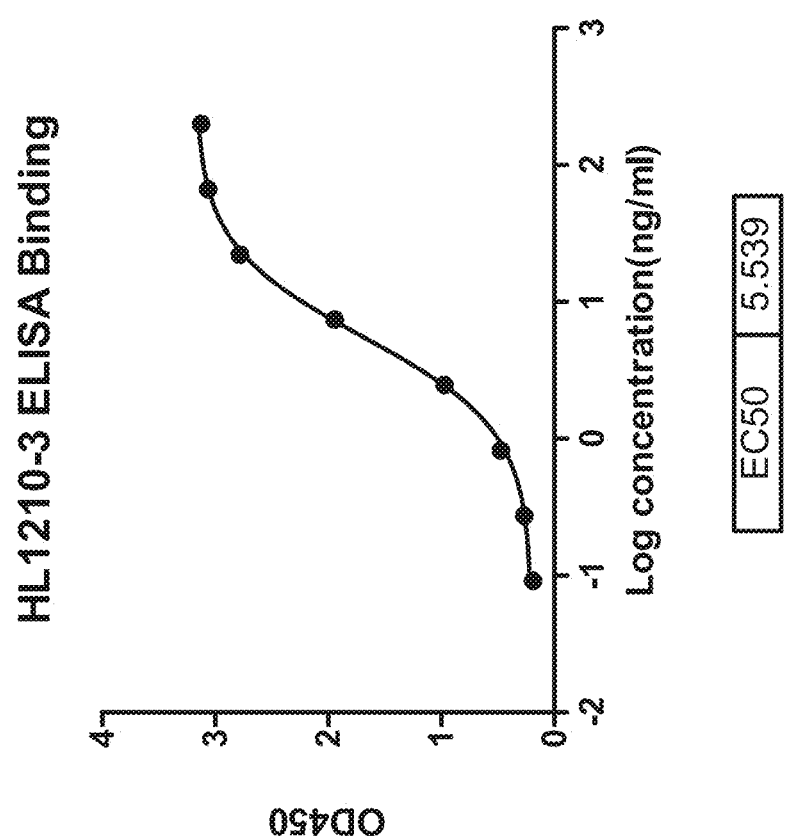
FIG. 1 shows that HL1210-3 can bind to human PD-L1 with high affinity.

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

The term "isolated" as used herein with respect to cells, nucleic acids, such as DNA or RNA, refers to molecules separated from other DNAs or RNAs, respectively, that are present in the natural source of the macromolecule. The term "isolated" as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to cells or polypeptides which are isolated from other cellular proteins or tissues. Isolated polypeptides is meant to encompass both purified and recombinant polypeptides.

As used herein, the term "recombinant" as it pertains to polypeptides or polynucleotides intends a form of the polypeptide or polynucleotide that does not exist naturally, a non-limiting example of which can be created by combining polynucleotides or polypeptides that would not normally occur together.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present disclosure.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Biologically equivalent polynucleotides are those having the above-noted specified percent homology and encoding a polypeptide having the same or similar biological activity.

The term "an equivalent nucleic acid or polynucleotide" refers to a nucleic acid having a nucleotide sequence having a certain degree of homology, or sequence identity, with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof. Likewise, "an equivalent polypeptide" refers to a polypeptide having a certain degree of homology, or sequence identity, with the amino acid sequence of a reference polypeptide. In some aspects, the sequence identity is at least about 70%, 75%, 80%, 85%, 90%, 95%, 98%, or 99%. In some aspects, the equivalent polypeptide or polynucleotide has one, two, three, four or five addition, deletion, substitution and their combinations thereof as compared to the reference polypeptide or polynucleotide. In some aspects, the equivalent sequence retains the activity (e.g., epitope-binding) or structure (e.g., salt-bridge) of the reference sequence.

Hybridization reactions can be performed under conditions of different "stringency". In general, a low stringency hybridization reaction is carried out at about 40° C. in about 10×SSC or a solution of equivalent ionic strength/temperature. A moderate stringency hybridization is typically performed at about 50° C. in about 6×SSC, and a high stringency hybridization reaction is generally performed at about 60° C. in about 1×SSC. Hybridization reactions can also be performed under "physiological conditions" which is well known to one of skill in the art. A non-limiting example of a physiological condition is the temperature, ionic strength, pH and concentration of $Mg^{2+}$ normally found in a cell.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching. The term "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, dsRNA, siRNA, miRNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this disclosure that is a polynucleotide encompasses both the double-stranded form and each of two complementary single-stranded forms known or predicted to make up the double-stranded form.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

As used herein, an "antibody" or "antigen-binding polypeptide" refers to a polypeptide or a polypeptide complex that specifically recognizes and binds to an antigen. An antibody can be a whole antibody and any antigen binding fragment or a single chain thereof. Thus the term "antibody" includes any protein or peptide containing molecule that comprises at least a portion of an immunoglobulin molecule having biological activity of binding to the antigen. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The terms "antibody fragment" or "antigen-binding fragment", as used herein, is a portion of an antibody such as $F(ab')_2$, $F(ab)_2$, Fab', Fab, Fv, scFv and the like. Regardless of structure, an antibody fragment binds with the same antigen that is recognized by the intact antibody. The term "antibody fragment" includes aptamers, spiegelmers, and diabodies. The term "antibody fragment" also includes any synthetic or genetically engineered protein that acts like an antibody by binding to a specific antigen to form a complex.

A "single-chain variable fragment" or "scFv" refers to a fusion protein of the variable regions of the heavy ($V_H$) and light chains ($V_L$) of immunoglobulins. In some aspects, the regions are connected with a short linker peptide of ten to about 25 amino acids. The linker can be rich in glycine for flexibility, as well as serine or threonine for solubility, and can either connect the N-terminus of the $V_H$ with the C-terminus of the $V_L$, or vice versa. This protein retains the specificity of the original immunoglobulin, despite removal of the constant regions and the introduction of the linker. ScFv molecules are known in the art and are described, e.g., in U.S. Pat. No. 5,892,019.

The term antibody encompasses various broad classes of polypeptides that can be distinguished biochemically. Those skilled in the art will appreciate that heavy chains are classified as gamma, mu, alpha, delta, or epsilon ($\gamma$, $\mu$, $\alpha$, $\delta$, $\epsilon$) with some subclasses among them (e.g., $\gamma 1$-$\gamma 4$). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgG_5$, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are clearly within the scope of the present disclosure, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Antibodies, antigen-binding polypeptides, variants, or derivatives thereof of the disclosure include, but are not limited to, polyclonal, monoclonal, multispecific, human, humanized, primatized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a VK or VH domain, fragments produced by a Fab expression library, and anti-idiotypic (anti-Id) antibodies (including, e.g., anti-Id antibodies to LIGHT antibodies disclosed herein). Immunoglobulin or antibody molecules of the disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Light chains are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VK) and heavy (VH) chain portions determine antigen recognition and specificity. Conversely, the constant domains of the light chain (CK) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CK domains actually comprise the carboxy-terminus of the heavy and light chain, respectively.

As indicated above, the variable region allows the antibody to selectively recognize and specifically bind epitopes on antigens. That is, the VK domain and VH domain, or subset of the complementarity determining regions (CDRs), of an antibody combine to form the variable region that defines a three dimensional antigen-binding site. This quaternary antibody structure forms the antigen-binding site present at the end of each arm of the Y. More specifically, the antigen-binding site is defined by three CDRs on each of the VH and VK chains (i.e. CDR-H1, CDR-H2, CDR-H3, CDR-L1, CDR-L2 and CDR-L3). In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., *Nature* 363:446-448 (1993).

In naturally occurring antibodies, the six "complementarity determining regions" or "CDRs" present in each antigen-binding domain are short, non-contiguous sequences of amino acids that are specifically positioned to form the antigen-binding domain as the antibody assumes its three dimensional configuration in an aqueous environment. The remainder of the amino acids in the antigen-binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see "Sequences of Proteins of Immunological Interest," Kabat, E., et al., U.S. Department of Health and Human Services, (1983); and Chothia and Lesk, *J. Mol. Biol.*, 196:901-917 (1987)).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., *J. Mol. Biol.* 196:901-917 (1987), which are incorporated herein by reference in their entireties. The CDR definitions according to Kabat and Chothia include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth in the table below as a comparison. The exact residue numbers which encompass a particular CDR will vary depending on the sequence and size of the CDR. Those skilled in the art can routinely determine which residues comprise a particular CDR given the variable region amino acid sequence of the antibody.

|         | Kabat  | Chothia |
|---------|--------|---------|
| CDR-H1  | 31-35  | 26-32   |
| CDR-H2  | 50-65  | 52-58   |
| CDR-H3  | 95-102 | 95-102  |
| CDR-L1  | 24-34  | 26-32   |
| CDR-L2  | 50-56  | 50-52   |
| CDR-L3  | 89-97  | 91-96   |

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983).

In addition to table above, the Kabat number system describes the CDR regions as follows: CDR-H1 begins at approximately amino acid 31 (i.e., approximately 9 residues after the first cysteine residue), includes approximately 5-7 amino acids, and ends at the next tryptophan residue. CDR-H2 begins at the fifteenth residue after the end of CDR-H1, includes approximately 16-19 amino acids, and ends at the next arginine or lysine residue. CDR-H3 begins at approximately the thirty third amino acid residue after the end of CDR-H2; includes 3-25 amino acids; and ends at the sequence W-G-X-G, where X is any amino acid. CDR-L1 begins at approximately residue 24 (i.e., following a cysteine residue); includes approximately 10-17 residues; and ends at the next tryptophan residue. CDR-L2 begins at approximately the sixteenth residue after the end of CDR-L1 and includes approximately 7 residues. CDR-L3 begins at approximately the thirty third residue after the end of CDR-L2 (i.e., following a cysteine residue); includes approximately 7-11 residues and ends at the sequence F or W-G-X-G, where X is any amino acid.

Antibodies disclosed herein may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks).

As used herein, the term "heavy chain constant region" includes amino acid sequences derived from an immunoglobulin heavy chain. A polypeptide comprising a heavy chain constant region comprises at least one of: a CH1 domain, a hinge (e.g., upper, middle, and/or lower hinge region) domain, a CH2 domain, a CH3 domain, or a variant or fragment thereof. For example, an antigen-binding polypeptide for use in the disclosure may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the disclosure comprises a polypeptide chain comprising a CH3 domain. Further, an antibody for use in the disclosure may lack at least a portion of a CH2 domain (e.g., all or part of a CH2 domain). As set forth above, it will be understood by one of ordinary skill in the art that the heavy chain constant region may be modified such that they vary in amino acid sequence from the naturally occurring immunoglobulin molecule.

The heavy chain constant region of an antibody disclosed herein may be derived from different immunoglobulin molecules. For example, a heavy chain constant region of a polypeptide may comprise a CH1 domain derived from an $IgG_1$ molecule and a hinge region derived from an $IgG_3$ molecule. In another example, a heavy chain constant region can comprise a hinge region derived, in part, from an $IgG_1$ molecule and, in part, from an $IgG_3$ molecule. In another example, a heavy chain portion can comprise a chimeric hinge derived, in part, from an $IgG_1$ molecule and, in part, from an $IgG_4$ molecule.

As used herein, the term "light chain constant region" includes amino acid sequences derived from antibody light chain. Preferably, the light chain constant region comprises at least one of a constant kappa domain or constant lambda domain.

A "light chain-heavy chain pair" refers to the collection of a light chain and heavy chain that can form a dimer through a disulfide bond between the CL domain of the light chain and the CH1 domain of the heavy chain.

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat et al., U.S. Dept. of Health and Human Services, "Sequences of Proteins of Immunological Interest" (1983). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains (Roux et al., *J. Immunol* 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CK regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which may be intact, partial or modified in accordance with the instant disclosure) is obtained from a second species. In certain embodiments the target binding region or site will be from a non-human source (e.g. mouse or primate) and the constant region is human.

As used herein, "percent humanization" is calculated by determining the number of framework amino acid differences (i.e., non-CDR difference) between the humanized domain and the germline domain, subtracting that number from the total number of amino acids, and then dividing that by the total number of amino acids and multiplying by 100.

By "specifically binds" or "has specificity to," it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

As used herein, the terms "treat" or "treatment" refer to both therapeutic treatment and prophylactic or preventative measures, wherein the object is to prevent or slow down (lessen) an undesired physiological change or disorder, such as the progression of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sport, or pet animals such as dogs, cats, guinea pigs, rabbits, rats, mice, horses, cattle, cows, and so on.

As used herein, phrases such as "to a patient in need of treatment" or "a subject in need of treatment" includes subjects, such as mammalian subjects, that would benefit from administration of an antibody or composition of the present disclosure used, e.g., for detection, for a diagnostic procedure and/or for treatment.

Anti-PD-L1 Antibodies

The present disclosure provides anti-PD-L1 antibodies with high affinity to the human PD-L1 protein. The tested antibodies exhibited potent binding and inhibitory activities and are useful for therapeutic and diagnostics uses.

The PD-L1 protein is a 40 kDa type 1 transmembrane protein. Its extracellular portion includes an N-terminal immunoglobulin V (IgV) domain (amino acids 19-127) and a C-terminal immunoglobulin C (IgC) domain (amino acids 133-225). PD-1 and PD-L1 interact through the conserved front and side of their IgV domains, as do the IgV domains of antibodies and T cell receptors. Not surprisingly, the current anti-PD-L1 antibodies all bind to the IgV domain which can disrupt the binding between PD-1 and PD-L1. It is therefore a surprising and unexpected finding of the present disclosure that antibodies, such as many disclosed herein, that bind to the IgC domain of the PD-L1 protein can still effectively, and perhaps even more so, inhibit PD-L1, leading to even further improved therapeutic effects.

One embodiment of the present disclosure, therefore, provides an anti-PD-L1 antibody or fragment thereof, which antibody or fragment thereof can specifically bind to an immunoglobulin C (Ig C) domain of a human Programmed death-ligand 1 (PD-L1) protein. In some embodiments, the Ig C domain consists of amino acid residues 133-225.

In some embodiments, the antibody or fragment thereof can bind to at least one of amino acid residues Y134, K162, or N183 of the PD-L1 protein. In some embodiments, the antibody or fragment thereof can bind to at least two of amino acid residues Y134, K162, or N183 of the PD-L1 protein. In some embodiments, the antibody or fragment thereof can bind to at least one of amino acid residues Y134, K162, and N183 of the PD-L1 protein. In some embodiments, the antibody or fragment thereof does not bind to an immunoglobulin V (Ig V) domain of the PD-L1 protein, wherein the Ig V domain consists of amino acid residues 19-127.

In accordance with one embodiment of the present disclosure, provided is an antibody that includes the heavy chain and light chain variable domains with the CDR regions as defined in SEQ ID NO: 1-6.

TABLE 1

Sequences of the CDR regions

| Name | Sequence | SEQ ID NO: |
|---|---|---|
| VH CDR1 | S<u>Y</u>DM<u>S</u> | 1 |
| VH CDR2 | TISDGG<u>G</u>YIYYSD<u>S</u>VKG | 2 |
| VH CDR3 | E<u>F</u>G<u>KR</u>YALDY | 3 |
| VL CDR1 | KA<u>S</u>QDVTPAVA | 4 |
| VL CDR2 | S<u>TSSR</u>YT | 5 |
| VL CDR3 | <u>QQ</u>HYTTPLT | 6 |

As demonstrated in the experimental examples, the antibodies that contained these CDR regions, whether mouse, humanized or chimeric, had potent PD-L1 binding and inhibitory activities. Further computer modeling indicated that certain residues within the CDR can be modified to retain or improve the property of the antibodies. Such residues are referred to as "hot spots" which are underlined in Table 1. In some embodiments, an anti-PD-L1 antibody of the present disclosure includes the VH and VL CDR as listed in Table 1, with one, two or three further modifications. Such modifications can be addition, deletion or substation of amino acids.

In some embodiments, the modification is substitution at no more than one hot spot position from each of the CDRs. In some embodiments, the modification is substitution at one, two or three such hot spot positions. In one embodiment, the modification is substitution at one of the hot spot positions. Such substitutions, in some embodiments, are conservative substitutions.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Non-limiting examples of conservative amino acid substitutions are provided in the table below, where a similarity score of 0 or higher indicates conservative substitution between the two amino acids.

TABLE 2

Amino Acid Similarity Matrix

|   | C | G | P | S | A | T | D | E | N | Q | H | K | R | V | M | I | L | F | Y | W |
|---|---|---|---|---|---|---|---|---|---|---|---|---|---|---|---|---|---|---|---|---|
| W | −8 | −7 | −6 | −2 | −6 | −5 | −7 | −7 | −4 | −5 | −3 | −3 | 2 | −6 | −4 | −5 | −2 | 0 | 0 | 17 |
| Y | 0 | −5 | −5 | −3 | −3 | −3 | −4 | −4 | −2 | −4 | 0 | −4 | −5 | −2 | −2 | −1 | −1 | 7 | 10 | |
| F | −4 | −5 | −5 | −3 | −4 | −3 | −6 | −5 | −4 | −5 | −2 | −5 | −4 | −1 | 0 | 1 | 2 | 9 | | |
| L | −6 | −4 | −3 | −3 | −2 | −2 | −4 | −3 | −3 | −2 | −2 | −3 | −3 | 2 | 4 | 2 | 6 | | | |
| I | −2 | −3 | −2 | −1 | −1 | 0 | −2 | −2 | −2 | −2 | −2 | −2 | −2 | 4 | 2 | 5 | | | | |
| M | −5 | −3 | −2 | −2 | −1 | −1 | −3 | −2 | 0 | −1 | −2 | 0 | 0 | 2 | 6 | | | | | |
| V | −2 | −1 | −1 | −1 | 0 | 0 | −2 | −2 | −2 | −2 | −2 | −2 | −2 | 4 | | | | | | |
| R | −4 | −3 | 0 | 0 | −2 | −1 | −1 | −1 | 0 | 1 | 2 | 3 | 6 | | | | | | | |
| K | −5 | −2 | −1 | 0 | −1 | 0 | 0 | 0 | 1 | 1 | 0 | 5 | | | | | | | | |
| H | −3 | −2 | 0 | −1 | −1 | −1 | 1 | 1 | 2 | 3 | 6 | | | | | | | | | |
| Q | −5 | −1 | 0 | −1 | 0 | −1 | 2 | 2 | 1 | 4 | | | | | | | | | | |
| N | −4 | 0 | −1 | 1 | 0 | 0 | 2 | 1 | 2 | | | | | | | | | | | |
| E | −5 | 0 | −1 | 0 | 0 | 0 | 3 | 4 | | | | | | | | | | | | |
| D | −5 | 1 | −1 | 0 | 0 | 0 | 4 | | | | | | | | | | | | | |
| T | −2 | 0 | 0 | 1 | 1 | 3 | | | | | | | | | | | | | | |
| A | −2 | 1 | 1 | 1 | 2 | | | | | | | | | | | | | | | |
| S | 0 | 1 | 1 | 1 | | | | | | | | | | | | | | | | |
| P | −3 | −1 | 6 | | | | | | | | | | | | | | | | | |
| G | −3 | 5 | | | | | | | | | | | | | | | | | | |
| C | 12 | | | | | | | | | | | | | | | | | | | |

TABLE 3

Conservative Amino Acid Substitutions

| For Amino Acid | Substitution With |
|---|---|
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr, L-Ser, D-Ser |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S-Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

Specific examples of CDRs with suitable substitutions are provided in SEQ ID NO: 61-111 of Example 11. In some embodiments, therefore, an antibody of the present disclosure includes a VH CDR1 of SEQ ID NO: 1 or any one of 61-67. In some embodiments, an antibody of the present disclosure includes a VH CDR2 of SEQ ID NO: 2 or any one of 68-77. In some embodiments, an antibody of the present disclosure includes a VH CDR3 of SEQ ID NO: 1 or any one of 78-90. In some embodiments, an antibody of the present disclosure includes a VL CDR1 of SEQ ID NO: 4 or any one of 91-92. In some embodiments, an antibody of the present disclosure includes a VL CDR2 of SEQ ID NO: 5 or any one of 93-105. In some embodiments, an antibody of the present disclosure includes a VL CDR3 of SEQ ID NO: 6 or any one of 106-110.

In some embodiments, an antibody or fragment thereof includes no more than one, no more than two, or no more than three of the above substitutions. In some embodiments, the antibody or fragment thereof includes a VH CDR1 of SEQ ID NO: 1 or any one of SEQ ID NO: 61-67, a VH CDR2 of SEQ ID NO: 2, a VH CDR3 of SEQ ID NO: 3, a VL CDR1 of SEQ ID NO: 4, a VL CDR2 of SEQ ID NO: 5, and a VL CDR3 of SEQ ID NO: 6.

In some embodiments, the antibody or fragment thereof includes a VH CDR1 of SEQ ID NO: 1, a VH CDR2 of SEQ ID NO: 2 or any one of SEQ ID NO: 68-77, a VH CDR3 of SEQ ID NO: 3, a VL CDR1 of SEQ ID NO: 4, a VL CDR2 of SEQ ID NO: 5, and a VL CDR3 of SEQ ID NO: 6.

In some embodiments, the antibody or fragment thereof includes a VH CDR1 of SEQ ID NO: 1, a VH CDR2 of SEQ ID NO: 2, a VH CDR3 of SEQ ID NO: 3 or any one of SEQ ID NO: 78-90, a VL CDR1 of SEQ ID NO: 4, a VL CDR2 of SEQ ID NO: 5, and a VL CDR3 of SEQ ID NO: 6.

In some embodiments, the antibody or fragment thereof includes a VH CDR1 of SEQ ID NO: 1, a VH CDR2 of SEQ ID NO: 2, a VH CDR3 of SEQ ID NO: 3, a VL CDR1 of SEQ ID NO: 4 or any one of SEQ ID NO: 91-92, a VL CDR2 of SEQ ID NO: 5, and a VL CDR3 of SEQ ID NO: 6.

In some embodiments, the antibody or fragment thereof includes a VH CDR1 of SEQ ID NO: 1, a VH CDR2 of SEQ ID NO: 2, a VH CDR3 of SEQ ID NO: 3, a VL CDR1 of SEQ ID NO: 4, a VL CDR2 of SEQ ID NO: 5 or any one of SEQ ID NO: 93-105, and a VL CDR3 of SEQ ID NO: 6.

In some embodiments, the antibody or fragment thereof includes a VH CDR1 of SEQ ID NO: 1, a VH CDR2 of SEQ ID NO: 2, a VH CDR3 of SEQ ID NO: 3, a VL CDR1 of SEQ ID NO: 4, a VL CDR2 of SEQ ID NO: 5, and a VL CDR3 of SEQ ID NO: 6 or any one of SEQ ID NO: 106-111.

Non-limiting examples of VH are provided in SEQ ID NO: 7-26 and 113, out of which SEQ ID NO: 113 is the mouse VH, and SEQ ID NO: 7-26 are humanized ones. Further, among the humanized VH, SEQ ID NO: 9-15, 17-21 and 23-26 include one or more back-mutations to the mouse version. Likewise, non-limiting examples of VL (VK) are provided in SEQ ID NO: 27-33. SEQ ID NO: 28 and 30 are the originally derived, CDR-grafted, humanized sequences as shown in the examples. SEQ ID NO: 29 and 31-33 are humanized VL with back-mutations.

The back-mutations are shown to be useful for retaining certain characteristics of the anti-PD-L1 antibodies. Accordingly, in some embodiments, the anti-PD-L1 antibodies of the present disclosure, in particular the human or humanized ones, include one or more of the back-mutations. In some embodiments, the VH back-mutation (i.e., included amino acid at the specified position) is one or more selected from (a) Ser at position 44, (b) Ala at position 49, (c) Ala at position 53, (d) Ile at position 91, (e) Glu at position 1, (f) Val at position 37, (g) Thr at position 40 (h) Val at position 53, (i) Glu at position 54, (j) Asn at position 77, (k) Arg at position 94, and (1) Thr at position 108, according to Kabat numbering, and combinations thereof. In some embodiments, the back-mutations are selected from (a) Ser at position 44, (b) Ala at position 49, (c) Ala at position 53, and/or (d) Ile at position 91, according to Kabat numbering, and combinations thereof.

In some embodiments, the VL back-mutation is one or more selected from (a) Ser at position 22, (b) Gln at position 42, (c) Ser at position 43, (d) Asp at position 60, and (e) Thr at position 63, according to Kabat numbering, and combinations thereof.

In some embodiments, the anti-PD-L1 antibody of the present disclosure includes a VH of SEQ ID NO: 7-26, a VL of SEQ ID NO: 27-33, or their respective biological equivalents. A biological equivalent of a VH or VL is a sequence that includes the designated amino acids while having an overall 80%, 85%, 90%, 95%, 98% or 99% sequence identity. A biological equivalent of SEQ ID NO: 20, for instance, can be a VH that has an overall 80%, 85%, 90%, 95%, 98% or 99% sequence identity to SEQ ID NO: 20 but retains the CDRs (SEQ ID NO: 1-6 or their variants), and optionally retains one or more, or all of the back-mutations. In one embodiment, the VH has the amino acid sequence of SEQ ID NO: 20 and the VL has the amino acid sequence of SEQ ID NO: 28.

It will also be understood by one of ordinary skill in the art that antibodies as disclosed herein may be modified such that they vary in amino acid sequence from the naturally occurring binding polypeptide from which they were derived. For example, a polypeptide or amino acid sequence derived from a designated protein may be similar, e.g., have a certain percent identity to the starting sequence, e.g., it may be 60%, 70%, 75%, 80%, 85%, 90%, 95%, 98%, or 99% identical to the starting sequence.

In certain embodiments, the antibody comprises an amino acid sequence or one or more moieties not normally associated with an antibody. Exemplary modifications are described in more detail below. For example, an antibody of the disclosure may comprise a flexible linker sequence, or may be modified to add a functional moiety (e.g., PEG, a drug, a toxin, or a label).

Antibodies, variants, or derivatives thereof of the disclosure include derivatives that are modified, i.e., by the covalent attachment of any type of molecule to the antibody such that covalent attachment does not prevent the antibody from binding to the epitope. For example, but not by way of limitation, the antibodies can be modified, e.g., by glycosylation, acetylation, pegylation, phosphorylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the antibodies may contain one or more non-classical amino acids.

In some embodiments, the antibodies may be conjugated to therapeutic agents, prodrugs, peptides, proteins, enzymes, viruses, lipids, biological response modifiers, pharmaceutical agents, or PEG.

The antibodies may be conjugated or fused to a therapeutic agent, which may include detectable labels such as radioactive labels, an immunomodulator, a hormone, an enzyme, an oligonucleotide, a photoactive therapeutic or diagnostic agent, a cytotoxic agent, which may be a drug or a toxin, an ultrasound enhancing agent, a non-radioactive label, a combination thereof and other such agents known in the art.

The antibodies can be detectably labeled by coupling it to a chemiluminescent compound. The presence of the chemiluminescent-tagged antigen-binding polypeptide is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

The antibodies can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA). Techniques for conjugating various moieties to an antibody are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. (1985); Hellstrom et al., "Antibodies For Drug Delivery", in Controlled Drug Delivery (2nd Ed.), Robinson et al., (eds.), Marcel Dekker, Inc., pp. 623-53 (1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), Academic Press pp. 303-16 (1985), and Thorpe et al., "The Preparation And Cytotoxic Properties Of Antibody-Toxin Conjugates", *Immunol. Rev.* (52:119-58 (1982)).

Bi-Functional Molecules

PD-L1 is an immune checkpoint molecule and is also a tumor antigen. As a tumor antigen targeting molecule, an antibody or antigen-binding fragment specific to PD-L1 can be combined with a second antigen-binding fragment specific to an immune cell to generate a bispecific antibody.

In some embodiments, the immune cell is selected from the group consisting of a T cell, a B cell, a monocyte, a macrophage, a neutrophil, a dendritic cell, a phagocyte, a natural killer cell, an eosinophil, a basophil, and a mast cell. Molecules on the immune cell which can be targeted include, for example, CD3, CD16, CD19, CD28, and CD64. Other examples include PD-1, CTLA-4, LAG-3 (also known as CD223), CD28, CD122, 4-1BB (also known as CD137), TIM3, OX-40 or OX40L, CD40 or CD40L, LIGHT, ICOS/ICOSL, GITR/GITRL, TIGIT, CD27, VISTA, B7H3, B7H4, HEVM or BTLA (also known as CD272), killer-cell immunoglobulin-like receptors (KIRs), and CD47. Specific examples of bispecificity include, without limitation, PD-L1/PD-1, PD-L1/LAG3, PD-L1/TIGIT, and PD-L1/CD47.

As an immune checkpoint inhibitor, an antibody or antigen-binding fragment specific to PD-L1 can be combined with a second antigen-binding fragment specific to a tumor antigen to generate a bispecific antibody. A "tumor antigen" is an antigenic substance produced in tumor cells, i.e., it triggers an immune response in the host. Tumor antigens are useful in identifying tumor cells and are potential candidates for use in cancer therapy. Normal proteins in the body are not antigenic. Certain proteins, however, are produced or overexpressed during tumorigenesis and thus appear "foreign" to the body. This may include normal proteins that are well sequestered from the immune system, proteins that are normally produced in extremely small quantities, proteins that are normally produced only in certain stages of development, or proteins whose structure is modified due to mutation.

An abundance of tumor antigens are known in the art and new tumor antigens can be readily identified by screening. Non-limiting examples of tumor antigens include EGFR, Her2, EpCAM, CD20, CD30, CD33, CD47, CD52, CD133, CD73, CEA, gpA33, Mucins, TAG-72, CIX, PSMA, folate-binding protein, GD2, GD3, GM2, VEGF, VEGFR, Integrin, αVβ3, α5β1, ERBB2, ERBB3, MET, IGF1R, EPHA3, TRAILR1, TRAILR2, RANKL, FAP and Tenascin.

In some aspects, the monovalent unit has specificity to a protein that is overexpressed on a tumor cell as compared to a corresponding non-tumor cell. A "corresponding non-tumor cell" as used here, refers to a non-tumor cell that is of the same cell type as the origin of the tumor cell. It is noted that such proteins are not necessarily different from tumor antigens. Non-limiting examples include carcinoembryonic antigen (CEA), which is overexpressed in most colon, rectum, breast, lung, pancreas and gastrointestinal tract carcinomas; heregulin receptors (HER-2, neu or c-erbB-2), which is frequently overexpressed in breast, ovarian, colon, lung, prostate and cervical cancers; epidermal growth factor receptor (EGFR), which is highly expressed in a range of solid tumors including those of the breast, head and neck, non-small cell lung and prostate; asialoglycoprotein receptor; transferrin receptor; serpin enzyme complex receptor, which is expressed on hepatocytes; fibroblast growth factor receptor (FGFR), which is overexpressed on pancreatic ductal adenocarcinoma cells; vascular endothelial growth factor receptor (VEGFR), for anti-angiogenesis gene therapy; folate receptor, which is selectively overexpressed in 90% of nonmucinous ovarian carcinomas; cell surface glycocalyx; carbohydrate receptors; and polymeric immunoglobulin receptor, which is useful for gene delivery to respiratory epithelial cells and attractive for treatment of lung diseases such as Cystic Fibrosis. Non-limiting examples of bispecificity in this respect include PD-L1/EGFR, PD-L1/Her2, PD-L1/CD33, PD-L1/CD133, PD-L1/CEA and PD-L1/VEGF.

Different format of bispecific antibodies are also provided. In some embodiments, each of the anti-PD-L1 fragment and the second fragment each is independently selected from a Fab fragment, a single-chain variable fragment (scFv), or a single-domain antibody. In some embodiments, the bispecific antibody further includes a Fc fragment.

Bifunctional molecules that include not just antibody or antigen binding fragment are also provided. As a tumor antigen targeting molecule, an antibody or antigen-binding fragment specific to PD-L1, such as those described here, can be combined with an immune cytokine or ligand optionally through a peptide linker. The linked immune cytokines or ligands include, but not limited to, IL-2, IL-3, IL-4, IL-5, IL-6, IL-7, IL-10, IL-12, IL-13, IL-15, GM-CSF, TNF-α, CD40L, OX40L, CD27L, CD30L, 4-1BBL, LIGHT and GITRL. Such bi-functional molecules can combine the immune checkpoint blocking effect with tumor site local immune modulation.

Polynucleotides Encoding the Antibodies and Methods of Preparing the Antibodies

The present disclosure also provides isolated polynucleotides or nucleic acid molecules (e.g., SEQ ID NO: 34-60, 112, and 114) encoding the antibodies, variants or derivatives thereof of the disclosure. The polynucleotides of the present disclosure may encode the entire heavy and light chain variable regions of the antigen-binding polypeptides, variants or derivatives thereof on the same polynucleotide molecule or on separate polynucleotide molecules. Additionally, the polynucleotides of the present disclosure may encode portions of the heavy and light chain variable regions of the antigen-binding polypeptides, variants or derivatives thereof on the same polynucleotide molecule or on separate polynucleotide molecules.

Methods of making antibodies are well known in the art and described herein. In certain embodiments, both the variable and constant regions of the antigen-binding polypeptides of the present disclosure are fully human. Fully human antibodies can be made using techniques described in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140 which are incorporated by reference in their entireties.

In certain embodiments, the prepared antibodies will not elicit a deleterious immune response in the animal to be treated, e.g., in a human. In one embodiment, antigen-binding polypeptides, variants, or derivatives thereof of the disclosure are modified to reduce their immunogenicity using art-recognized techniques. For example, antibodies can be humanized, primatized, deimmunized, or chimeric antibodies can be made. These types of antibodies are derived from a non-human antibody, typically a murine or primate antibody, that retains or substantially retains the antigen-binding properties of the parent antibody, but which is less immunogenic in humans. This may be achieved by various methods, including (a) grafting the entire non-human variable domains onto human constant regions to generate chimeric antibodies; (b) grafting at least a part of one or more of the non-human complementarity determining regions (CDRs) into a human framework and constant regions with or without retention of critical framework residues; or (c) transplanting the entire non-human variable domains, but "cloaking" them with a human-like section by replacement of surface residues. Such methods are disclosed in Morrison et al., *Proc. Natl. Acad. Sci. USA* 57:6851-6855 (1984); Morrison et al., *Adv. Immunol.* 44:65-92 (1988); Verhoeyen et al., *Science* 239:1534-1536 (1988); Padlan, *Molec. Immun.* 25:489-498 (1991); Padlan, *Molec. Immun.* 31:169-217 (1994), and U.S. Pat. Nos. 5,585,089, 5,693,761, 5,693,762, and 6,190,370, all of which are hereby incorporated by reference in their entirety.

De-immunization can also be used to decrease the immunogenicity of an antibody. As used herein, the term "de-immunization" includes alteration of an antibody to modify T-cell epitopes (see, e.g., International Application Publication Nos.: WO/9852976 A1 and WO/0034317 A2). For example, variable heavy chain and variable light chain sequences from the starting antibody are analyzed and a human T-cell epitope "map" from each V region showing the location of epitopes in relation to complementarity-determining regions (CDRs) and other key residues within the sequence is created. Individual T-cell epitopes from the T-cell epitope map are analyzed in order to identify alternative amino acid substitutions with a low risk of altering activity of the final antibody. A range of alternative variable heavy and variable light sequences are designed comprising combinations of amino acid substitutions and these sequences are subsequently incorporated into a range of binding polypeptides. Typically, between 12 and 24 variant antibodies are generated and tested for binding and/or function. Complete heavy and light chain genes comprising modified variable and human constant regions are then cloned into expression vectors and the subsequent plasmids introduced into cell lines for the production of whole antibody. The antibodies are then compared in appropriate biochemical and biological assays, and the optimal variant is identified.

The binding specificity of antigen-binding polypeptides of the present disclosure can be determined by in vitro assays such as immunoprecipitation, radioimmunoassay (RIA) or enzyme-linked immunoabsorbent assay (ELISA).

Alternatively, techniques described for the production of single-chain units (U.S. Pat. No. 4,694,778; Bird, *Science* 242:423-442 (1988); Huston et al., *Proc. Natl. Acad. Sci. USA* 55:5879-5883 (1988); and Ward et al., *Nature* 334:544-554 (1989)) can be adapted to produce single-chain units of the present disclosure. Single-chain units are formed by linking the heavy and light chain fragments of the Fv region via an amino acid bridge, resulting in a single-chain fusion peptide. Techniques for the assembly of functional Fv fragments in *E. coli* may also be used (Skerra et al., *Science* 242: 1038-1041 (1988)).

Examples of techniques which can be used to produce single-chain Fvs (scFvs) and antibodies include those described in U.S. Pat. Nos. 4,946,778 and 5,258,498; Huston et al., *Methods in Enzymology* 203:46-88 (1991); Shu et al., *Proc. Natl. Sci. USA* 90:1995-1999 (1993); and Skerra et al., *Science* 240:1038-1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See, e.g., Morrison, *Science* 229:1202 (1985); Oi et al., *BioTechniques* 4:214 (1986); Gillies et al., *J. Immunol. Methods* 125:191-202 (1989); U.S. Pat. Nos. 5,807,715; 4,816,567; and 4,816397, which are incorporated herein by reference in their entireties.

Humanized antibodies are antibody molecules derived from a non-human species antibody that bind the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen-binding. These framework substitutions are identified by methods well known in the art, e.g., by modeling of the interactions of the CDR and framework residues to identify framework residues important for antigen-binding and sequence comparison to identify unusual framework residues at particular positions. (See, e.g., Queen et al., U.S. Pat. No. 5,585,089; Riechmann et al., *Nature* 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, *Molecular Immunology* 28(4/5):489-498 (1991); Studnicka et al., *Protein Engineering* 7(6):805-814 (1994); Roguska. et al., *Proc. Natl. Sci. USA* 91:969-973 (1994)), and chain shuffling (U.S. Pat. No. 5,565,332, which is incorporated by reference in its entirety).

Completely human antibodies are particularly desirable for therapeutic treatment of human patients. Human antibodies can be made by a variety of methods known in the art including phage display methods using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a desired target polypeptide. Monoclonal antibodies directed against the antigen can be obtained from the immunized, transgenic mice using conventional hybridoma technology. The human immunoglobulin transgenes harbored by the transgenic mice rearrange during B-cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar *Int. Rev. Immunol.* 73:65-93 (1995). For a detailed discussion of this technology for producing human antibodies and human monoclonal antibodies and protocols for producing such antibodies, see, e.g., PCT publications WO 98/24893; WO 96/34096; WO 96/33735; U.S. Pat. Nos. 5,413,923; 5,625,126; 5,633,425; 5,569,825; 5,661,016; 5,545,806; 5,814,318; and 5,939,598, which are incorporated by reference herein in their entirety. In addition, companies such as Abgenix, Inc. (Freemont, Calif.) and GenPharm (San Jose, Calif.) can be engaged to provide human antibodies directed against a selected antigen using technology similar to that described above.

Completely human antibodies which recognize a selected epitope can also be generated using a technique referred to as "guided selection." In this approach a selected non-human monoclonal antibody, e.g., a mouse antibody, is used to guide the selection of a completely human antibody recognizing the same epitope. (Jespers et al., *Bio/Technology*

72:899-903 (1988). See also, U.S. Pat. No. 5,565,332, which is incorporated by reference in its entirety.)

In another embodiment, DNA encoding desired monoclonal antibodies may be readily isolated and sequenced using conventional procedures (e.g., by using oligonucleotide probes that are capable of binding specifically to genes encoding the heavy and light chains of murine antibodies). The isolated and subcloned hybridoma cells serve as a preferred source of such DNA. Once isolated, the DNA may be placed into expression vectors, which are then transfected into prokaryotic or eukaryotic host cells such as E. coli cells, simian COS cells, Chinese Hamster Ovary (CHO) cells or myeloma cells that do not otherwise produce immunoglobulins. More particularly, the isolated DNA (which may be synthetic as described herein) may be used to clone constant and variable region sequences for the manufacture antibodies as described in Newman et al., U.S. Pat. No. 5,658,570, filed Jan. 25, 1995, which is incorporated by reference herein. Essentially, this entails extraction of RNA from the selected cells, conversion to cDNA, and amplification by PCR using Ig specific primers. Suitable primers for this purpose are also described in U.S. Pat. No. 5,658,570. As will be discussed in more detail below, transformed cells expressing the desired antibody may be grown up in relatively large quantities to provide clinical and commercial supplies of the immunoglobulin.

Additionally, using routine recombinant DNA techniques, one or more of the CDRs of the antigen-binding polypeptides of the present disclosure, may be inserted within framework regions, e.g., into human framework regions to humanize a non-human antibody. The framework regions may be naturally occurring or consensus framework regions, and preferably human framework regions (see, e.g., Chothia et al., J. Mol. Biol. 278:457-479 (1998) for a listing of human framework regions). Preferably, the polynucleotide generated by the combination of the framework regions and CDRs encodes an antibody that specifically binds to at least one epitope of a desired polypeptide, e.g., LIGHT. Preferably, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present disclosure and within the skill of the art.

In addition, techniques developed for the production of "chimeric antibodies" (Morrison et al., Proc. Natl. Acad. Sci. USA: 851-855 (1984); Neuberger et al., Nature 372:604-608 (1984); Takeda et al., Nature 314:452-454 (1985)) by splicing genes from a mouse antibody molecule, of appropriate antigen specificity, together with genes from a human antibody molecule of appropriate biological activity can be used. As used herein, a chimeric antibody is a molecule in which different portions are derived from different animal species, such as those having a variable region derived from a murine monoclonal antibody and a human immunoglobulin constant region.

Yet another highly efficient means for generating recombinant antibodies is disclosed by Newman, Biotechnology 10: 1455-1460 (1992). Specifically, this technique results in the generation of primatized antibodies that contain monkey variable domains and human constant sequences. This reference is incorporated by reference in its entirety herein. Moreover, this technique is also described in commonly assigned U.S. Pat. Nos. 5,658,570, 5,693,780 and 5,756,096 each of which is incorporated herein by reference.

Alternatively, antibody-producing cell lines may be selected and cultured using techniques well known to the skilled artisan. Such techniques are described in a variety of laboratory manuals and primary publications. In this respect, techniques suitable for use in the disclosure as described below are described in Current Protocols in Immunology, Coligan et al., Eds., Green Publishing Associates and Wiley-Interscience, John Wiley and Sons, New York (1991) which is herein incorporated by reference in its entirety, including supplements.

Additionally, standard techniques known to those of skill in the art can be used to introduce mutations in the nucleotide sequence encoding an antibody of the present disclosure, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference variable heavy chain region, CDR-H1, CDR-H2, CDR-H3, variable light chain region, CDR-L1, CDR-L2, or CDR-L3. Alternatively, mutations can be introduced randomly along all or part of the coding sequence, such as by saturation mutagenesis, and the resultant mutants can be screened for biological activity to identify mutants that retain activity.

Cancer Treatment

As described herein, the antibodies, variants or derivatives of the present disclosure may be used in certain treatment and diagnostic methods.

The present disclosure is further directed to antibody-based therapies which involve administering the antibodies of the disclosure to a patient such as an animal, a mammal, and a human for treating one or more of the disorders or conditions described herein. Therapeutic compounds of the disclosure include, but are not limited to, antibodies of the disclosure (including variants and derivatives thereof as described herein) and nucleic acids or polynucleotides encoding antibodies of the disclosure (including variants and derivatives thereof as described herein).

The antibodies of the disclosure can also be used to treat or inhibit cancer. PD-L1 can be overexpressed in tumor cells. Tumor-derived PD-L1 can bind to PD-1 on immune cells thereby limiting antitumor T-cell immunity. Results with small molecule inhibitors, or monoclonal antibodies targeting PD-L1 in murine tumor models, indicate that targeted PD-L1 therapy is an important alternative and realistic approach to effective control of tumor growth. As demonstrated in the experimental examples, the anti-PD-L1 antibodies activated the adaptive immune response machinery, which can lead to improved survival in cancer patients.

Accordingly, in some embodiments, provided are methods for treating a cancer in a patient in need thereof. The method, in one embodiment, entails administering to the patient an effective amount of an antibody of the present disclosure. In some embodiments, at least one of the cancer cells (e.g., stromal cells) in the patient expresses, overexpress, or is induced to express PD-L1. Induction of PD-L1 expression, for instance, can be done by administration of a tumor vaccine or radiotherapy.

Tumors that express the PD-L1 protein include those of bladder cancer, non-small cell lung cancer, renal cancer, breast cancer, urethral cancer, colorectal cancer, head and neck cancer, squamous cell cancer, Merkel cell carcinoma, gastrointestinal cancer, stomach cancer, oesophageal cancer, ovarian cancer, renal cancer, and small cell lung cancer. Accordingly, the presently disclosed antibodies can be used for treating any one or more such cancers.

Cellular therapies, such as chimeric antigen receptor (CAR) T-cell therapies, are also provided in the present disclosure. A suitable cell can be used, that is put in contact with an anti-PD-L1 antibody of the present disclosure (or alternatively engineered to express an anti-PD-L1 antibody of the present disclosure). Upon such contact or engineering, the cell can then be introduced to a cancer patient in need of a treatment. The cancer patient may have a cancer of any of the types as disclosed herein. The cell (e.g., T cell) can be, for instance, a tumor-infiltrating T lymphocyte, a CD4+ T cell, a CD8+ T cell, or the combination thereof, without limitation.

In some embodiments, the cell was isolated from the cancer patient him- or her-self. In some embodiments, the cell was provided by a donor or from a cell bank. When the cell is isolated from the cancer patient, undesired immune reactions can be minimized.

Additional diseases or conditions associated with increased cell survival, that may be treated, prevented, diagnosed and/or prognosed with the antibodies or variants, or derivatives thereof of the disclosure include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, thyroid cancer, endometrial cancer, melanoma, prostate cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

Combination Therapies

In a further embodiment, the compositions of the disclosure are administered in combination with an antineoplastic agent, an antiviral agent, antibacterial or antibiotic agent or antifungal agents. Any of these agents known in the art may be administered in the compositions of the current disclosure.

In another embodiment, compositions of the disclosure are administered in combination with a chemotherapeutic agent. Chemotherapeutic agents that may be administered with the compositions of the disclosure include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In an additional embodiment, the compositions of the disclosure are administered in combination with cytokines. Cytokines that may be administered with the compositions of the disclosure include, but are not limited to, IL-2, IL-3, IL-4, IL-5, IL-6, IL-7, IL-10, IL-12, IL-13, IL-15, anti-CD40, CD40L, and TNF-α.

In additional embodiments, the compositions of the disclosure are administered in combination with other therapeutic or prophylactic regimens, such as, for example, radiation therapy.

Combination therapies are also provided, which includes the use of one or more of the anti-PD-L1 antibody of the present disclosure along with a second anticancer (chemotherapeutic) agent. Chemotherapeutic agents may be categorized by their mechanism of action into, for example, the following groups:

anti-metabolites/anti-cancer agents such as pyrimidine analogs floxuridine, capecitabine, and cytarabine;

purine analogs, folate antagonists, and related inhibitors;

antiproliferative/antimitotic agents including natural products such as vinca alkaloid (vinblastine, vincristine) and microtubule such as taxane (paclitaxel, docetaxel), vinblastin, nocodazole, epothilones, vinorelbine (NAVELBINE®), and epipodophyllotoxins (etoposide, teniposide);

DNA damaging agents such as actinomycin, amsacrine, busulfan, carboplatin, chlorambucil, cisplatin, cyclophosphamide (CYTOXAN®), dactinomycin, daunorubicin, doxorubicin, epirubicin, iphosphamide, melphalan, merchlorethamine, mitomycin, mitoxantrone, nitrosourea, procarbazine, taxol, taxotere, teniposide, etoposide, and triethylenethiophosphoramide;

antibiotics such as dactinomycin, daunorubicin, doxorubicin, idarubicin, anthracyclines, mitoxantrone, bleomycins, plicamycin (mithramycin), and mitomycin;

enzymes such as L-asparaginase which systemically metabolizes L-asparagine and deprives cells which do not have the capacity to synthesize their own asparagine;

antiplatelet agents;

antiproliferative/antimitotic alkylating agents such as nitrogen mustards cyclophosphamide and analogs (melphalan, chlorambucil, hexamethylmelamine, and thiotepa), alkyl nitrosoureas (carmustine) and analogs, streptozocin, and triazenes (dacarbazine);

antiproliferative/antimitotic antimetabolites such as folic acid analogs (methotrexate);

platinum coordination complexes (cisplatin, oxiloplatinim, and carboplatin), procarbazine, hydroxyurea, mitotane, and aminoglutethimide;

hormones, hormone analogs (estrogen, tamoxifen, goserelin, bicalutamide, and nilutamide), and aromatase inhibitors (letrozole and anastrozole);

anticoagulants such as heparin, synthetic heparin salts, and other inhibitors of thrombin;

fibrinolytic agents such as tissue plasminogen activator, streptokinase, urokinase, aspirin, dipyridamole, ticlopidine, and clopidogrel;

antimigratory agents;

antisecretory agents (breveldin);

immunosuppressives tacrolimus, sirolimus, azathioprine, and mycophenolate;

compounds (TNP-470, genistein) and growth factor inhibitors (vascular endothelial growth factor inhibitors and fibroblast growth factor inhibitors);

angiotensin receptor blockers, nitric oxide donors;

anti-sense oligonucleotides;

antibodies such as trastuzumab and rituximab;

cell cycle inhibitors and differentiation inducers such as tretinoin;

inhibitors, topoisomerase inhibitors (doxorubicin, daunorubicin, dactinomycin, eniposide, epirubicin, etoposide, idarubicin, irinotecan, mitoxantrone, topotecan, and irinotecan), and corticosteroids (cortisone, dexamethasone, hydrocortisone, methylprednisolone, prednisone, and prednisolone);

growth factor signal transduction kinase inhibitors;

dysfunction inducers;

toxins such as Cholera toxin, ricin, *Pseudomonas* exotoxin, *Bordetella pertussis* adenylate cyclase toxin, diphtheria toxin, and caspase activators;

and chromatin.

Further examples of chemotherapeutic agents include:

alkylating agents such as thiotepa and cyclophosphamide (CYTOXAN®);

alkyl sulfonates such as busulfan, improsulfan, and pipo-sulfan;

aziridines such as benzodopa, carboquone, meturedopa, and uredopa;

emylerumines and memylamelamines including alfretamine, triemylenemelamine, triethylenephosphoramide, triethylenethiophosphoramide, and trimemylolomelamine;

acetogenins, especially bullatacin and bullatacinone;

a camptothecin, including synthetic analog topotecan;

bryostatin;

callystatin; CC-1065, including its adozelesin, carzelesin, and bizelesin synthetic analogs;

cryptophycins, particularly cryptophycin 1 and cryptophycin 8;

dolastatin;

duocarmycin, including the synthetic analogs KW-2189 and CBI-TMI;

eleutherobin;

pancratistatin;

a sarcodictyin;

spongistatin;

nitrogen mustards such as chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, and uracil mustard;

nitrosoureas such as carmustine, chlorozotocin, foremustine, lomustine, nimustine, and ranimustine;

antibiotics such as the enediyne antibiotics (e.g., calicheamicin, especially calicheamicin gammaII and calicheamicin phiI1), dynemicin including dynemicin A, bisphosphonates such as clodronate, an esperamicin, neocarzinostatin chromophore and related chromoprotein enediyne antibiotic chromomophores, aclacinomycins, actinomycin, authramycin, azaserine, bleomycins, cactinomycin, carabicin, carrninomycin, carzinophilin, chromomycins, dactinomycin, daunorubicin, detorubicin, 6-diazo-5-oxo-L-norleucine, doxorubicin (including morpholinodoxorubicin, cyanomorpholino-doxorubicin, 2-pyrrolino-doxorubicin, and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, and zorubicin;

anti-metabolites such as methotrexate and 5-fluorouracil (5-FU);

folic acid analogs such as demopterin, methotrexate, pteropterin, and trimetrexate;

purine analogs such as fludarabine, 6-mercaptopurine, thiamiprine, and thioguanine;

pyrimidine analogs such as ancitabine, azacitidine, 6-azauridine, carmofur, cytarabine, dideoxyuridine, doxifluridine, enocitabine, and floxuridine;

androgens such as calusterone, dromostanolone propionate, epitiostanol, mepitiostane, and testolactone;

anti-adrenals such as aminoglutethimide, mitotane, and trilostane;

folic acid replinishers such as frolinic acid;

trichothecenes, especially T-2 toxin, verracurin A, roridin A, and anguidine;

taxoids such as paclitaxel (TAXOL®) and docetaxel (TAXOTERE®);

platinum analogs such as cisplatin and carboplatin;

aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; polysaccharide-K (PSK); razoxane; rhizoxin; sizofiran; spirogermanium; tenuazonic acid; triaziquone; 2,2',2"-tricUorotriemylamine; urethane; vindesine; dacarbazine; mannomustine; mitobronitol; mitolactol; pipobroman; gacytosine; arabinoside ("Ara-C"); cyclophosphamide; thiopeta; chlorambucil; gemcitabine (GEMZAR®); 6-thioguanine; mercaptopurine; methotrexate; vinblastine; platinum; etoposide (VP-16); ifosfamide; mitroxantrone; vancristine; vinorelbine (NAVELBINE®); novantrone; teniposide; edatrexate; daunomycin; aminopterin; xeoloda; ibandronate; CPT-11; topoisomerase inhibitor RFS 2000; difluoromethylornithine (DFMO); retinoids such as retinoic acid; capecitabine; FOLFIRI (fluorouracil, leucovorin, and irinotecan);

and pharmaceutically acceptable salts, acids, or derivatives of any of the above.

Also included in the definition of "chemotherapeutic agent" are anti-hormonal agents such as anti-estrogens and selective estrogen receptor modulators (SERMs), inhibitors of the enzyme aromatase, anti-androgens, and pharmaceutically acceptable salts, acids or derivatives of any of the above that act to regulate or inhibit hormone action on tumors.

Examples of anti-estrogens and SERMs include, for example, tamoxifen (including NOLVADEX™), raloxifene, droloxifene, 4-hydroxytamoxifen, trioxifene, keoxifene, LY117018, onapristone, and toremifene (FARESTON®).

Inhibitors of the enzyme aromatase regulate estrogen production in the adrenal glands. Examples include 4(5)-imidazoles, aminoglutethimide, megestrol acetate (MEGACE®), exemestane, formestane, fadrozole, vorozole (RIVISOR®), letrozole (FEMARA®), and anastrozole (ARIMIDEX®).

Examples of anti-androgens include flutamide, nilutamide, bicalutamide, leuprohde, and goserelin.

Examples of chemotherapeutic agents also include anti-angiogenic agents including, but are not limited to, retinoid acid and derivatives thereof, 2-methoxyestradiol, ANGIOSTATIN®, ENDOSTATIN °, suramin, squalamine, tissue inhibitor of metalloproteinase-1, tissue inhibitor of metalloproteinase-2, plasminogen activator inhibitor-1, plasminogen activator inhibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism including proline analogs ((1-azetidine-2-carboxylic acid (LACA)), cishydroxyproline, d,I-3,4-dehydroproline, thiaproline, α,α'-dipyridyl, beta-aminopropionitrile fumarate, 4-propyl-5-(4-pyridinyl)-2(3h)-oxazolone, methotrexate, mitoxantrone, heparin, interferons, 2 macroglobulin-serum, chicken inhibitor of metalloproteinase-3 (ChIMP-3), chymostatin, beta-cyclodextrin tetradecasulfate, eponemycin, fumagillin, gold sodium thiomalate, d-penicillamine, beta-1-anticollagenase-serum, alpha-2-antiplasmin, bisantrene, lobenzarit disodium, n-2-carboxyphenyl-4-chloroanthronilic acid disodium or "CCA", thalidomide, angiostatic steroid, carboxy aminoimidazole, and metalloproteinase inhibitors such as BB-94. Other anti-angiogenesis agents include antibodies, preferably monoclonal antibodies against these angiogenic growth factors: beta-FGF, alpha-FGF, FGF-5, VEGF isoforms, VEGF-C, HGF/SF, and Ang-1/Ang-2.

Examples of chemotherapeutic agents also include anti-fibrotic agents including, but are not limited to, the compounds such as beta-aminoproprionitrile (BAPN), as well as the compounds disclosed in U.S. Pat. No. 4,965,288 (Palfreyman, et al.) relating to inhibitors of lysyl oxidase and their use in the treatment of diseases and conditions associated with the abnormal deposition of collagen and U.S. Pat. No. 4,997,854 (Kagan et al.) relating to compounds which inhibit LOX for the treatment of various pathological fibrotic states, which are herein incorporated by reference. Further exemplary inhibitors are described in U.S. Pat. No. 4,943,593 (Palfreyman et al.) relating to compounds such as 2-isobutyl-3-fluoro-, chloro-, or bromo-allylamine, U.S. Pat. No. 5,021,456 (Palfreyman et al.), U.S. Pat. No. 5,059,714 (Palfreyman et al.), U.S. Pat. No. 5,120,764 (Mccarthy et al.), U.S. Pat. No. 5,182,297 (Palfreyman et al.), U.S. Pat. No. 5,252,608 (Palfreyman et al.) relating to 2-(1-naphthyloxymemyl)-3-fluoroallylamine, and U.S. Pub. No.: 2004/0248871 (Farjanel et al.), which are herein incorporated by reference.

Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives; semicarbazide and urea derivatives; aminonitriles such as BAPN or 2-nitroethylamine; unsaturated or saturated haloamines such as 2-bromo-ethylamine, 2-chloroethylamine, 2-trifluoroethylamine, 3-bromopropylamine, and p-halobenzylamines; and selenohomocysteine lactone.

Other anti-fibrotic agents are copper chelating agents penetrating or not penetrating the cells. Exemplary compounds include indirect inhibitors which block the aldehyde derivatives originating from the oxidative deamination of the lysyl and hydroxylysyl residues by the lysyl oxidases. Examples include the thiolamines, particularly D-penicillamine, and its analogs such as 2-amino-5-mercapto-5-methylhexanoic acid, D-2-amino-3-methyl-3-((2-acetamidoethyl)dithio)butanoic acid, p-2-amino-3-methyl-3-((2-aminoethyl)dithio)butanoic acid, sodium-4-((p-1-dimethyl-2-amino-2-carboxyethyl)dithio)butanesulphurate, 2-acetamidoethyl-2-acetamidoethanethiol sulphanate, and sodium-4-mercaptobutanesulphinate trihydrate.

Examples of chemotherapeutic agents also include immunotherapeutic agents including and are not limited to therapeutic antibodies suitable for treating patients. Some examples of therapeutic antibodies include simtuzumab, abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lexatumumab, lintuzumab, lorvotuzumab, lucatumumab, mapatumumab, matuzumab, milatuzumab, minretumomab, mitumomab, moxetumomab, narnatumab, naptumomab, necitumumab, nimotuzumab, nofetumomab, ocaratuzumab, ofatumumab, olaratumab, onartuzumab, oportuzumab, oregovomab, panitumumab, parsatuzumab, patritumab, pemtumomab, pertuzumab, pintumomab, pritumumab, racotumomab, radretumab, rilotumumab, rituximab, robatumumab, satumomab, sibrotuzumab, siltuximab, solitomab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, CC49, and 3F8. Rituximab can be used for treating indolent B-cell cancers, including marginal-zone lymphoma, WM, CLL and small lymphocytic lymphoma. A combination of Rituximab and chemotherapy agents is especially effective.

The exemplified therapeutic antibodies may be further labeled or combined with a radioisotope particle such as indium-111, yttrium-90, or iodine-131.

In a one embodiment, the additional therapeutic agent is a nitrogen mustard alkylating agent. Nonlimiting examples of nitrogen mustard alkylating agents include chlorambucil.

In one embodiment, the compounds and compositions described herein may be used or combined with one or more additional therapeutic agents. The one or more therapeutic agents include, but are not limited to, an inhibitor of Abl, activated CDC kinase (ACK), adenosine A2B receptor (A2B), apoptosis signal-regulating kinase (ASK), Auroa kinase, Bruton's tyrosine kinase (BTK), BET-bromodomain (BRD) such as BRD4, c-Kit, c-Met, CDK-activating kinase (CAK), calmodulin-dependent protein kinase (CaMK), cyclin-dependent kinase (CDK), casein kinase (CK), discoidin domain receptor (DDR), epidermal growth factor receptors (EGFR), focal adhesion kinase (FAK), Flt-3, FYN, glycogen synthase kinase (GSK), HCK, histone deacetylase (HDAC), IKK such as IKKβε, isocitrate dehydrogenase (IDH) such as IDH1, Janus kinase (JAK), KDR, lymphocyte-specific protein tyrosine kinase (LCK), lysyl oxidase protein, lysyl oxidase-like protein (LOXL), LYN, matrix metalloprotease (MMP), MEK, mitogen-activated protein kinase (MAPK), NEK9, NPM-ALK, p38 kinase, platelet-derived growth factor (PDGF), phosphorylase kinase (PK), polo-like kinase (PLK), phosphatidylinositol 3-kinase (PI3K), protein kinase (PK) such as protein kinase A, B, and/or C, PYK, spleen tyrosine kinase (SYK), serine/threonine kinase TPL2, serine/threonine kinase STK, signal transduction and transcription (STAT), SRC, serine/threonine-protein kinase (TBK) such as TBK1, TIE, tyrosine kinase (TK), vascular endothelial growth factor receptor (VEGFR), YES, or any combination thereof.

ASK inhibitors include ASK1 inhibitors. Examples of ASK1 inhibitors include, but are not limited to, those described in WO 2011/008709 (Gilead Sciences) and WO 2013/112741 (Gilead Sciences).

Examples of BTK inhibitors include, but are not limited to, ibrutinib, HM71224, ONO-4059, and CC-292.

DDR inhibitors include inhibitors of DDR1 and/or DDR2. Examples of DDR inhibitors include, but are not limited to, those disclosed in WO 2014/047624 (Gilead Sciences), US 2009/0142345 (Takeda Pharmaceutical), US 2011/0287011 (Oncomed Pharmaceuticals), WO 2013/027802 (Chugai Pharmaceutical), and WO 2013/034933 (Imperial Innovations).

Examples of HDAC inhibitors include, but are not limited to, pracinostat and panobinostat.

JAK inhibitors inhibit JAK1, JAK2, and/or JAK3. Examples of JAK inhibitors include, but are not limited to, filgotinib, ruxolitinib, fedratinib, tofacitinib, baricitinib, lestaurtinib, pacritinib, XL019, AZD1480, INCB039110, LY2784544, BMS911543, and NS018.

LOXL inhibitors include inhibitors of LOXL1, LOXL2, LOXL3, LOXL4, and/or LOXL5. Examples of LOXL inhibitors include, but are not limited to, the antibodies described in WO 2009/017833 (Arresto Biosciences).

Examples of LOXL2 inhibitors include, but are not limited to, the antibodies described in WO 2009/017833 (Arresto Biosciences), WO 2009/035791 (Arresto Biosciences), and WO 2011/097513 (Gilead Biologics).

MMP inhibitors include inhibitors of MMP1 through 10. Examples of MMP9 inhibitors include, but are not limited to, marimastat (BB-2516), cipemastat (Ro 32-3555), and those described in WO 2012/027721 (Gilead Biologics).

PI3K inhibitors include inhibitors of PI3Kγ, PI3Kδ, PI3Kβ, PI3Kα, and/or pan-PI3K. Examples of PI3K inhibitors include, but are not limited to, wortmannin, BKM120, CH5132799, XL756, and GDC-0980.

Examples of PI3Kγ inhibitors include, but are not limited to, ZSTK474, AS252424, LY294002, and TG100115.

Examples of PI3Kδ inhibitors include, but are not limited to, PI3K II, TGR-1202, AMG-319, GSK2269557, X-339, X-414, RP5090, KAR4141, XL499, OXY111A, IPI-145, IPI-443, and the compounds described in WO 2005/113556 (ICOS), WO 2013/052699 (Gilead Calistoga), WO 2013/116562 (Gilead Calistoga), WO 2014/100765 (Gilead Calistoga), WO 2014/100767 (Gilead Calistoga), and WO 2014/201409 (Gilead Sciences).

Examples of PI3Kβ inhibitors include, but are not limited to, GSK2636771, BAY 10824391, and TGX221.

Examples of PI3Kα inhibitors include, but are not limited to, buparlisib, BAY 80-6946, BYL719, PX-866, RG7604, MLN1117, WX-037, AEZA-129, and PA799.

Examples of pan-PI3K inhibitors include, but are not limited to, LY294002, BEZ235, XL147 (SAR245408), and GDC-0941.

Examples of SYK inhibitors include, but are not limited to, tamatinib (R406), fostamatinib (R788), PRT062607, BAY-61-3606, NVP-QAB 205 AA, R112, R343, and those described in U.S. Pat. No. 8,450,321 (Gilead Conn.).

TKIs may target epidermal growth factor receptors (EGFRs) and receptors for fibroblast growth factor (FGF), platelet-derived growth factor (PDGF), and vascular endothelial growth factor (VEGF). Examples of TKIs that target EGFR include, but are not limited to, gefitinib and erlotinib. Sunitinib is a non-limiting example of a TKI that targets receptors for FGF, PDGF, and VEGF.

The anti-PD-L1 antibodies of the present disclosure can be used, in some embodiments, together with an immune checkpoint inhibitor. Immune checkpoints are molecules in the immune system that either turn up a signal (co-stimulatory molecules) or turn down a signal (co-inhibitory molecules). Many cancers protect themselves from the immune system by inhibiting the T cell signal through agonist for co-inhibitory molecules or antagonist for co-stimulatory molecules. An immune checkpoint agonist or antagonist can help stop such a protective mechanism by the cell cells. An immune checkpoint agonist or antagonist may target any one or more of the following checkpoint molecules, PD-1, CTLA-4, LAG-3 (also known as CD223), CD28, CD122, 4-1BB (also known as CD137), TIM3, OX-40/OX40L, CD40/CD40L, LIGHT, ICOS/ICOSL, GITR/GITRL, TIGIT, CD27, VISTA, B7H3, B7H4, HEVM or BTLA (also known as CD272).

Programmed T cell death 1 (PD-1) is a trans-membrane protein found on the surface of T cells, which, when bound to programmed T cell death ligand 1 (PD-L1) on tumor cells, results in suppression of T cell activity and reduction of T cell-mediated cytotoxicity. Thus, PD-1 and PD-L1 are immune down-regulators or immune checkpoint "off switches". Example PD-1 inhibitor include, without limitation, nivolumab, (Opdivo) (BMS-936558), pembrolizumab (Keytruda), pidilizumab, AMP-224, MEDI0680 (AMP-514), PDR001, MPDL3280A, MEDI4736, BMS-936559 and MSB0010718C.

CTLA-4 is a protein receptor that downregulates the immune system. Non-limiting examples of CTLA-4 inhibitors include ipilimumab (Yervoy) (also known as BMS-734016, MDX-010, MDX-101) and tremelimumab (formerly ticilimumab, CP-675,206).

Lymphocyte-activation gene 3 (LAG-3) is an immune checkpoint receptor on the cell surface works to suppress an immune response by action to Tregs as well as direct effects on CD8+ T cells. LAG-3 inhibitors include, without limitation, LAG525 and BMS-986016.

CD28 is constitutively expressed on almost all human CD4+ T cells and on around half of all CD8 T cells. prompts T cell expansion. Non-limiting examples of CD28 inhibitors include TGN1412.

CD122 increases the proliferation of CD8+ effector T cells. Non-limiting examples include NKTR-214.

4-1BB (also known as CD137) is involved in T-cell proliferation. CD137-mediated signaling is also known to protect T cells, and in particular, CD8+ T cells from activation-induced cell death. PF-05082566, Urelumab (BMS-663513) and lipocalin are example CD137 inhibitors.

For any of the above combination treatments, the anti-PD-L1 antibody can be administered concurrently or separately from the other anticancer agent. When administered separately, the anti-PD-L1 antibody can be administered before or after the other anticancer agent.

Treatment of Infections

As demonstrated in the experimental examples, the antibodies of the present disclosure can activate immune response which can then be useful for treating infections.

Infection is the invasion of an organism's body tissues by disease-causing agents, their multiplication, and the reaction of host tissues to these organisms and the toxins they produce. An infection can be caused by infectious agents such as viruses, viroids, prions, bacteria, nematodes such as parasitic roundworms and pinworms, arthropods such as ticks, mites, fleas, and lice, fungi such as ringworm, and other macroparasites such as tapeworms and other helminths. In one aspect, the infectious agent is a bacterium, such as Gram negative bacterium. In one aspect, the infectious agent is virus, such as DNA viruses, RNA viruses, and reverse transcribing viruses. Non-limiting examples of viruses include Adenovirus, Coxsackievirus, Epstein-Barr virus, Hepatitis A virus, Hepatitis B virus, Hepatitis C virus, Herpes simplex virus, type 1, Herpes simplex virus, type 2, Cytomegalovirus, Human herpesvirus, type 8, HIV, Influenza virus, Measles virus, Mumps virus, Human papillomavirus, Parainfluenza virus, Poliovirus, Rabies virus, Respiratory syncytial virus, Rubella virus, Varicella-zoster virus.

The antibodies of the present disclosure can also be used to treat an infectious disease caused by a microorganism, or kill a microorganism, by targeting the microorganism and an immune cell to effect elimination of the microorganism. In one aspect, the microorganism is a virus including RNA and DNA viruses, a Gram positive bacterium, a Gram negative bacterium, a protozoa or a fungus. Non-limiting examples of infectious diseases and related microorganisms are provided in Table 4 below.

TABLE 4

Infectious diseases and related microorganism sources.

| Infectious Disease | Microorganism Source |
|---|---|
| *Acinetobacter* infections | *Acinetobacter baumannii* |
| Actinomycosis | *Actinomyces israelii*, *Actinomyces gerencseriae* and *Propionibacterium propionicus* |
| African sleeping sickness (African trypanosomiasis) | *Trypanosoma brucei* |
| AIDS (Acquired immunodeficiency syndrome) | HIV (Human immunodeficiency virus) |
| Amebiasis | *Entamoeba histolytica* |
| Anaplasmosis | *Anaplasma* genus |
| Anthrax | *Bacillus anthracis* |
| *Arcanobacterium haemolyticum* infection | *Arcanobacterium haemolyticum* |
| Argentine hemorrhagic fever | Junin virus |
| Ascariasis | *Ascaris lumbricoides* |
| Aspergillosis | *Aspergillus* genus |
| Astrovirus infection | Astroviridae family |
| Babesiosis | *Babesia* genus |
| *Bacillus cereus* infection | *Bacillus cereus* |
| Bacterial pneumonia | multiple bacteria |
| Bacterial vaginosis (BV) | multiple bacteria |
| *Bacteroides* infection | *Bacteroides* genus |
| Balantidiasis | *Balantidium coli* |
| *Baylisascaris* infection | *Baylisascaris* genus |
| BK virus infection | BK virus |
| Black piedra | *Piedraia hortae* |
| *Blastocystis hominis* infection | *Blastocystis hominis* |
| Blastomycosis | *Blastomyces dermatitidis* |
| Bolivian hemorrhagic fever | Machupo virus |
| *Borrelia* infection | *Borrelia* genus |
| Botulism (and Infant botulism) | *Clostridium botulinum* |
| Brazilian hemorrhagic fever | Sabia |
| Brucellosis | *Brucella* genus |
| *Burkholderia* infection | usually *Burkholderia cepacia* and other *Burkholderia* species |
| Buruli ulcer | *Mycobacterium ulcerans* |
| Calicivirus infection (Norovirus and Sapovirus) | Caliciviridae family |
| Campylobacteriosis | *Campylobacter* genus |
| Candidiasis (Moniliasis; Thrush) | usually *Candida albicans* and other *Candida* species |
| Cat-scratch disease | *Bartonella henselae* |
| Cellulitis | usually Group A *Streptococcus* and *Staphylococcus* |
| Chagas Disease (American trypanosomiasis) | *Trypanosoma cruzi* |
| Chancroid | *Haemophilus ducreyi* |
| Chickenpox | Varicella zoster virus (VZV) |
| *Chlamydia* | *Chlamydia trachomatis* |
| *Chlamydophila pneumoniae* infection | *Chlamydophila pneumoniae* |
| Cholera | *Vibrio cholerae* |
| Chromoblastomycosis | usually *Fonsecaea pedrosoi* |
| Clonorchiasis | *Clonorchis sinensis* |
| *Clostridium difficile* infection | *Clostridium difficile* |
| Coccidioidomycosis | *Coccidioides immitis* and *Coccidioides posadasii* |

TABLE 4-continued

Infectious diseases and related microorganism sources.

| Infectious Disease | Microorganism Source |
|---|---|
| Colorado tick fever (CTF) | Colorado tick fever virus (CTFV) |
| Common cold (Acute viral rhinopharyngitis; Acute coryza) | usually rhinoviruses and coronaviruses. |
| Creutzfeldt-Jakob disease (CJD) | CJD prion |
| Crimean-Congo hemorrhagic fever (CCHF) | Crimean-Congo hemorrhagic fever virus |
| Cryptococcosis | *Cryptococcus neoformans* |
| Cryptosporidiosis | *Cryptosporidium* genus |
| Cutaneous larva migrans (CLM) | usually *Ancylostoma braziliense*; multiple other parasites |
| Cyclosporiasis | *Cyclospora cayetanensis* |
| Cysticercosis | *Taenia solium* |
| Cytomegalovirus infection | Cytomegalovirus |
| Dengue fever | Dengue viruses (DEN-1, DEN-2, DEN-3 and DEN-4) - Flaviviruses |
| Dientamoebiasis | *Dientamoeba fragilis* |
| Diphtheria | *Corynebacterium diphtheriae* |
| Diphyllobothriasis | *Diphyllobothrium* |
| Dracunculiasis | *Dracunculus medinensis* |
| Ebola hemorrhagic fever | Ebolavirus (EBOV) |
| Echinococcosis | *Echinococcus* genus |
| Ehrlichiosis | *Ehrlichia* genus |
| Enterobiasis (Pinworm infection) | *Enterobius vermicularis* |
| *Enterococcus* infection | *Enterococcus* genus |
| Enterovirus infection | Enterovirus genus |
| Epidemic typhus | *Rickettsia prowazekii* |
| Erythema infectiosum (Fifth disease) | Parvovirus B19 |
| Exanthem subitum (Sixth disease) | Human herpesvirus 6 (HHV-6) and Human herpesvirus 7 (HHV-7) |
| Fasciolopsiasis | *Fasciolopsis buski* |
| Fasciolosis | *Fasciola hepatica* and *Fasciola gigantica* |
| Fatal familial insomnia (FFI) | FFI prion |
| Filariasis | Filarioidea superfamily |
| Food poisoning by *Clostridium perfringens* | *Clostridium perfringens* |
| Free-living amebic infection | multiple |
| *Fusobacterium* infection | *Fusobacterium* genus |
| Gas gangrene (Clostridial myonecrosis) | usually *Clostridium perfringens*; other *Clostridium* species |
| Geotrichosis | *Geotrichum candidum* |
| Gerstmann-Sträussler-Scheinker syndrome (GSS) | GSS prion |
| Giardiasis | *Giardia intestinalis* |
| Glanders | *Burkholderia mallei* |
| Gnathostomiasis | *Gnathostoma spinigerum* and *Gnathostoma hispidum* |
| Gonorrhea | *Neisseria gonorrhoeae* |
| Granuloma inguinale (Donovanosis) | *Klebsiella granulomatis* |
| Group A streptococcal infection | *Streptococcus pyogenes* |
| Group B streptococcal infection | *Streptococcus agalactiae* |
| *Haemophilus influenzae* infection | *Haemophilus influenzae* |
| Hand, foot and mouth disease (HFMD) | Enteroviruses, mainly Coxsackie A virus and Enterovirus 71 (EV71) |
| Hantavirus Pulmonary Syndrome (HPS) | Sin Nombre virus |
| *Helicobacter pylori* infection | *Helicobacter pylori* |
| Hemolytic-uremic syndrome (HUS) | *Escherichia coli* O157:H7, O111 and O104:H4 |
| Hemorrhagic fever with renal syndrome (HFRS) | Bunyaviridae family |
| Hepatitis A | Hepatitis A Virus |
| Hepatitis B | Hepatitis B Virus |
| Hepatitis C | Hepatitis C Virus |
| Hepatitis D | Hepatitis D Virus |
| Hepatitis E | Hepatitis E Virus |
| Herpes simplex | Herpes simplex virus 1 and 2 (HSV-1 and HSV-2) |
| Histoplasmosis | *Histoplasma capsulatum* |
| Hookworm infection | *Ancylostoma duodenale* and *Necator americanus* |
| Human bocavirus infection | Human bocavirus (HBoV) |
| Human *ewingii* ehrlichiosis | *Ehrlichia ewingii* |
| Human granulocytic anaplasmosis (HGA) | *Anaplasma phagocytophilum* |
| Human metapneumovirus infection | Human metapneumovirus (hMPV) |
| Human monocytic ehrlichiosis | *Ehrlichia chaffeensis* |
| Human papillomavirus (HPV) infection | Human papillomavirus (HPV) |
| Human parainfluenza virus infection | Human parainfluenza viruses (HPIV) |
| Hymenolepiasis | *Hymenolepis nana* and *Hymenolepis diminuta* |
| Epstein-Barr Virus Infectious | Epstein-Barr Virus (EBV) |

TABLE 4-continued

Infectious diseases and related microorganism sources.

| Infectious Disease | Microorganism Source |
|---|---|
| Mononucleosis (Mono) | |
| Influenza (flu) | Orthomyxoviridae family |
| Isosporiasis | *Isospora belli* |
| Kawasaki disease | unknown; evidence supports that it is infectious |
| Keratitis | multiple |
| *Kingella kingae* infection | *Kingella kingae* |
| Kuru | Kuru prion |
| Lassa fever | Lassa virus |
| Legionellosis (Legionnaires' disease) | *Legionella pneumophila* |
| Legionellosis (Pontiac fever) | *Legionella pneumophila* |
| Leishmaniasis | *Leishmania* genus |
| Leprosy | *Mycobacterium leprae* and *Mycobacterium lepromatosis* |
| Leptospirosis | *Leptospira* genus |
| Listeriosis | *Listeria monocytogenes* |
| Lyme disease (Lyme borreliosis) | usually *Borrelia burgdorferi* and other *Borrelia* species |
| Lymphatic filariasis (Elephantiasis) | *Wuchereria bancrofti* and *Brugia malayi* |
| Lymphocytic choriomeningitis | Lymphocytic choriomeningitis virus (LCMV) |
| Malaria | *Plasmodium* genus |
| Marburg hemorrhagic fever (MHF) | Marburg virus |
| Measles | Measles virus |
| Melioidosis (Whitmore's disease) | *Burkholderia pseudomallei* |
| Meningitis | multiple |
| Meningococcal disease | *Neisseria meningitidis* |
| Metagonimiasis | usually *Metagonimus yokagawai* |
| Microsporidiosis | Microsporidia phylum |
| Molluscum contagiosum (MC) | Molluscum contagiosum virus (MCV) |
| Mumps | Mumps virus |
| Murine typhus (Endemic typhus) | *Rickettsia typhi* |
| Mycoplasma pneumonia | *Mycoplasma pneumoniae* |
| Mycetoma | numerous species of bacteria (Actinomycetoma) and fungi (Eumycetoma) |
| Myiasis | parasitic dipterous fly larvae |
| Neonatal conjunctivitis (Ophthalmia neonatorum) | most commonly *Chlamydia trachomatis* and *Neisseria gonorrhoeae* |
| (New) Variant Creutzfeldt-Jakob disease (vCJD, nvCJD) | vCJD prion |
| Nocardiosis | usually *Nocardia asteroides* and other *Nocardia* species |
| Onchocerciasis (River blindness) | *Onchocerca volvulus* |
| Paracoccidioidomycosis (South American blastomycosis) | *Paracoccidioides brasiliensis* |
| Paragonimiasis | usually *Paragonimus westermani* and other *Paragonimus* species |
| Pasteurellosis | *Pasteurella* genus |
| Pediculosis capitis (Head lice) | *Pediculus humanus capitis* |
| Pediculosis corporis (Body lice) | *Pediculus humanus corporis* |
| Pediculosis pubis (Pubic lice, Crab lice) | *Phthirus pubis* |
| Pelvic inflammatory disease (PID) | multiple |
| Pertussis (Whooping cough) | *Bordetella pertussis* |
| Plague | *Yersinia pestis* |
| Pneumococcal infection | *Streptococcus pneumoniae* |
| *Pneumocystis* pneumonia (PCP) | *Pneumocystis jirovecii* |
| Pneumonia | multiple |
| Poliomyelitis | Poliovirus |
| *Prevotella* infection | *Prevotella* genus |
| Primary amoebic meningoencephalitis (PAM) | usually *Naegleria fowleri* |
| Progressive multifocal leukoencephalopathy | JC virus |
| Psittacosis | *Chlamydophila psittaci* |
| Q fever | *Coxiella burnetii* |
| Rabies | Rabies virus |
| Rat-bite fever | *Streptobacillus moniliformis* and *Spirillum minus* |
| Respiratory syncytial virus infection | Respiratory syncytial virus (RSV) |
| Rhinosporidiosis | *Rhinosporidium seeberi* |
| Rhinovirus infection | Rhinovirus |
| Rickettsial infection | *Rickettsia* genus |
| Rickettsialpox | *Rickettsia akari* |
| Rift Valley fever (RVF) | Rift Valley fever virus |
| Rocky mountain spotted fever (RMSF) | *Rickettsia rickettsii* |
| Rotavirus infection | Rotavirus |
| Rubella | Rubella virus |
| Salmonellosis | *Salmonella* genus |
| SARS (Severe Acute Respiratory Syndrome) | SARS coronavirus |

TABLE 4-continued

Infectious diseases and related microorganism sources.

| Infectious Disease | Microorganism Source |
|---|---|
| Scabies | *Sarcoptes scabiei* |
| Schistosomiasis | *Schistosoma* genus |
| Sepsis | multiple |
| Shigellosis (Bacillary dysentery) | *Shigella* genus |
| Shingles (Herpes zoster) | Varicella zoster virus (VZV) |
| Smallpox (Variola) | Variola major or Variola minor |
| Sporotrichosis | *Sporothrix schenckii* |
| Staphylococcal food poisoning | *Staphylococcus* genus |
| Staphylococcal infection | *Staphylococcus* genus |
| Strongyloidiasis | *Strongyloides stercoralis* |
| Syphilis | *Treponema pallidum* |
| Taeniasis | *Taenia* genus |
| Tetanus (Lockjaw) | *Clostridium tetani* |
| Tinea barbae (Barber's itch) | usually *Trichophyton* genus |
| Tinea capitis (Ringworm of the Scalp) | usually *Trichophyton tonsurans* |
| Tinea corporis (Ringworm of the Body) | usually *Trichophyton* genus |
| Tinea cruris (Jock itch) | usually *Epidermophyton floccosum*, *Trichophyton rubrum*, and *Trichophyton mentagrophytes* |
| Tinea manuum (Ringworm of the Hand) | *Trichophyton rubrum* |
| Tinea nigra | usually *Hortaea werneckii* |
| Tinea pedis (Athlete's foot) | usually *Trichophyton* genus |
| Tinea unguium (Onychomycosis) | usually *Trichophyton* genus |
| Tinea versicolor (Pityriasis versicolor) | *Malassezia* genus |
| Toxocariasis (Ocular Larva Migrans (OLM)) | *Toxocara canis* or *Toxocara cati* |
| Toxocariasis (Visceral Larva Migrans (VLM)) | *Toxocara canis* or *Toxocara cati* |
| Toxoplasmosis | *Toxoplasma gondii* |
| Trichinellosis | *Trichinella spiralis* |
| Trichomoniasis | *Trichomonas vaginalis* |
| Trichuriasis (Whipworm infection) | *Trichuris trichiura* |
| Tuberculosis | usually *Mycobacterium tuberculosis* |
| Tularemia | *Francisella tularensis* |
| *Ureaplasma urealyticum* infection | *Ureaplasma urealyticum* |
| Venezuelan equine encephalitis | Venezuelan equine encephalitis virus |
| Venezuelan hemorrhagic fever | Guanarito virus |
| Viral pneumonia | multiple viruses |
| West Nile Fever | West Nile virus |
| White piedra (Tinea blanca) | *Trichosporon beigelii* |
| *Yersinia pseudotuberculosis* infection | *Yersinia pseudotuberculosis* |
| Yersiniosis | *Yersinia enterocolitica* |
| Yellow fever | Yellow fever virus |
| Zygomycosis | Mucorales order (Mucormycosis) and Entomophthorales order (Entomophthoramycosis) |

A specific dosage and treatment regimen for any particular patient will depend upon a variety of factors, including the particular antibodies, variant or derivative thereof used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

Methods of administration of the antibodies, variants or include but are not limited to intradermal, intramuscular, intraperitoneal, intravenous, subcutaneous, intranasal, epidural, and oral routes. The antigen-binding polypeptides or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Thus, pharmaceutical compositions containing the antigen-binding polypeptides of the disclosure may be administered orally, rectally, parenterally, intracisternally, intravaginally, intraperitoneally, topically (as by powders, ointments, drops or transdermal patch), bucally, or as an oral or nasal spray.

The term "parenteral" as used herein refers to modes of administration which include intravenous, intramuscular, intraperitoneal, intrasternal, subcutaneous and intra-articular injection and infusion.

Administration can be systemic or local. In addition, it may be desirable to introduce the antibodies of the disclosure into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

It may be desirable to administer the antibodies polypeptides or compositions of the disclosure locally to the area in need of treatment; this may be achieved by, for example, and not by way of limitation, local infusion during surgery, topical application, e.g., in conjunction, with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the disclosure, care must be taken to use materials to which the protein does not absorb.

In another embodiment, the antibodies or composition can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the antigen-binding polypeptide or composition can be delivered in a controlled release system. In one embodiment, a pump may be used (see Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., 1983, Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)). Other controlled release systems are discussed in the review by Langer (1990, Science 249:1527-1533).

In a specific embodiment where the composition of the disclosure comprises a nucleic acid or polynucleotide encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., 1991, Proc. Natl. Acad. Sci. USA 88:1864-1868), etc. Alternatively, a nucleic acid can be introduced intracellularly and incorporated within host cell DNA for expression, by homologous recombination.

The amount of the antibodies of the disclosure which will be effective in the treatment, inhibition and prevention of an inflammatory, immune or malignant disease, disorder or condition can be determined by standard clinical techniques. In addition, in vitro assays may optionally be employed to help identify optimal dosage ranges. The precise dose to be employed in the formulation will also depend on the route of administration, and the seriousness of the disease, disorder or condition, and should be decided according to the judgment of the practitioner and each patient's circumstances. Effective doses may be extrapolated from dose-response curves derived from in vitro or animal model test systems.

As a general proposition, the dosage administered to a patient of the antigen-binding polypeptides of the present disclosure is typically 0.1 mg/kg to 100 mg/kg of the patient's body weight, between 0.1 mg/kg and 20 mg/kg of the patient's body weight, or 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the disclosure may be reduced by enhancing uptake and tissue penetration (e.g., into the brain) of the antibodies by modifications such as, for example, lipidation.

The methods for treating an infectious or malignant disease, condition or disorder comprising administration of an antibody, variant, or derivative thereof of the disclosure are typically tested in vitro, and then in vivo in an acceptable animal model, for the desired therapeutic or prophylactic activity, prior to use in humans. Suitable animal models, including transgenic animals, are well known to those of ordinary skill in the art. For example, in vitro assays to demonstrate the therapeutic utility of antigen-binding polypeptide described herein include the effect of an antigen-binding polypeptide on a cell line or a patient tissue sample. The effect of the antigen-binding polypeptide on the cell line and/or tissue sample can be determined utilizing techniques known to those of skill in the art, such as the assays disclosed elsewhere herein. In accordance with the disclosure, in vitro assays which can be used to determine whether administration of a specific antigen-binding polypeptide is indicated, include in vitro cell culture assays in which a patient tissue sample is grown in culture, and exposed to or otherwise administered a compound, and the effect of such compound upon the tissue sample is observed.

Various delivery systems are known and can be used to administer an antibody of the disclosure or a polynucleotide encoding an antibody of the disclosure, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc.

Diagnostic Methods

Over-expression of PD-L1 is observed in certain tumor samples, and patients having PD-L1-over-expressing cells are likely responsive to treatments with the anti-PD-L1 antibodies of the present disclosure. Accordingly, the antibodies of the present disclosure can also be used for diagnostic and prognostic purposes.

A sample that preferably includes a cell can be obtained from a patient, which can be a cancer patient or a patient desiring diagnosis. The cell be a cell of a tumor tissue or a tumor block, a blood sample, a urine sample or any sample from the patient. Upon optional pre-treatment of the sample, the sample can be incubated with an antibody of the present disclosure under conditions allowing the antibody to interact with a PD-L1 protein potentially present in the sample. Methods such as ELISA can be used, taking advantage of the anti-PD-L1 antibody, to detect the presence of the PD-L1 protein in the sample.

Presence of the PD-L1 protein in the sample (optionally with the amount or concentration) can be used for diagnosis of cancer, as an indication that the patient is suitable for a treatment with the antibody, or as an indication that the patient has (or has not) responded to a cancer treatment. For a prognostic method, the detection can be done at once, twice or more, at certain stages, upon initiation of a cancer treatment to indicate the progress of the treatment.

Compositions

The present disclosure also provides pharmaceutical compositions. Such compositions comprise an effective amount of an antibody, and an acceptable carrier. In some embodiments, the composition further includes a second anticancer agent (e.g., an immune checkpoint inhibitor).

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. Further, a "pharmaceutically acceptable carrier" will generally be a non-toxic solid, semisolid or liquid filler, diluent, encapsulating material or formulation auxiliary of any type.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfate; chelating agents such as ethylenediaminetetraacetic acid; and agents for the adjustment of tonicity such as sodium chloride or dextrose are also envisioned. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences by E. W. Martin, incorporated herein by reference. Such compositions will contain a therapeutically effective amount of the antigen-binding polypeptide, preferably in purified form, together with a suitable amount of carrier so as to provide the form for proper administration to the patient. The formulation should suit the mode of administration. The parental preparation can be enclosed in ampoules, disposable syringes or multiple dose vials made of glass or plastic.

In an embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the disclosure can be formulated as neutral or salt forms.

Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

EXAMPLES

Example 1: Generation of Human Monoclonal Antibodies Against Human PD-L1

Anti-human-PD-L1 mouse monoclonal antibodies were generated using the hybridoma technology.

Antigen: human PDL1-Fc protein and human PD-L1 highly expressed CHOK1 cell line (PDL1-CHOK1 cell line).

Immunization: To generate mouse monoclonal antibodies to human PD-L1, 6-8 week female BALB/c mice were firstly immunized with $1.5 \times 10^7$ PDL1-CHOK1 cells. Day 14 and 33 post first immunization, the immunized mice were re-immunized with $1.5 \times 10^7$ PDL1-CHOK1 cells respectively. To select mice producing antibodies that bond PD-L1 protein, sera from immunized mice were tested by ELISA. Briefly, microtiter plates were coated with human PD-L1 protein at 1 μg/ml in PBS, 100 μl/well at room temperature (RT) overnight, then blocked with 100 μl/well of 5% BSA. Dilutions of plasma from immunized mice were added to each well and incubated for 1-2 hours at RT. The plates were washed with PBS/Tween and then incubate with anti-mouse IgG antibody conjugated with Horse Radish Peroxidase (HRP) for 1 hour at RT. After washing, the plates were developed with ABTS substrate and analyzed by spectrophotometer at OD 405 nm. Mice with sufficient titers of anti-PDL1 IgG were boosted with 50 ug human PDL1-Fc protein at Day 54 post-immunization. The resulting mice were used for fusions. The hybridoma supernatants were tested for anti-PD-L1 IgGs by ELISA.

Hybridoma clones HL1210-3, HL1207-3, HL1207-9 and HL1120-3 were selected for further analysis. The amino acid and polynucleotide sequences of the variable regions of HL1210-3 are provided in Table 5 below.

TABLE 5

HL1210-3 variable sequences

| Name | Sequence | SEQ ID NO: |
| --- | --- | --- |
| HL1210-3 VH | GAAGTGAAACTGGTGGAGTCTGGGGGAGACTTAGTGAAGC CTGGAGGGTCCCTGAAACTCTCCTGTGCAGCCTCTGGATT | 112 |

TABLE 5-continued

HL1210-3 variable sequences

| Name | Sequence | SEQ ID NO: |
|---|---|---|
| | CACTTTCAGTAGCTATGACATGTCTTGGGTTCGCCAGACT<br>CCGGAGAAGAGTCTGGAGTGGGTCGCAACCATTAGTGATG<br>GTGGTGGTTACATCTACTATTCAGACAGTGTGAAGGGGCG<br>ATTTACCATCTCCAGAGACAATGCCAAGAACAACCTGTAC<br>CTGCAAATGAGCAGTCTGAGGTCTGAGGACACGGCCTTGT<br>ATATTTGTGCAAGAGAATTTGGTAAGCGCTATGCTTTGGA<br>CTACTGGGGTCAAGGAACCTCAGTCACCGTCTCCTCA | |
| HL1210-3 VH | EVKLVESGGDLVKPGGSLKLSCAASGFTFSSYDMSWVRQT<br>PEKSLEWVATISDGGGYIYYSDSVKGRFTISRDNAKNNLY<br>LQMSSLRSEDTALYICAREFGKRYALDYWGQGTSVT | 113 |
| HL1210-3 VL | GACATTGTGATGACCCAGTCTCACAAATTCATGTCCACAT<br>CGGTAGGAGACAGGGTCAGCATCTCCTGCAAGGCCAGTCA<br>GGATGTGACTCCTGCTGTCGCCTGGTATCAACAGAAGCCA<br>GGACAATCTCCTAAACTACTGATTTACTCCACATCCTCCC<br>GGTACACTGGAGTCCCTGATCGCTTCACTGGCAGTGGATC<br>TGGGACGGATTTCACTTTCACCATCAGCAGTGTGCAGGCT<br>GAAGACCTGGCAGTTTATTACTGTCAGCAACATTATACTA<br>CTCCGCTCACGTTCGGTGCTGGGACCAAGCTGGAGCTGAA<br>A | 114 |
| HL1210-3 VL | DIVMTQSHKFMSTSVGDRVSISCKASQDVTPAVAWYQQKP<br>GQSPKLLIYSTSSRYTGVPDRFTGSGSGTDFTFTISSVQA<br>EDLAVYYCQQHYTTPLTFGAGTKLELK | 115 |

Example 2: HL1210-3 Mouse Monoclonal Antibody's Binding Activity for Human PD-L1

To evaluate the binding activity of hybridoma clone HL1210-3, the purified mAb from this clone were subjected to ELISA test. Briefly, microtiter plates were coated with human PD-L1-Fc protein at 0.1 µg/ml in PBS, 100 µl/well at 4° C. overnight, then blocked with 100 µl/well of 5% BSA. Three-fold dilutions of HL1210-3 antibodies starting from 0.2 µg/ml were added to each well and incubated for 1-2 hours at RT. The plates were washed with PBS/Tween and then incubate with goat-anti-mouse IgG antibody conjugated with Horse Radish Peroxidase (HRP) for 1 hour at RT. After washing, the plates were developed with TMB substrate and analyzed by spectrophotometer at OD 450-630 nm. As shown in FIG. 1, HL1210-3 can bind to human PD-L1 with high activity ($EC_{50}$=5.539 ng/ml).

Example 3: HL1210-3 Mouse mAb Blocked Human PD-L1 Binding to its Receptor PD-1

Receptor Blocking Assay by Using Recombinant Human PD-L1

Figure 2:
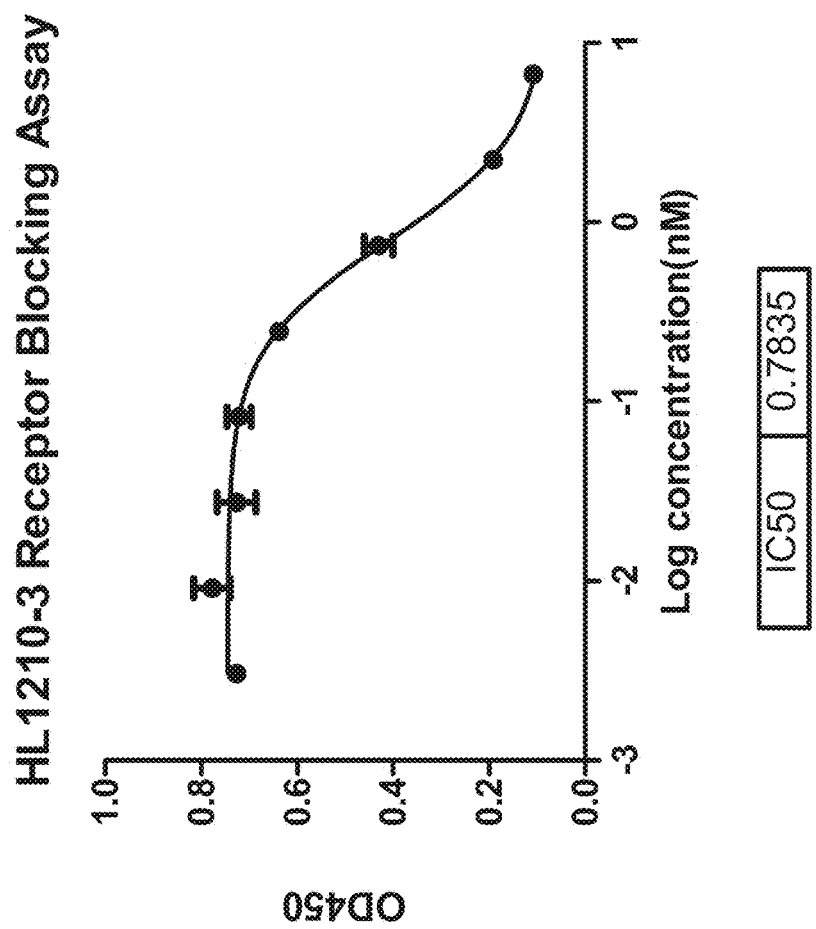
FIG. 2 shows that HL1210-3 can efficiently inhibit the binding of human PD-L1 to human PD1.

To evaluate the blocking effect of HL1210-3 mouse mAb on recombinant human PD-L1 to bind to its receptor PD-1, the ELISA based receptor blocking assay was employed. Briefly, microtiter plates were coated with human PD-L1-Fc protein at 1 µg/ml in PBS, 100 µl/well at 4° C. overnight, then blocked with 100 µl/well of 5% BSA. 50 µl biotin-labeled human PD-1-Fc protein and 3-fold dilutions of HL1210-3 antibodies starting from 2 µg/ml at 50 µl were added to each well and incubated for 1 hour at 37° C. The plates were washed with PBS/Tween and then incubated with Streptavidin-HRP for 1 hour at 37° C. After washing, the plates were developed with TMB substrate and analyzed by spectrophotometer at OD 450-630 nm. As shown in FIG. 2, HL1210-3 can efficiently inhibit the binding of human PD-L1 to human PD1 at $IC_{50}$=0.7835 nM.

Receptor Blocking Assay by Using Mammalian Cell Expressed Human PD-L1

Figure 3:
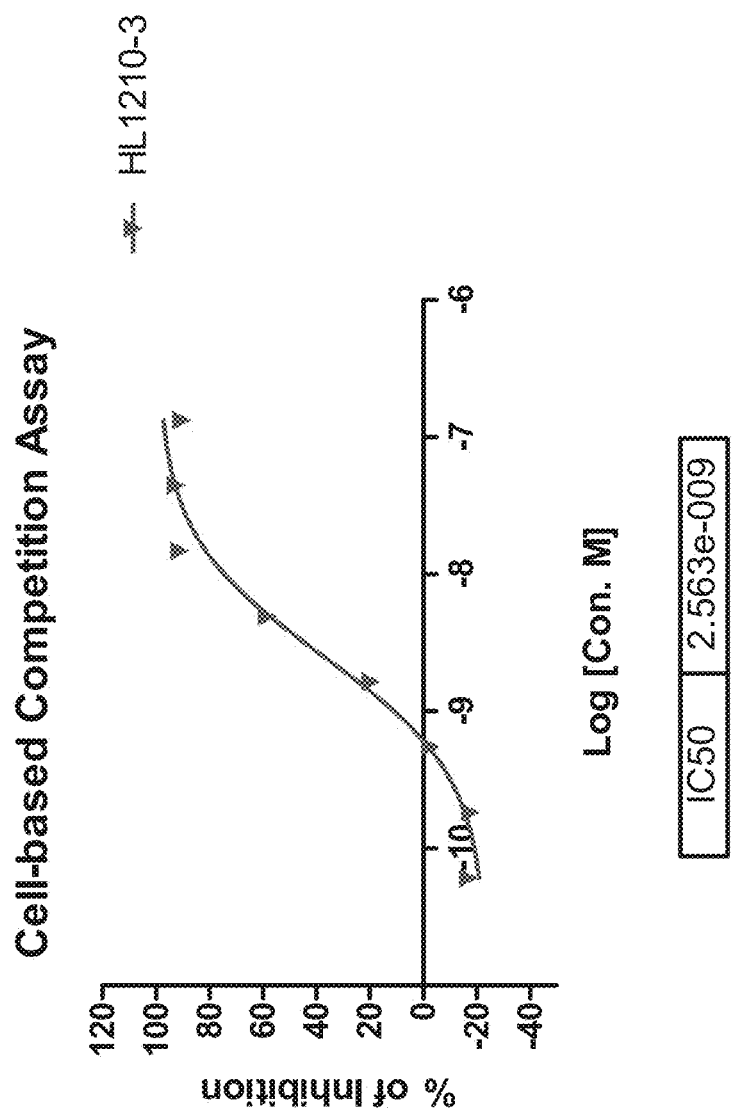
FIG. 3 shows the HL1210-3 antibody can highly efficiently inhibit the binding of PD-1 on PD-L1 expressed on mammalian cells.

To evaluate the blocking effect of HL1210-3 mouse mAb on human PD-L1 expressed on mammalian cells to bind to its receptor PD-1, the FACS-based receptor blocking assay was used. Briefly, PDL1-CHOK1 cells were firstly incubated with 3-fold serious diluted HL1210-3 mouse mAb starting at 20 µg/ml at RT for 1 hour. After wash by FACS buffer (PBS with 2% FBS), the biotin-labeled huPD-1 were added to each well and incubated at RT for 1 hour. Then, the Streptavidin-PE were added to each well for 0.5 hour post twice wash with FACS buffer. The mean florescence intensity (MFI) of PE were evaluated by FACSAriaIII. As shown in FIG. 3, the HL1210-3 antibody can highly efficiently inhibit the binding of PD-1 on PD-L1 expressed on mammalian cells at IC50 of 2.56 nM with 92.6% top inhibition rate.

% of inhibition=(1−MFI of testing antibody/MFI of vehicle contorl)×100%

Example 4: HL1210-3 Mouse mAb Promoted Human T Cell Immune Response

Figure 4:
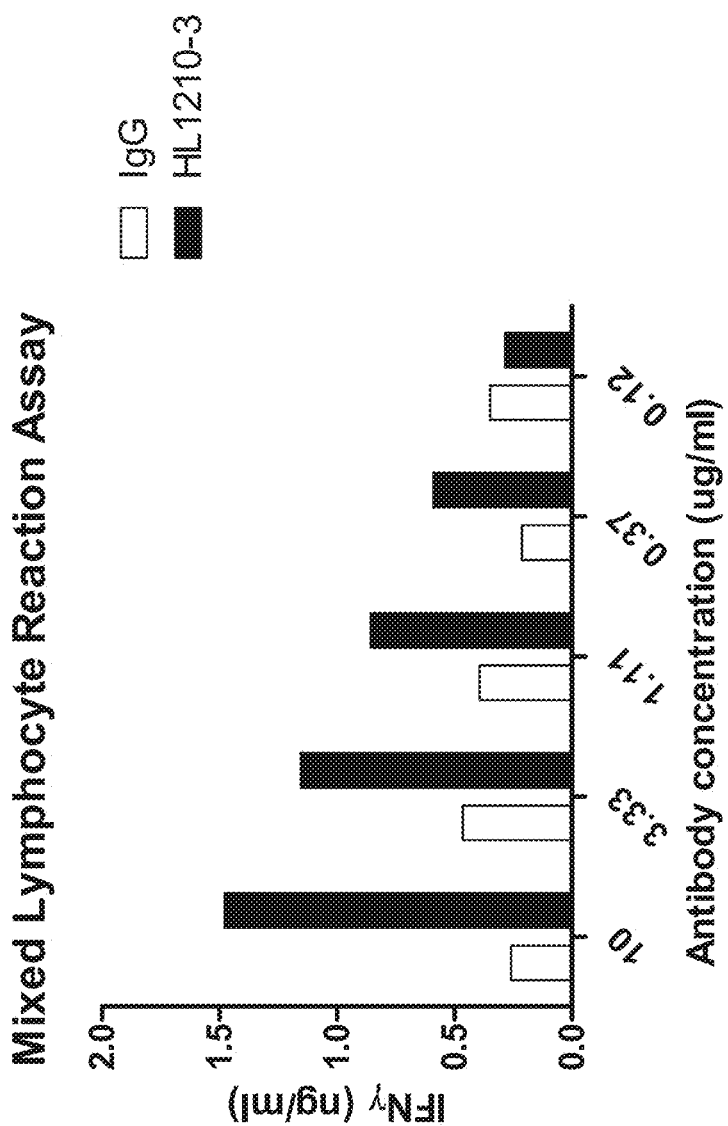
FIG. 4 shows that the tested anti-PD-L1 antibodies can promote human T cell response.

To evaluate the effect of HL1210-3 mouse mAb, the response of human T cells assessed in a mixed lymphocyte reaction setting. Human DCs were differentiated from CD14+ monocytes in the presence of GM-CSF and IL-4 for 7 days. CD4+ T cells isolated from another donor were then co-cultured with the DCs and serial dilutions of anti-PD-L1 blocking antibody. At day 5 post-inoculation, the culture supernatant was assayed for IFNγ production. The results indicated that the HL1210-3 antibodies can dose-dependently promote IFNγ production, suggesting anti-PD-L1 antibody can promote human T cell response (FIG. 4).

Example 5: The Binding Affinity of HL1210-3 Mouse mAb

Figure 5:
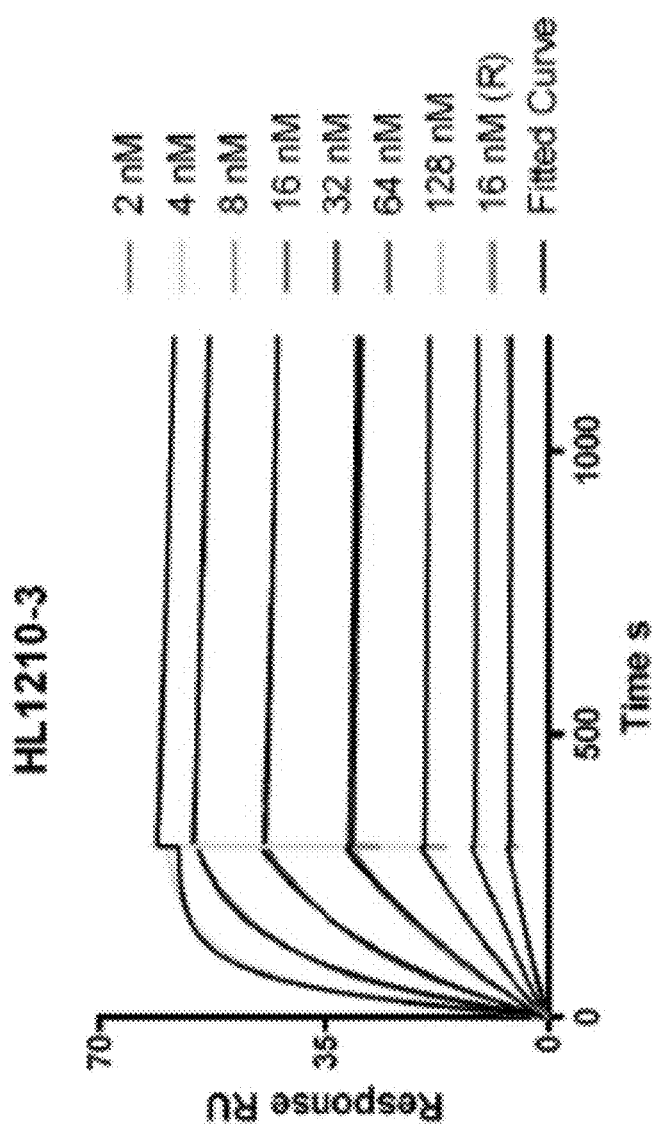
FIG. 5 shows the binding kinetics of HL1210-3 to recombinant PD-L1.

The binding of the HL1210-3 antibodies to recombinant PD-L1 protein (human PD-L1-his taq) was tested with BIACORE™ using a capture method. The HL1210-3 mouse mAb was captured using anti-mouse Fc antibody coated on a CM5 chip. A series dilution of human PD-L1-his taq protein was injected over captured antibody for 3 mins at a flow rate of 25 µg/ml. The antigen was allowed to dissociate for 900 s. All the experiment were carried out on a Biacore T200. Data analysis was carried out using Biacore T200 evaluation software. The result are shown in FIG. 5 and Table 6 below.

TABLE 6

| Binding Kinetics of HL1210-3 to recombinant human PD-L1 | | | |
|---|---|---|---|
| Antibody | ka (1/Ms) | kd (1/s) | KD (M) |
| HL1210-3 | 1.61E+05 | 4.69E−05 | 2.93E−10 |

Example 6: Humanization of the HL1210-3 Mouse mAb

The mAb HL1210-3 variable region genes were employed to create a humanized MAb. In the first step of this process, the amino acid sequences of the VH and VK of MAb HL1210-3 were compared against the available database of human Ig gene sequences to find the overall best-matching human germline Ig gene sequences. For the light chain, the closest human match was the O18/Jk2 and KV1-39*01/KJ2*04 gene, and for the heavy chain the closest human match was the VH3-21 gene. VH3-11, VH3-23, VH3-7*01 and VH3-48 genes were also selected due to their close matches.

Humanized variable domain sequences were then designed where the CDR1 (SEQ ID NO.4), 2 (SEQ ID NO.5) and 3 (SEQ ID NO.6) of the HL1210-3 light chain were grafted onto framework sequences of the O18/Jk2 and KV1-39*01/KJ2*04 gene, and the CDR1 (SEQ ID NO.1), 2 (SEQ ID NO.2), and 3 (SEQ ID NO.3) sequences of the HL1210-3 VH were grafted onto framework sequences of the VH3-21, VH3-11, VH3-23, VH3-48 or VH3-7*01 gene. A 3D model was then generated to determine if there were any framework positions where replacing the mouse amino acid to the human amino acid could affect binding and/or CDR conformation. In the case of the light chain, 22S, 43S, 60D, 63T and 42Q (Kabat numbering, see Table 7) in framework were identified. In the case of the heavy chain, 1E, 37V, 40T, 44S, 49A, 77N, 91I, 94R and 108T in the framework was involved in back-mutations.

TABLE 7

| Humanization Design | |
|---|---|
| Construct | Mutation |
| VH Design I: VH3-21/JH6 | |
| Hu1210 VH | Chimera |
| Hu1210 VH.1 | CDR-grafted |
| Hu1210 VH.1a | S49A |
| Hu1210 VH.1b | S49A, G44S, Y91I |
| VH Design II: VH3-11/JH6 | |
| Hu1210 VH.2 | CDR-grafted, Q1E |
| Hu1210 VH.2a | Q1E, S49A |
| Hu1210 VH.2b | Q1E, I37V, S49A, G44S, Y91I |
| VH Design III: VH3-23/JH6 | |
| Hu1210 VH.3 | CDR-grafted, K94R |
| Hu1210 VH.3a | G44S, S49A, Y91I, K94R |
| VH Design IV: VH3-48/JH6 | |
| Hu1210 VH.4 | CDR-grafted |
| Hu1210 VH.4a | S49A |
| Hu1210 VH.4b | S49A, G44S, Y91I |
| Hu1210 VH.4c | D52E, S49A, G44S, Y91I |
| Hu1210 VH.4d | G53A, S49A, G44S, Y91I |
| Hu1210 VH.4e | G53V, S49A, G44S, Y91I |
| VH Design V: VH3-7*01/HJ1*01 | |
| Hu1210 VH.5 | CDR-grafted |
| Hu1210 VH.5a | H91I |
| Hu1210 VH.5b | H91I, H108T |
| Hu1210 VH.5c | H91I, H77N |
| Hu1210 VH.5d | H91I, H77N, H40T |
| VK Design I: O18/Jk2 | |
| Hu1210 Vk | Chimera |
| Hu1210 Vk.1 | CDR-grafted |
| Hu1210 Vk.1a | A43S |
| VK Design II: KV1-39*01/KJ2*04 | |
| Hu1210 Vk.2 | CDR-grafted |
| Hu1210 Vk.2a | L60D, L63T |
| Hu1210 Vk.2b | L60D, L63T, L42Q, L43S |
| Hu1210 Vk.2c | L60D, L63T, L42Q, L43S, T22S |

The amino acid and nucleotide sequences of some of the humanized antibody are listed in Table 8 below.

TABLE 8

| Humanized antibody sequences (bold indicates CDR) | | |
|---|---|---|
| Name | Sequence | SEQ ID NO: |
| HL1210-VH | EVKLVESGGDLVKPGGSLKLSCAASGFTFSSYDMSWVRQTPEKSLEWVATISDGGGYIYYSDSVKGRFTISRDNAKNNLYLQMSSLRSEDTALYICAREFGKRYALDYWGQGTSVTVSS | 7 |
| Hu1210 VH.1 | EVQLVESGGGLVKPGGSLRLSCAASGFTFSSYDMSWVRQAPGKGLEWVSTISDGGGYIYYSDSVKGRFTISRDNAKNSLYLQMNSLRAEDTAVYYCAREFGKRYALDYWGQGTTVTVSS | 8 |
| Hu1210 VH.1a | EVQLVESGGGLVKPGGSLRLSCAASGFTFSSYDMSWVRQAPGKGLEWVATISDGGGYIYYSDSVKGRFTISRDNAKNSLYLQMNSLRAEDTAVYYCAREFGKRYALDYWGQGTTVTVSS | 9 |

TABLE 8-continued

Humanized antibody sequences (bold indicates CDR)

| Name | Sequence | SEQ ID NO: |
|---|---|---|
| Hu1210 VH.1b | EVQLVESGGGLVKPGGSLRLSCAASGFTFSSYDMSWVRQAPGKSLEWVATISDGGGYIYYSDSVKGRFTISRDNAKNSLYLQMNSLRAEDTAVYICAREFGKRYALDYWGQGTTVTVSS | 10 |
| Hu1210 VH.2 | EVQLVESGGGLVKPGGSLRLSCAASGFTFSSYDMSWIRQAPGKGLEWVSTISDGGGYIYYSDSVKGRFTISRDNAKNSLYLQMNSLRAEDTAVYYCAREFGKRYALDYWGQGTTVTVSS | 11 |
| Hu1210 VH.2a | EVQLVESGGGLVKPGGSLRLSCAASGFTFSSYDMSWIRQAPGKGLEWVATISDGGGYIYYSDSVKGRFTISRDNAKNSLYLQMNSLRAEDTAVYYCAREFGKRYALDYWGQGTTVTVSS | 12 |
| Hu1210 VH.2b | EVQLVESGGGLVKPGGSLRLSCAASGFTFSSYDMSWVRQAPGKSLEWVATISDGGGYIYYSDSVKGRFTISRDNAKNSLYLQMNSLRAEDTAVYICAREFGKRYALDYWGQGTTVTVSS | 13 |
| Hu1210 VH.3 | EVQLLESGGGLVQPGGSLRLSCAASGFTFSSYDMSWVRQAPGKGLEWVSTISDGGGYIYYSDSVKGRFTISRDNSKNTLYLQMNSLRAEDTAVYYCAREFGKRYALDYWGQGTTVTVSS | 14 |
| Hu1210 VH.3a | EVQLLESGGGLVQPGGSLRLSCAASGFTFSSYDMSWVRQAPGKGLEWVATISDGGGYIYYSDSVKGRFTISRDNSKNTLYLQMNSLRAEDTAVYYCAREFGKRYALDYWGQGTTVTVSS | 15 |
| Hu1210 VH.4 | EVQLVESGGGLVQPGGSLRLSCAASGFTFSSYDMSWVRQAPGKGLEWVSTISDGGGYIYYSDSVKGRFTISRDNAKNSLYLQMNSLRDEDTAVYYCAREFGKRYALDYWGQGTTVTVSS | 16 |
| Hu1210 VH.4a | EVQLVESGGGLVQPGGSLRLSCAASGFTFSSYDMSWVRQAPGKGLEWVATISDGGGYIYYSDSVKGRFTISRDNAKNSLYLQMNSLRDEDTAVYYCAREFGKRYALDYWGQGTTVTVSS | 17 |
| Hu1210 VH.4b | EVQLVESGGGLVQPGGSLRLSCAASGFTFSSYDMSWVRQAPGKSLEWVATISDGGGYIYYSDSVKGRFTISRDNAKNSLYLQMNSLRDEDTAVYICAREFGKRYALDYWGQGTTVTVSS | 18 |
| Hu1210 VH.4c | EVQLVESGGGLVQPGGSLRLSCAASGFTFSSYDMSWVRQAPGKSLEWVATISEGGGYIYYSDSVKGRFTISRDNAKNSLYLQMNSLRDEDTAVYICAREFGKRYALDYWGQGTTVTVSS | 19 |
| Hu1210 VH.4d | EVQLVESGGGLVQPGGSLRLSCAASGFTFSSYDMSWVRQAPGKSLEWVATISDAGGYIYYSDSVKGRFTISRDNAKNSLYLQMNSLRDEDTAVYICAREFGKRYALDYWGQGTTVTVSS | 20 |
| Hu1210 VH.4e | EVQLVESGGGLVQPGGSLRLSCAASGFTFSSYDMSWVRQAPGKSLEWVATISDVGGYIYYSDSVKGRFTISRDNAKNSLYLQMNSLRDEDTAVYICAREFGKRYALDYWGQGTTVTVSS | 21 |
| Hu1210 VH.5 | EVQLVESGGGLVQPGGSLRLSCAASGFTFSSYDMSWVRQAPGKGLEWVATISDGGGYIYYSDSVKGRFTISRDNAKNSLYLQMNSLRAEDTAVYYCAREFGKRYALDYWGQGTLVTVSS | 22 |
| HU1210 VH.5a | EVQLVESGGGLVQPGGSLRLSCAASGFTFSSYDMSWVRQAPGKGLEWVATISDGGGYIYYSDSVKGRFTISRDNAKNSLYLQMNSLRAEDTAVYICAREFGKRYALDYWGQGTLVTVSS | 23 |
| HU1210 VH.5b | EVQLVESGGGLVQPGGSLRLSCAASGFTFSSYDMSWVRQAPGKGLEWVATISDGGGYIYYSDSVKGRFTISRDNAKNSLYLQMNSLRAEDTAVYICAREFGKRYALDYWGQGTTVTVSS | 24 |
| HU1210 VH.5c | EVQLVESGGGLVQPGGSLRLSCAASGFTFSSYDMSWVRQAPGKGLEWVATISDGGGYIYYSDSVKGRFTISRDNARNNLYLQMNSLRAEDTAVYICAREFGKRYALDYWGQGTLVTVSS | 25 |
| HU1210 VH.5d | EVQLVESGGGLVQPGGSLRLSCAASGFTFSSYDMSWVRQTPEKSLEWVATISDGGGYIYYSDSVKGRFTISRDNARNNLYLQMNSLRAEDTAVYICAREFGKRYALDYWGQGTLVTVSS | 26 |
| HL1210-VK | DIVMTQSHKFMSTSVGDRVSISCKASQDVTPAVAWYQQKPGQSPKLLIYSTSSRYTGVPDRFTGSGSGTDFTFTISSVQAEDLAVYYCQQHYTTPLTFGAGTKLELK | 27 |
| Hu1210 VK.1 | DIQMTQSPSSLSASVGDRVTITCKASQDVTPAVAWYQQKPGKAPKLLIYSTSSRYTGVPSRFSGSGSGTDFTFTISSLQPEDIATYYCQQHYTTPLTFGQGTKLEIK | 28 |

TABLE 8-continued

Humanized antibody sequences (bold indicates CDR)

| Name | Sequence | SEQ ID NO: |
|---|---|---|
| Hu1210 VK.1a | DIQMTQSPSSLSASVGDRVTITCKASQDVTPAVAWYQQKPGKSPKLLIYS TSSRYTGVPSRFSGSGSGTDFTFTISSLQPEDIATYYCQQHYTTPLTFGQ GTKLEIK | 29 |
| Hu1210 Vk.2 | DIQMTQSPSSLSASVGDRVTITCKASQDVTPAVAWYQQKPGKAPKLLIYS TSSRYTGVPSRFSGSGSGTDFTLTISSLQPEDFATYYCQQHYTTPLTFGQ GTKLEIKR | 30 |
| Hu1210 Vk.2a | DIQMTQSPSSLSASVGDRVTITCKASQDVTPAVAWYQQKPGKAPKLLIYS TSSRYTGVPDRFTGSGSGTDFTLTISSLQPEDFATYYCQQHYTTPLTFGQ GTKLEIKR | 31 |
| Hu1210 Vk.2b | DIQMTQSPSSLSASVGDRVTITCKASQDVTPAVAWYQQKPGQSPKLLIYS TSSRYTGVPDRFTGSGSGTDFTLTISSLQPEDFATYYCQQHYTTPLTFGQ GTKLEIKR | 32 |
| Hu1210 Vk.2c | DIQMTQSPSSLSASVGDRVTISCKASQDVTPAVAWYQQKPGQSPKLLIYS TSSRYTGVPDRFTGSGSGTDFTLTISSLQPEDFATYYCQQHYTTPLTFGQ GTKLEIKR | 33 |
| HL1210 VH | GAGGTGAAGCTGGTGGAGAGCGGCGGAGATCTGGTGAAGCCTGGCGGCAGCCTGAAGCTG AGCTGTGCCGCCAGCGGCTTCACCTTCAGCAGCTACGACATGAGCTGGGTGAGGCAGACC CCCGAGAAGAGCCTGGAGTGGGTGGCCACCATCAGCGATGGCGGCGGCTACATCTACTAC AGCGACAGCGTGAAGGGCAGGTTCACCATCAGCAGGGACAACGCCAAGAACAACCTGTAC CTGCAGATGAGCAGCCTGAGGAGCGAGGACACCGCCCTGTACATCTGCGCCAGGGAGTTC GGCAAGAGGTACGCCCTGGACTACTGGGGACAGGGCACCAGCGTGACCGTGAGCAGC | 34 |
| Hu1210 VH.1 | GAGGTGCAGCTGGTGGAGAGCGGAGGAGGACTGGTGAAGCCCGGAGGCAGCCTGAGACTG AGCTGCGCTGCCAGCGGCTTCACCTTCAGCAGCTACGACATGAGCTGGGTGAGACAGGCC CCTGGCAAAGGCCTGGAGTGGGTGAGCACCATCTCCGATGGCGGCGGCTACATCTATTAC TCCGACAGCGTGAAGGGCAGGTTCACCATCAGCAGGGACAACGCCAAGAACAGCCTGTAC CTGCAGATGAACAGCCTGAGGGCCGAGGACACCGCCGTGTACTACTGCGCCAGGGAGTTC GGCAAAAGGTACGCCCTGGACTACTGGGGCCAGGGCACAACCGTGACCGTGAGCAGC | 35 |
| Hu1210 VH.1a | GAGGTGCAGCTGGTGGAGAGCGGAGGAGGACTGGTGAAGCCCGGAGGCAGCCTGAGACTG AGCTGCGCTGCCAGCGGCTTCACCTTCAGCAGCTACGACATGAGCTGGGTGAGACAGGCC CCTGGCAAAGGCCTGGAGTGGGTGGCCACCATCTCCGATGGCGGCGGCTACATCTATTAC TCCGACAGCGTGAAGGGCAGGTTCACCATCAGCAGGGACAACGCCAAGAACAGCCTGTAC CTGCAGATGAACAGCCTGAGGGCCGAGGACACCGCCGTGTACTACTGCGCCAGGGAGTTC GGCAAAAGGTACGCCCTGGACTACTGGGGCCAGGGCACAACCGTGACCGTGAGCAGC | 36 |
| Hu1210 VH.1b | GAGGTGCAGCTGGTGGAGAGCGGAGGAGGACTGGTGAAGCCCGGAGGCAGCCTGAGACTG AGCTGCGCTGCCAGCGGCTTCACCTTCAGCAGCTACGACATGAGCTGGGTGAGACAGGCC CCTGGCAAAAGCCTGGAGTGGGTGGCCACCATCTCCGATGGCGGCGGCTACATCTATTAC TCCGACAGCGTGAAGGGCAGGTTCACCATCAGCAGGGACAACGCCAAGAACAGCCTGTAC CTGCAGATGAACAGCCTGAGGGCCGAGGACACCGCCGTGTACATCTGCGCCAGGGAGTTC GGCAAAAGGTACGCCCTGGACTACTGGGGCCAGGGCACAACCGTGACCGTGAGCAGC | 37 |
| Hu1210 VH.2 | GAGGTGCAGCTGGTGGAGAGCGGAGGAGGACTGGTGAAGCCCGGAGGCAGCCTGAGACTG AGCTGCGCTGCCAGCGGCTTCACCTTCAGCAGCTACGACATGAGCTGGATCAGACAGGCC CCTGGCAAAGGCCTGGAGTGGGTGAGCACCATCTCCGATGGCGGCGGCTACATCTATTAC TCCGACAGCGTGAAGGGCAGGTTCACCATCAGCAGGGACAACGCCAAGAACAGCCTGTAC CTGCAGATGAACAGCCTGAGGGCCGAGGACACCGCCGTGTACTACTGCGCCAGGGAGTTC GGCAAAAGGTACGCCCTGGACTACTGGGGCCAGGGCACAACCGTGACCGTGAGCAGC | 38 |
| Hu1210 VH.2a | GAGGTGCAGCTGGTGGAGAGCGGAGGAGGACTGGTGAAGCCCGGAGGCAGCCTGAGACTG AGCTGCGCTGCCAGCGGCTTCACCTTCAGCAGCTACGACATGAGCTGGATCAGACAGGCC CCTGGCAAAGGCCTGGAGTGGGTGGCCACCATCTCCGATGGCGGCGGCTACATCTATTAC TCCGACAGCGTGAAGGGCAGGTTCACCATCAGCAGGGACAACGCCAAGAACAGCCTGTAC CTGCAGATGAACAGCCTGAGGGCCGAGGACACCGCCGTGTACTACTGCGCCAGGGAGTTC GGCAAAAGGTACGCCCTGGACTACTGGGGCCAGGGCACAACCGTGACCGTGAGCAGC | 39 |
| Hu1210 VH.2b | GAGGTGCAGCTGGTGGAGAGCGGAGGAGGACTGGTGAAGCCCGGAGGCAGCCTGAGACTG AGCTGCGCTGCCAGCGGCTTCACCTTCAGCAGCTACGACATGAGCTGGGTGAGACAGGCC CCTGGCAAAAGCCTGGAGTGGGTGGCCACCATCTCCGATGGCGGCGGCTACATCTATTAC TCCGACAGCGTGAAGGGCAGGTTCACCATCAGCAGGGACAACGCCAAGAACAGCCTGTAC CTGCAGATGAACAGCCTGAGGGCCGAGGACACCGCCGTGTACATCTGCGCCAGGGAGTTC GGCAAAAGGTACGCCCTGGACTACTGGGGCCAGGGCACAACCGTGACCGTGAGCAGC | 40 |

TABLE 8-continued

Humanized antibody sequences (bold indicates CDR)

| Name | Sequence | SEQ ID NO: |
|---|---|---|
| Hu1210 VH.3 | GAGGTGCAGCTGCTGGAGAGCGGAGGAGGACTGGTGCAACCCGGAGGCAGCCTGAGACTG<br>AGCTGCGCTGCCAGCGGCTTCACCTTCAGCAGCTACGACATGAGCTGGGTGAGACAGGCC<br>CCTGGCAAAGGCCTGGAGTGGGTGAGCACCATCTCCGATGGCGGCGGCTACATCTATTAC<br>TCCGACAGCGTGAAGGGCAGGTTCACCATCAGCAGGGACAACAGCAAGAACACCCTGTAC<br>CTGCAGATGAACAGCCTGAGGGCCGAGGACACCGCCGTGTACTACTGCGCCAGGGAGTTC<br>GGCAAAAGGTACGCCCTGGACTACTGGGGCCAGGGCACAACCGTGACCGTGAGCAGC | 41 |
| Hu1210 VH.3a | GAGGTGCAGCTGCTGGAGAGCGGAGGAGGACTGGTGCAACCCGGAGGCAGCCTGAGACTG<br>AGCTGCGCTGCCAGCGGCTTCACCTTCAGCAGCTACGACATGAGCTGGGTGAGACAGGCC<br>CCTGGCAAAGCCTGGAGTGGGTGGCCACCATCTCCGATGGCGGCGGCTACATCTATTAC<br>TCCGACAGCGTGAAGGGCAGGTTCACCATCAGCAGGGACAACAGCAAGAACACCCTGTAC<br>CTGCAGATGAACAGCCTGAGGGCCGAGGACACCGCCGTGTACATCTGCGCCAGGGAGTTC<br>GGCAAAAGGTACGCCCTGGACTACTGGGGCCAGGGCACAACCGTGACCGTGAGCAGC | 42 |
| Hu1210 VH.4 | GAGGTGCAGCTGGTGGAGAGCGGAGGAGGACTGGTGCAACCCGGAGGCAGCCTGAGACTG<br>AGCTGCGCTGCCAGCGGCTTCACCTTCAGCAGCTACGACATGAGCTGGGTGAGACAGGCC<br>CCTGGCAAAGGCCTGGAGTGGGTGAGCACCATCTCCGATGGCGGCGGCTACATCTATTAC<br>TCCGACAGCGTGAAGGGCAGGTTCACCATCAGCAGGGACAACGCCAAGAACAGCCTGTAC<br>CTGCAGATGAACAGCCTGAGGGATGAGGACACCGCCGTGTACTACTGCGCCAGGGAGTTC<br>GGCAAAAGGTACGCCCTGGACTACTGGGGCCAGGGCACAACCGTGACCGTGAGCAGC | 43 |
| Hu1210 VH.4a | GAGGTGCAGCTGGTGGAGAGCGGAGGAGGACTGGTGCAACCCGGAGGCAGCCTGAGACTG<br>AGCTGCGCTGCCAGCGGCTTCACCTTCAGCAGCTACGACATGAGCTGGGTGAGACAGGCC<br>CCTGGCAAAGGCCTGGAGTGGGTGGCCACCATCTCCGATGGCGGCGGCTACATCTATTAC<br>TCCGACAGCGTGAAGGGCAGGTTCACCATCAGCAGGGACAACGCCAAGAACAGCCTGTAC<br>CTGCAGATGAACAGCCTGAGGGATGAGGACACCGCCGTGTACTACTGCGCCAGGGAGTTC<br>GGCAAAAGGTACGCCCTGGACTACTGGGGCCAGGGCACAACCGTGACCGTGAGCAGC | 44 |
| Hu1210 VH.4b | GAGGTGCAGCTGGTGGAGAGCGGAGGAGGACTGGTGCAACCCGGAGGCAGCCTGAGACTG<br>AGCTGCGCTGCCAGCGGCTTCACCTTCAGCAGCTACGACATGAGCTGGGTGAGACAGGCC<br>CCTGGCAAAGCCTGGAGTGGGTGGCCACCATCTCCGATGGCGGCGGCTACATCTATTAC<br>TCCGACAGCGTGAAGGGCAGGTTCACCATCAGCAGGGACAACGCCAAGAACAGCCTGTAC<br>CTGCAGATGAACAGCCTGAGGGATGAGGACACCGCCGTGTACATCTGCGCCAGGGAGTTC<br>GGCAAAAGGTACGCCCTGGACTACTGGGGCCAGGGCACAACCGTGACCGTGAGCAGC | 45 |
| Hu1210 VH.4c | GAGGTGCAGCTGGTGGAGAGCGGAGGAGGACTGGTGCAACCCGGAGGCAGCCTGAGACTG<br>AGCTGCGCTGCCAGCGGCTTCACCTTCAGCAGCTACGACATGAGCTGGGTGAGACAGGCC<br>CCTGGCAAAAGCCTGGAGTGGGTGGCCACCATCTCCGAAGGCGGCGGCTACATCTATTAC<br>TCCGACAGCGTGAAGGGCAGGTTCACCATCAGCAGGGACAACGCCAAGAACAGCCTGTAC<br>CTGCAGATGAACAGCCTGAGGGATGAGGACACCGCCGTGTACATCTGCGCCAGGGAGTTC<br>GGCAAAAGGTACGCCCTGGACTACTGGGGCCAGGGCACAACCGTGACCGTGAGCAGC | 46 |
| Hu1210 VH.4d | GAGGTGCAGCTGGTGGAGAGCGGAGGAGGACTGGTGCAACCCGGAGGCAGCCTGAGACTG<br>AGCTGCGCTGCCAGCGGCTTCACCTTCAGCAGCTACGACATGAGCTGGGTGAGACAGGCC<br>CCTGGCAAAAGCCTGGAGTGGGTGGCCACCATCTCCGATGCGGGCGGCTACATCTATTAC<br>TCCGACAGCGTGAAGGGCAGGTTCACCATCAGCAGGGACAACGCCAAGAACAGCCTGTAC<br>CTGCAGATGAACAGCCTGAGGGATGAGGACACCGCCGTGTACATCTGCGCCAGGGAGTTC<br>GGCAAAAGGTACGCCCTGGACTACTGGGGCCAGGGCACAACCGTGACCGTGAGCAGC | 47 |
| Hu1210 VH.4e | GAGGTGCAGCTGGTGGAGAGCGGAGGAGGACTGGTGCAACCCGGAGGCAGCCTGAGACTG<br>AGCTGCGCTGCCAGCGGCTTCACCTTCAGCAGCTACGACATGAGCTGGGTGAGACAGGCC<br>CCTGGCAAAAGCCTGGAGTGGGTGGCCACCATCTCCGATGTTGGCGGCTACATCTATTAC<br>TCCGACAGCGTGAAGGGCAGGTTCACCATCAGCAGGGACAACGCCAAGAACAGCCTGTAC<br>CTGCAGATGAACAGCCTGAGGGATGAGGACACCGCCGTGTACATCTGCGCCAGGGAGTTC<br>GGCAAAAGGTACGCCCTGGACTACTGGGGCCAGGGCACAACCGTGACCGTGAGCAGC | 48 |
| Hu1210 VH.5 | GAGGTGCAGCTGGTGGAGTCCGGAGGAGGCCTGGTGCAACCTGGAGGCTCCCTGAGGCTG<br>TCCTGTGCCGCTTCCGGCTTCACCTTCAGCTCCTACGATATGAGCTGGGTGAGGCAGGCT<br>CCTGGAAAGGGCCTGGAGTGGGTGGCCACCATCTCCGACGGAGGCGGCTACATCTACTAC<br>TCCGACTCCGTGAAGGGCAGGTTCACCATCTCCCGGGACAACGCCAAGAACTCCCTGTAC<br>CTGCAGATGAACTCTCTCAGGGCTGAGGACACCGCCGTGTATTACTGCGCCAGGGAGTTT<br>GGCAAGAGGTACGCCCTGGATTACTGGGGCCAGGGCACACTGGTGACAGTGAGCTCC | 49 |
| Hu1210 VH.5a | GAGGTGCAGCTGGTGGAGTCCGGAGGAGGCCTGGTGCAACCTGGAGGCTCCCTGAGGCTG<br>TCCTGTGCCGCTTCCGGCTTCACCTTCAGCTCCTACGATATGAGCTGGGTGAGGCAGGCT<br>CCTGGAAAGGGCCTGGAGTGGGTGGCCACCATCTCCGACGGAGGCGGCTACATCTACTAC<br>TCCGACTCCGTGAAGGGCAGGTTCACCATCTCCCGGGACAACGCCAAGAACTCCCTGTAC<br>CTGCAGATGAACTCTCTCAGGGCTGAGGACACCGCCGTGTATATCTGCGCCAGGGAGTTT<br>GGCAAGAGGTACGCCCTGGATTACTGGGGCCAGGGCACACTGGTGACAGTGAGCTCC | 50 |

TABLE 8-continued

Humanized antibody sequences (bold indicates CDR)

| Name | Sequence | SEQ ID NO: |
|---|---|---|
| Hu1210 VH.5b | GAGGTGCAGCTGGTGGAGTCCGGAGGAGGCCTGGTGCAACCTGGAGGCTCCCTGAGGCTG<br>TCCTGTGCCGCTTCCGGCTTCACCTTCAGCTCCTACGATATGAGCTGGGTGAGGCAGGCT<br>CCTGGAAAGGGCCTGGAGTGGGTGGCCACCATCTCCGACGGAGGCGGCTACATCTACTAC<br>TCCGACTCCGTGAAGGGCAGGTTCACCATCTCCCGGGACAACGCCAAGAACAACCTGTAC<br>CTGCAGATGAACTCTCTCAGGGCTGAGGACACCGCCGTGTATATCTGCGCCAGGGAGTTT<br>GGCAAGAGGTACGCCCTGGATTACTGGGGCCAGGGCACACTGGTGACAGTGAGCTCC | 51 |
| Hu1210 VH.5c | GAGGTGCAGCTGGTGGAGTCCGGAGGAGGCCTGGTGCAACCTGGAGGCTCCCTGAGGCTG<br>TCCTGTGCCGCTTCCGGCTTCACCTTCAGCTCCTACGATATGAGCTGGGTGAGGCAGACC<br>CCTGAGAAGAGCCTGGAGTGGGTGGCCACCATCTCCGACGGAGGCGGCTACATCTACTAC<br>TCCGACTCCGTGAAGGGCAGGTTCACCATCTCCCGGGACAACGCCAAGAACAACCTGTAC<br>CTGCAGATGAACTCTCTCAGGGCTGAGGACACCGCCGTGTATATCTGCGCCAGGGAGTTT<br>GGCAAGAGGTACGCCCTGGATTACTGGGGCCAGGGCACACTGGTGACAGTGAGCTCC | 52 |
| Hu1210 VH.5d | GAGGTGCAGCTGGTGGAGTCCGGAGGAGGCCTGGTGCAACCTGGAGGCTCCCTGAGGCTG<br>TCCTGTGCCGCTTCCGGCTTCACCTTCAGCTCCTACGATATGAGCTGGGTGAGGCAGGCT<br>CCTGGAAAGGGCCTGGAGTGGGTGGCCACCATCTCCGACGGAGGCGGCTACATCTACTAC<br>TCCGACTCCGTGAAGGGCAGGTTCACCATCTCCCGGGACAACGCCAAGAACTCCCTGTAC<br>CTGCAGATGAACTCTCTCAGGGCTGAGGACACCGCCGTGTATATCTGCGCCAGGGAGTTT<br>GGCAAGAGGTACGCCCTGGATTACTGGGGCCAGGGCACAACCGTGACAGTGAGCTCC | 53 |
| HL1210 VK | GACATCGTGATGACCCAGAGCCACAAGTTCATGAGCACCAGCGTGGGCGATAGGGTGAGC<br>ATCAGCTGCAAGGCCAGCCAGGATGTGACCCCTGCCGTGGCCTGGTACCAGCAGAAGCCC<br>GGCCAGAGCCCCAAGCTGCTGATCTACAGCACCAGCAGCAGGTACACCGGCGTGCCCGAC<br>AGGTTCACAGGAAGCGGCAGCGGCACCGACTTCACCTTCACCATCAGCAGCGTGCAGGCC<br>GAGGACCTGGCCGTGTACTACTGCCAGCAGCACTACACCACCCCTCTGACCTTCGGCGCC<br>GGCACCAAGCTGGAGCTGAAG | 54 |
| Hu1210 VK.1 | GACATCCAGATGACCCAGAGCCCTAGCAGCCTGAGCGCTAGCGTGGGCGACAGGGTGACC<br>ATCACCTGCAAGGCCAGCCAGGATGTGACCCCTGCCGTGGCCTGGTACCAGCAGAAGCCC<br>GGCAAGGCCCCCAAGCTGCTGATCTACAGCACCAGCAGCAGGTACACCGGCGTGCCCAGC<br>AGGTTTAGCGGAAGCGGCAGCGGCACCGACTTCACCTTCACCATCAGCAGCCTGCAGCCC<br>GAGGACATCGCCACCTACTACTGCCAGCAGCACTACACCACCCCTCTGACCTTCGGCCAG<br>GGCACCAAGCTGGAGATCAAG | 55 |
| Hu1210 VK.1a | GACATCCAGATGACCCAGAGCCCTAGCAGCCTGAGCGCTAGCGTGGGCGACAGGGTGACC<br>ATCACCTGCAAGGCCAGCCAGGATGTGACCCCTGCCGTGGCCTGGTACCAGCAGAAGCCC<br>GGCAAGTCCCCCAAGCTGCTGATCTACAGCACCAGCAGCAGGTACACCGGCGTGCCCAGC<br>AGGTTTAGCGGAAGCGGCAGCGGCACCGACTTCACCTTCACCATCAGCAGCCTGCAGCCC<br>GAGGACATCGCCACCTACTACTGCCAGCAGCACTACACCACCCCTCTGACCTTCGGCCAG<br>GGCACCAAGCTGGAGATCAAG | 56 |
| Hu1210 VK.2 | GACATTCAGATGACCCAGTCCCCTAGCAGCCTGTCCGCTTCCGTGGGCGACAGGGTGACC<br>ATCACCTGCAAGGCCAGCCAGGACGTGACACCTGCTGTGGCCTGGTATCAACAGAAGCCT<br>GGCAAGGCTCCTAAGCTCCTGATCTACAGCACATCCTCCCGGTACACCGGAGTGCCCTCC<br>AGGTTTAGCGGCAGCGGCTCCGGCACCGATTTCACCCTGACCATTTCCTCCCTGCAGCCC<br>GAGGACTTCGCCACCTACTACTGCCAGCAGCACTACACCACACCCCTGACCTTCGGCCAG<br>GGCACCAAGCTGGAGATCAAGCGG | 57 |
| Hu1210 VK.2a | GACATTCAGATGACCCAGTCCCCTAGCAGCCTGTCCGCTTCCGTGGGCGACAGGGTGACC<br>ATCACCTGCAAGGCCAGCCAGGACGTGACACCTGCTGTGGCCTGGTATCAACAGAAGCCT<br>GGCAAGGCTCCTAAGCTCCTGATCTACAGCACATCCTCCCGGTACACCGGAGTGCCCGAC<br>AGGTTTACCGGCAGCGGCTCCGGCACCGATTTCACCCTGACCATTTCCTCCCTGCAGCCC<br>GAGGACTTCGCCACCTACTACTGCCAGCAGCACTACACCACACCCCTGACCTTCGGCCAG<br>GGCACCAAGCTGGAGATCAAGCGG | 58 |
| Hu1210 VK.2b | GACATTCAGATGACCCAGTCCCCTAGCAGCCTGTCCGCTTCCGTGGGCGACAGGGTGACC<br>ATCACCTGCAAGGCCAGCCAGGACGTGACACCTGCTGTGGCCTGGTATCAACAGAAGCCT<br>GGCCAGAGCCCTAAGCTCCTGATCTACAGCACATCCTCCCGGTACACCGGAGTGCCCGAC<br>AGGTTTACCGGCAGCGGCTCCGGCACCGATTTCACCCTGACCATTTCCTCCCTGCAGCCC<br>GAGGACTTCGCCACCTACTACTGCCAGCAGCACTACACCACACCCCTGACCTTCGGCCAG<br>GGCACCAAGCTGGAGATCAAGCGG | 59 |
| Hu1210 VK.2c | GACATTCAGATGACCCAGTCCCCTAGCAGCCTGTCCGCTTCCGTGGGCGACAGGGTGACC<br>ATCAGCTGCAAGGCCAGCCAGGACGTGACACCTGCTGTGGCCTGGTATCAACAGAAGCCT<br>GGCCAGAGCCCTAAGCTCCTGATCTACAGCACATCCTCCCGGTACACCGGAGTGCCCGAC<br>AGGTTTACCGGCAGCGGCTCCGGCACCGATTTCACCCTGACCATTTCCTCCCTGCAGCCC<br>GAGGACTTCGCCACCTACTACTGCCAGCAGCACTACACCACACCCCTGACCTTCGGCCAG<br>GGCACCAAGCTGGAGATCAAGCGG | 60 |

The humanized VH and VK genes were produced synthetically and then respectively cloned into vectors containing the human gamma 1 and human kappa constant domains. The pairing of the human VH and the human VK created the 40 humanized antibodies (see Table 9).

antibodies can high efficiently bind to PD-L1 expressed on mammalian cells, which was comparable with chimeric antibody.

To explore the binding kinetics of the humanized antibody, this example performed the affinity ranking by using Octet Red 96. As shown in Table 10, hu1210-3, hu1210-8, hu1210-9, hu1210-14, hu1210-17, hu1210-1 and Hu1210-22 show better affinity, which is comparable with chimeric antibody.

TABLE 9

Humanized antibodies with their VH an VL regions

| Vk | Hu1210 VH.1 | Hu1210 VH.1a | Hu1210 VH.1b | Hu1210 VH.2 | Hu1210 VH.2a | Hu1210 VH 2.b | Hu1210 VH |
|---|---|---|---|---|---|---|---|
| Hu1210 Vk.1 | Hu1210-1 | Hu1210-2 | Hu1210-3 | Hu1210-4 | Hu1210-5 | | |
| Hu1210 Vk.1a | Hu1210-7 | Hu1210-8 | Hu1210-9 | Hu1210-10 | Hu1210-11 | | |
| Hu1210 Vk | | | | | | | H1210 chimera |

| Vk | Hu1210 VH.3 | Hu1210 VH.3a | Hu1210 VH.4 | Hu1210 VH.4a | Hu1210 VH.4b |
|---|---|---|---|---|---|
| Hu1210 Vk.1 | Hu1210-13 | Hu1210-14 | Hu1210-15 | Hu1210-16 | Hu1210-17 |
| Hu1210 Vk.1a | Hu1210-18 | Hu1210-19 | Hu1210-20 | Hu1210-21 | Hu1210-22 |

| VK | Hu1210 VH.5 | HU1210 VH.5a | HU1210 VH.5b | HU1210 VH.5c | HU1210 VH.5d |
|---|---|---|---|---|---|
| Hu1210 Vk.2 | Hu1210-23 | Hu1210-27 | Hu1210-31 | Hu1210-32 | Hu1210-36 |
| Hu1210 Vk.2a | Hu1210-24 | Hu1210-28 | | Hu1210-33 | Hu1210-37 |
| Hu1210 Vk.2b | Hu1210-25 | Hu1210-29 | | Hu1210-34 | Hu1210-38 |
| Hu1210 Vk.2c | Hu1210-26 | Hu1210-30 | | Hu1210-35 | Hu1210-39 |

| Vk | Hu1210 VH.4c | Hu1210 VH.4d | Hu1210 VH.4e |
|---|---|---|---|
| Hu1210 Vk.1 | Hu1210-40 | Hu1210-41 | Hu1210-42 |

Example 7: The Antigen Binding Properties of Humanized PD-L1 Antibodies

Binding Property to Recombinant Human PD-L1

Figure 6:
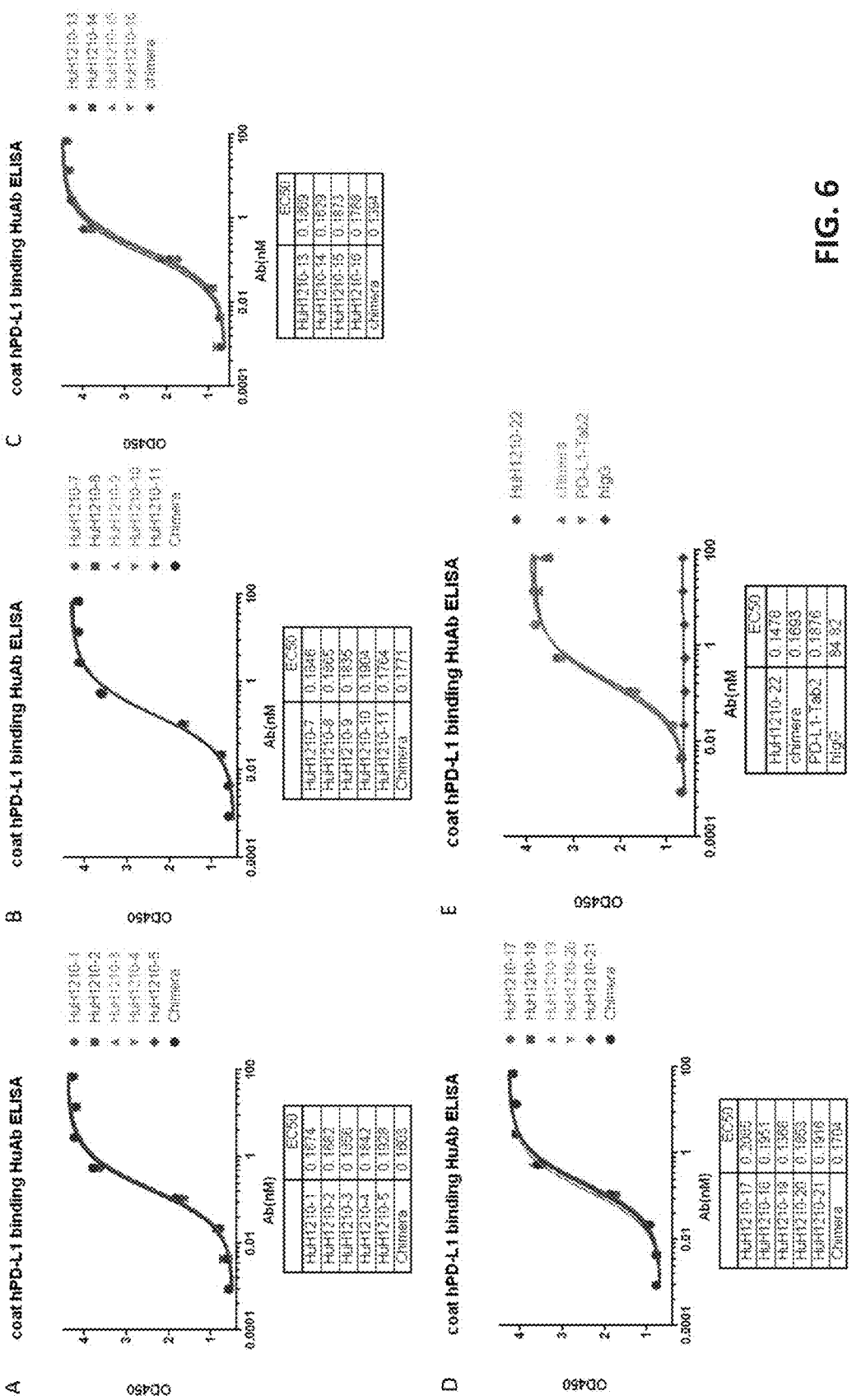
FIG. 6 shows that all tested humanized antibodies had comparable binding efficacy to human PD-L1 in contact to chimeric antibody.

To evaluate the antigen binding activity, the humanized antibodies were subjected to ELISA test. Briefly, microtiter plates were coated with human PD-L1-Fc protein at 0.1 µg/ml in PBS, 100 µl/well at 4° C. overnight, then blocked with 100 µl/well of 5% BSA. Five-fold dilutions of humanized antibodies starting from 10 µg/ml were added to each well and incubated for 1-2 hours at RT. The plates were washed with PBS/Tween and then incubate with goat-anti-mouse IgG antibody conjugated with Horse Radish Peroxidase (HRP) for 1 hour at RT. After washing, the plates were developed with TMB substrate and analyzed by spectrophotometer at OD 450-630 nm. As shown in FIG. 6, all the humanized antibodies show comparable binding efficacy to human PD-L1 in contact to chimeric antibody.

Binding Property to Mammalian Expressed Human PD-L1

Figure 7:
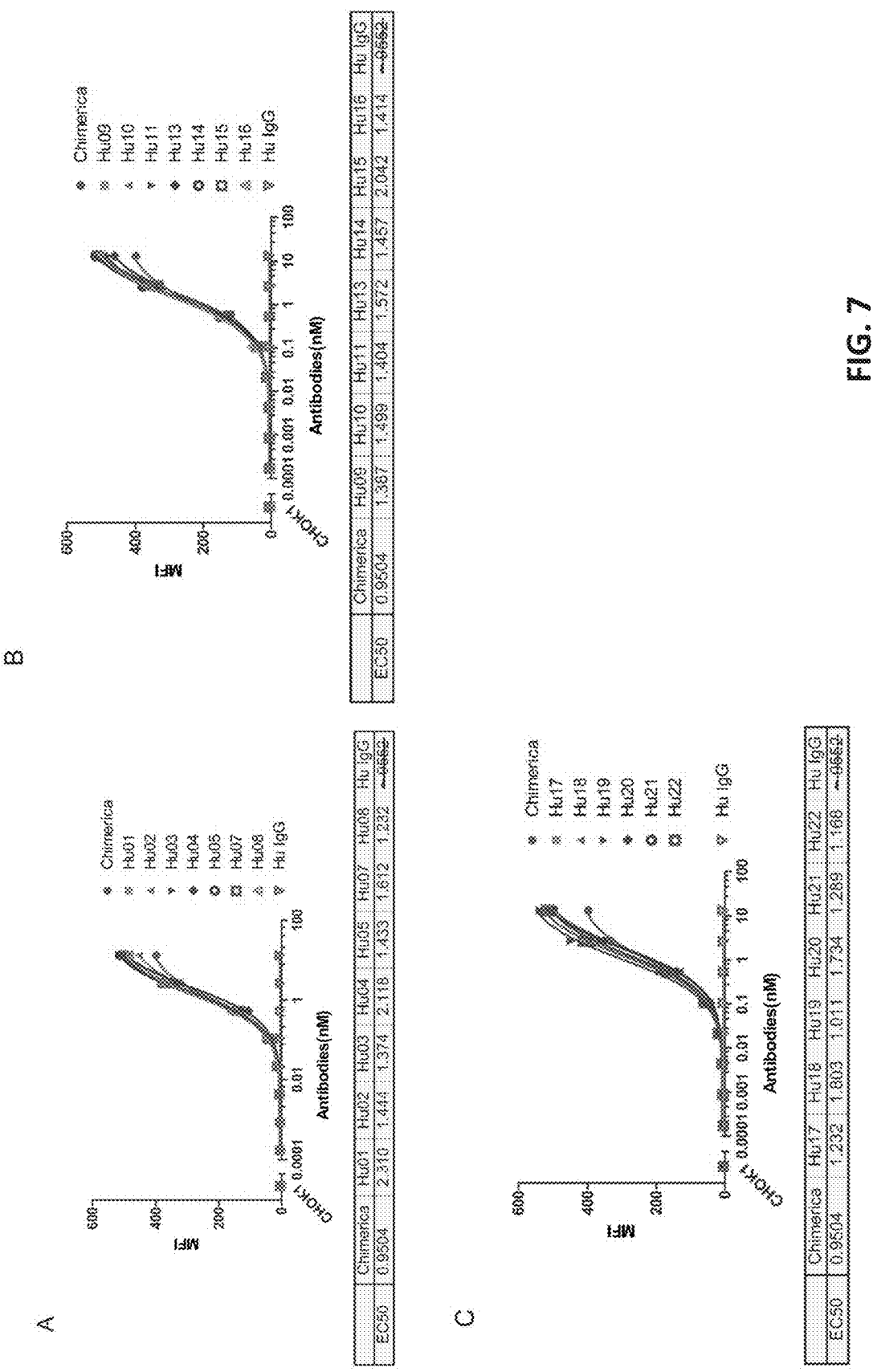
FIG. 7 shows that all tested humanized antibodies can high efficiently bind to PD-L1 expressed on mammalian cells, comparable with chimeric antibody.

To evaluate the antigen binding property, the humanized antibodies were analyzed for its binding to mammalian expressed PD-L1 by FACS. Briefly, PDL1-CHOK1 cells were firstly incubated with 5-fold serious diluted humanized antibodies starting at 2 µg/ml at RT for 1 hour. After wash by FACS buffer (PBS with 2% FBS), the alexa 488-anti-human IgG antibody was added to each well and incubated at RT for 1 hour. The MFI of Alexa 488 were evaluated by FACSAriaIII. As shown in the FIG. 7, all the humanized

TABLE 10

Affinity ranking of humanized antibodies

| Antibody | KD (M) | kon (1/Ms) | kdis (1/s) |
|---|---|---|---|
| Hu1210 (mIgG) | 7.16E−09 | 3.94E+05 | 2.83E−03 |
| H1210 chimera | 1.07E−09 | 1.62E+05 | 1.73E−04 |
| Hu1210-1 | 4.25E−09 | 7.10E+04 | 3.02E−04 |
| Hu1210-2 | 3.23E−09 | 7.78E+04 | 2.51E−04 |
| Hu1210-3 | 2.64E−09 | 8.62E+04 | 2.28E−04 |
| Hu1210-4 | 7.68E−09 | 7.12E+04 | 5.46E−04 |
| Hu1210-5 | 4.83E−09 | 7.93E+04 | 3.83E−04 |
| Hu1210-7 | 4.78E−09 | 8.45E+04 | 4.04E−04 |
| Hu1210-8 | 1.64E−09 | 7.72E+04 | 1.27E−04 |
| Hu1210-9 | 2.33E−09 | 8.37E+04 | 1.95E−04 |
| Hu1210-10 | 7.03E−09 | 8.59E+04 | 6.04E−04 |
| Hu1210-11 | 4.18E−09 | 7.54E+04 | 3.15E−04 |
| Hu1210-13 | 4.36E−09 | 8.38E+04 | 3.66E−04 |
| Hu1210-14 | 2.34E−09 | 8.41E+04 | 1.97E−04 |
| Hu1210-15 | 4.45E−09 | 7.87E+04 | 3.50E−04 |
| Hu1210-16 | 3.14E−09 | 8.41E+04 | 2.64E−04 |
| Hu1210-17 | 2.20E−09 | 8.17E+04 | 1.80E−04 |
| Hu1210-18 | 4.50E−09 | 7.92E+04 | 3.57E−04 |
| Hu1210-19 | 2.50E−09 | 9.03E+04 | 2.25E−04 |
| Hu1210-20 | 4.51E−09 | 8.87E+04 | 4.00E−04 |

TABLE 10-continued

Affinity ranking of humanized antibodies

| Antibody | KD (M) | kon (1/Ms) | kdis (1/s) |
|---|---|---|---|
| Hu1210-21 | 3.12E−09 | 9.39E+04 | 2.93E−04 |
| Hu1210-22 | 2.56E−09 | 9.00E+04 | 2.30E−04 |

Full Kinetic Affinity of Humanized Antibodies by Biacore®

The binding of the humanized antibodies to recombinant PD-L1 protein (human PD-L1-his taq) was tested by BIACORE™ using a capture method. The HL1210-3 mouse mAb were captured using anti-mouse Fc antibody coated on a CM5 chip. A series dilution of human PD-L1-his taq protein was injected over captured antibody for 3 mins at a flow rate of 25 µg/ml. The antigen was allowed to dissociate for 900 s. All the experiment were carried out on a Biacore T200. Data analysis was carried out using Biacore T200 evaluation software and is shown in Table 11 below.

TABLE 11

Affinity by Biacore

| Antibody | ka (1/Ms) | kd (1/s) | KD (M) |
|---|---|---|---|
| Hu1210-8 | 9.346E+4 | 7.169E−5 | 7.671E−10 |
| Hu1210-9 | 9.856E+4 | 4.528E−5 | 4.594E−10 |
| Hu1210-14 | 1.216E+5 | 5.293E−5 | 4.352E−10 |
| Hu1210-16 | 9.978E+4 | 6.704E−5 | 6.720E−10 |
| Hu1210-17 | 1.101E+5 | 2.128E−5 | 1.933E−10 |
| Hu1210-28 | 1.289E+5 | 1.080E−4 | 8.378E−10 |
| Hu1210-31 | 1.486E+5 | 1.168E−4 | 7.862E−10 |
| Hu1210-36 | 1.461E+5 | 7.852E−5 | 5.376E−10 |
| Hu1210-40 | 8.77E+04 | 1.31E−04 | 1.49E−09 |
| Hu1210-41 | 9.17E+04 | 3.46E−05 | 3.78E−10 |
| Hu1210-42 | 8.68E+04 | 7.53E−05 | 8.67E−10 |
| 1210 Chimera | 1.236E+5 | 3.265E−5 | 2.642E−10 |

Cross Species Activity

Figure 8:
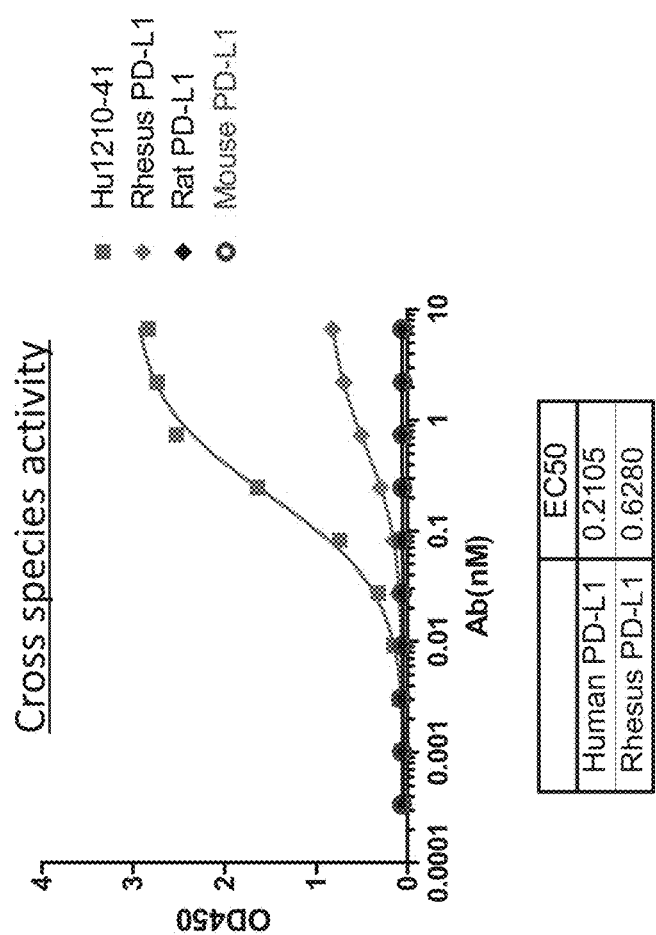
FIG. 8 shows that humanized antibody Hu1210-41 can bind to rhesus PD-L1 with lower affinity and cannot bind to rat and mouse PD-L1.

To evaluate the binding of humanized antibodies to huPD-L1, Mouse PD-L1, Rat PD-L1, Rhesus PD-L1, the antibodies were performed for the ELISA testing. Briefly, microtiter plates were coated with human, mouse, rat and rhesus PD-L1-Fc protein at 1 µg/ml in PBS, 100 µl/well at 4° C. overnight, then blocked with 100 µl/well of 5% BSA. Three-fold dilutions of humanized antibodies starting from 1 µg/ml were added to each well and incubated for 1-2 hours at RT. The plates were washed with PBS/Tween and then incubate with goat-anti-mouse IgG antibody conjugated with Horse Radish Peroxidase (HRP) for 1 hour at RT. After washing, the plates were developed with TMB substrate and analyzed by spectrophotometer at OD 450-630 nm. The Hu1210-41 antibody can bind to rhesus PD-L1 with lower affinity and cannot bind to rat and mouse PD-L1 (FIG. 8).

| | Human | Rhesus | Rat | Mouse |
|---|---|---|---|---|
| EC50 | 0.215 nM | 0.628 nM | No binding | No binding |

Family Member Specificity

Figure 9:
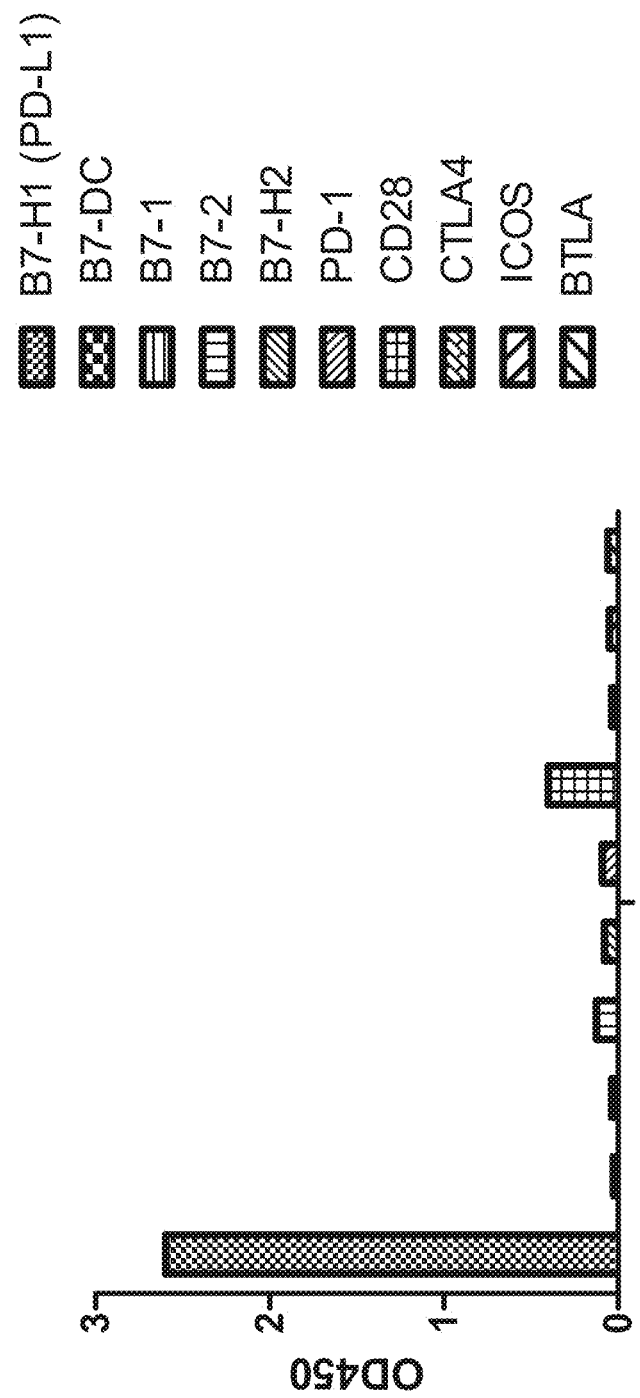
FIG. 9 shows that Hu1210-41 antibody can only specifically binding to B7-H1 (PD-L1), not B7-DC, B7-1, B7-2, B7-H2, PD-1, CD28, CTLA4, ICOS and BTLA.

To evaluate the binding of humanized anti-PD-L1 antibody to human B7 family and other immune checkpoint, the antibody was evaluate for its binding to B7-H1 (PD-L1), B7-DC, B7-1, B7-2, B7-H2, PD-1, CD28, CTLA4, ICOS and BTLA by ELISA. As shown in FIG. 9, the Hu1210-41 antibody can only specifically binding to B7-H1 (PD-L1).

Example 8: Humanized Antibodies Blocked Activity of Human PD-L1 to PD-1

Cell Based Receptor Blocking Assay

To evaluate the blocking effect of humanized antibodies on human PD-L1 expressed on mammalian cells to bind to its receptor PD-1, the FACS-based receptor blocking assay was employed. Briefly, PDL1-CHOK1 cells were firstly incubated with 3-fold serious diluted HL1210-3 mouse mAb starting at 20 µg/ml at RT for 1 hour. After wash by FACS buffer (PBS with 2% FBS), the biotin-labeled huPD-1 were added to each well and incubated at RT for 1 hour. Then, the Streptavidin-PE were added to each well for 0.5 hour post twice wash with FACS buffer. The mean florescence intensity (MFI) of PE were evaluated by FACSAriaIII.

% of inhibition=(1−MFI of testing antibody/MFI of vehicle contorl)×100%

As shown in Table 12 below, Hu1210-3, Hu1210-9, Hu1210-8, Hu1210-14, Hu1210-17, Hu1210-19 and Hu1210-22 antibodies show comparable efficacy with chimeric antibody to blocking the binding of PD-L1 to PD-1.

TABLE 12

PD-1 receptor blocking assay

| | Bio-PD1(30 µg/ml) | |
|---|---|---|
| | TOP | EC50 |
| H1210 chimera | 87.16 | 3.961 |
| Hu1210-8 | 86.35 | 4.194 |
| Hu1210-9 | 85.7 | 4.038 |
| Hu1210-16 | 88.02 | 5.436 |
| Hu1210-17 | 80.88 | 4.424 |
| Hu1210-3 | 84.28 | 3.693 |
| Hu1210-14 | 79.56 | 3.572 |
| Hu1210-19 | 87.45 | 4.52 |
| Hu1210-22 | 85.83 | 4.505 |
| Hu1210-27 | 103.9 | 11.48 |
| Hu1210-31 | 92.91 | 6.179 |
| Hu1210-36 | 91.75 | 8.175 |

Receptor Blocking Assay by Using Recombinant Human PD-L1

Figure 10:
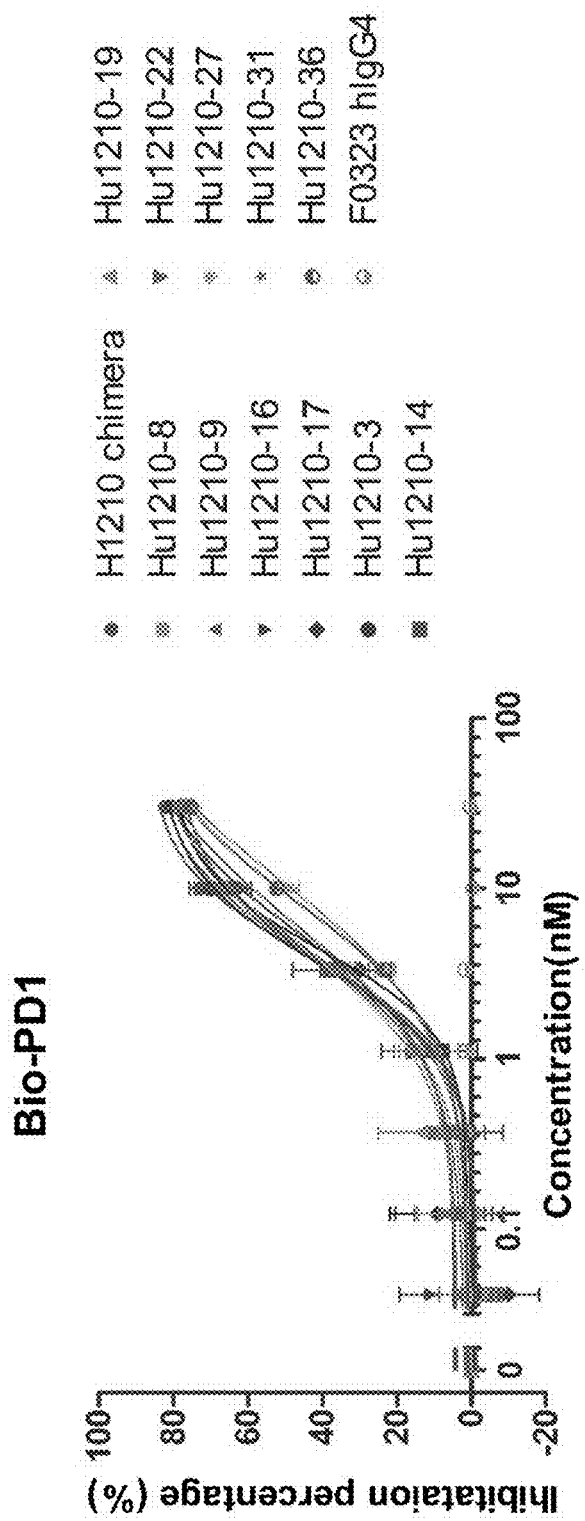
FIG. 10 shows that Hu1210-41 can efficiently inhibit the binding of human PD-L1 to human PD1 and B7-1.
Figure 11:
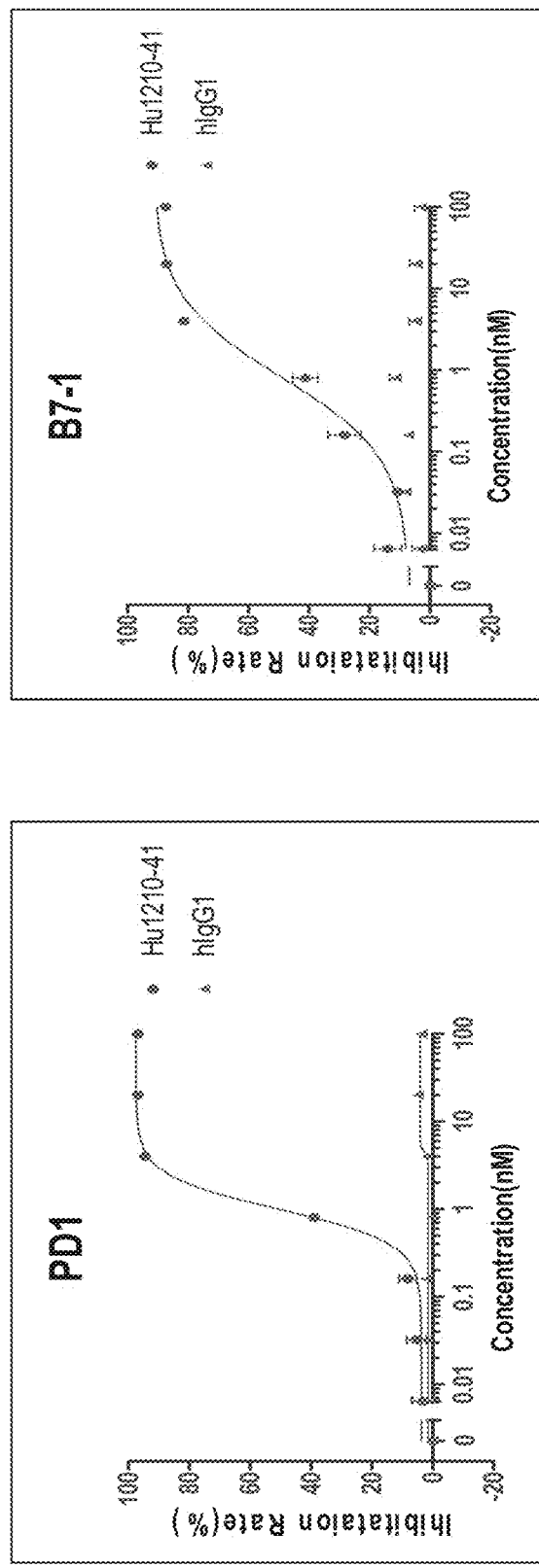
FIG. 11 shows that Hu1210-41 can efficiently inhibit the binding of human PD-L1 to human PD1 and B7-1.

There are two receptors i.e. PD-1 and B7-1 for human PD-L1. To explore the blocking property of humanized PD-L1 antibody to these two proteins, the protein based receptor blocking assay was employed here. Briefly, microtiter plates were coated with human PD-L1-Fc protein at 1 µg/ml in PBS, 100 µl/well at 4° C. overnight, then blocked with 200 µl/well of 5% BSA at 37° C. for 2 hr. 50 µl biotin-labeled human PD-1-Fc or B7-1vprotein and 5-fold dilutions of PD-L1 antibodies starting from 100 nM at 50 µl were added to each well and incubated for 1 hour at 37° C. The plates were washed with PBS/Tween and then incubate with Streptavidin-HRP for 1 hour at 37° C. After washing, the plates were developed with TMB substrate and analyzed by spectrophotometer at OD 450 nm. As shown in FIGS. 10 and 11, Hu1210-41 can efficiently inhibit the binding of human PD-L1 to human PD1 and B7-1.

Example 9: Humanized Antibody Promoted Human T Cell Immune Response

Mixed Lymphocyte Reaction Assay

To evaluate the in vitro function of humanized antibodies, the response of human T cells assessed in a mixed lymphocyte reaction setting. Human DCs were differentiated from CD14+ monocytes in the presence of GM-CSF and IL-4 for 7 days. CD4+ T cells isolated from another donor were then co-cultured with the DCs and serial dilutions of anti-PD-L1 blocking antibody. At day 5 post-inoculation, the culture supernatant was assayed for IL-2 and IFNγ production. The results indicated that the Hu1210-8, Hu1210-9, Hu1210-16 and Hu1210-17 antibodies can dose-dependently promote IL-2 and IFNγ production, suggesting anti-PD-L1 antibodies can promote human T cell response.

CMV Recall Assay

Figure 12:
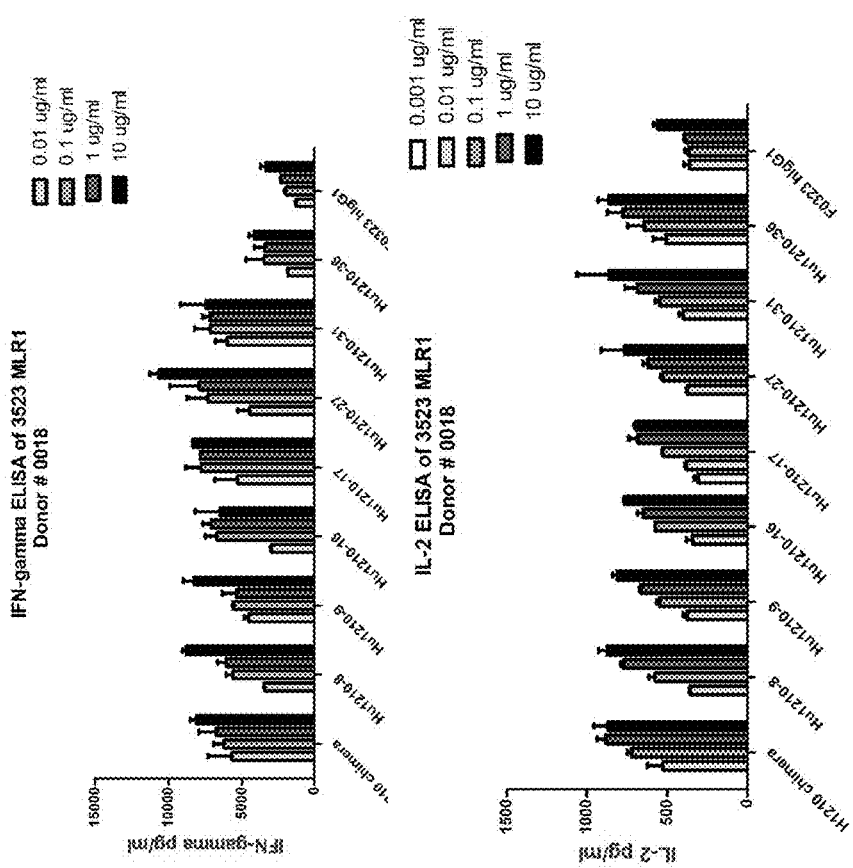
FIG. 12 shows that the Hu1210-8, Hu1210-9, Hu1210-16, Hu1210-17, Hu1210-21 and Hu1210-36 humanized antibodies can dose dependently promote the IFNγ and IL-2 production in mix lymphocyte reaction.
Figure 13:
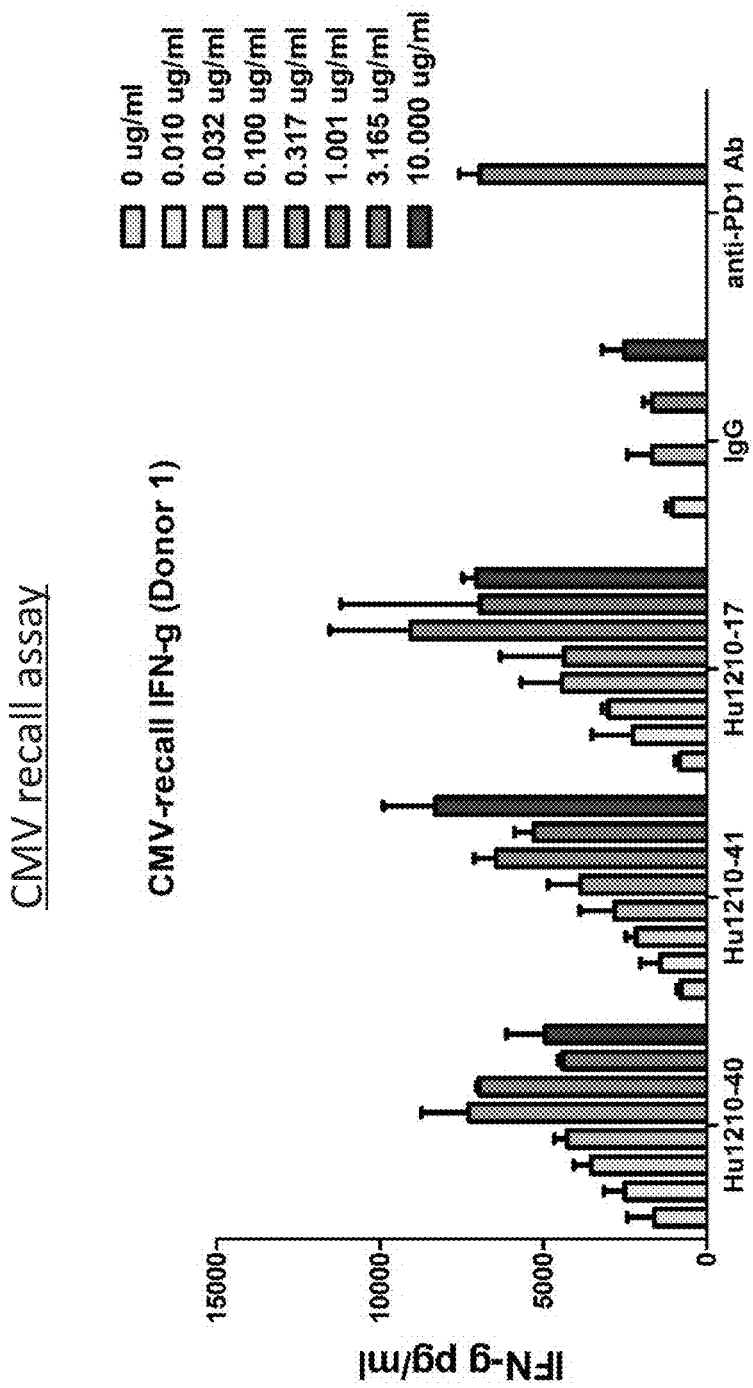
FIG. 13 shows that the Hu1210-40, Hu1210-41 and Hu1210-17 humanized antibodies can dose dependently promote the IFNγ production in CMV recall assay.

To evaluate the in vitro function of humanized antibodies, the response of human T cells assessed in CMV recall assay. Human PBMCs were stimulated with 1 μg/ml CMV antigen in the presence of serious diluted humanized antibodies. As shown in FIGS. 12 and 13 the Hu1210-40, Hu1210-41 and Hu1210-17 can dose dependently promote the IFNγ production.

Example 10: Tumor Growth Inhibition by Anti-PD-L1 mAb

Figure 14:
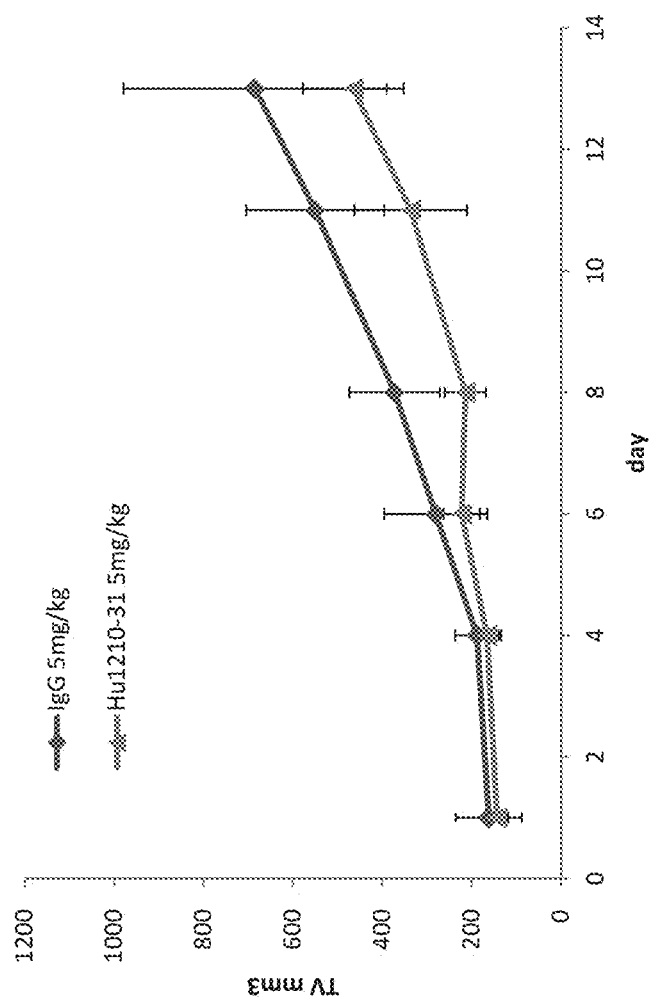
FIG. 14 shows that Hu1210-31 can inhibit the tumor growth by 30% at 5 mg/kg in HCC827-NSG-xenograft model.
Figure 15:
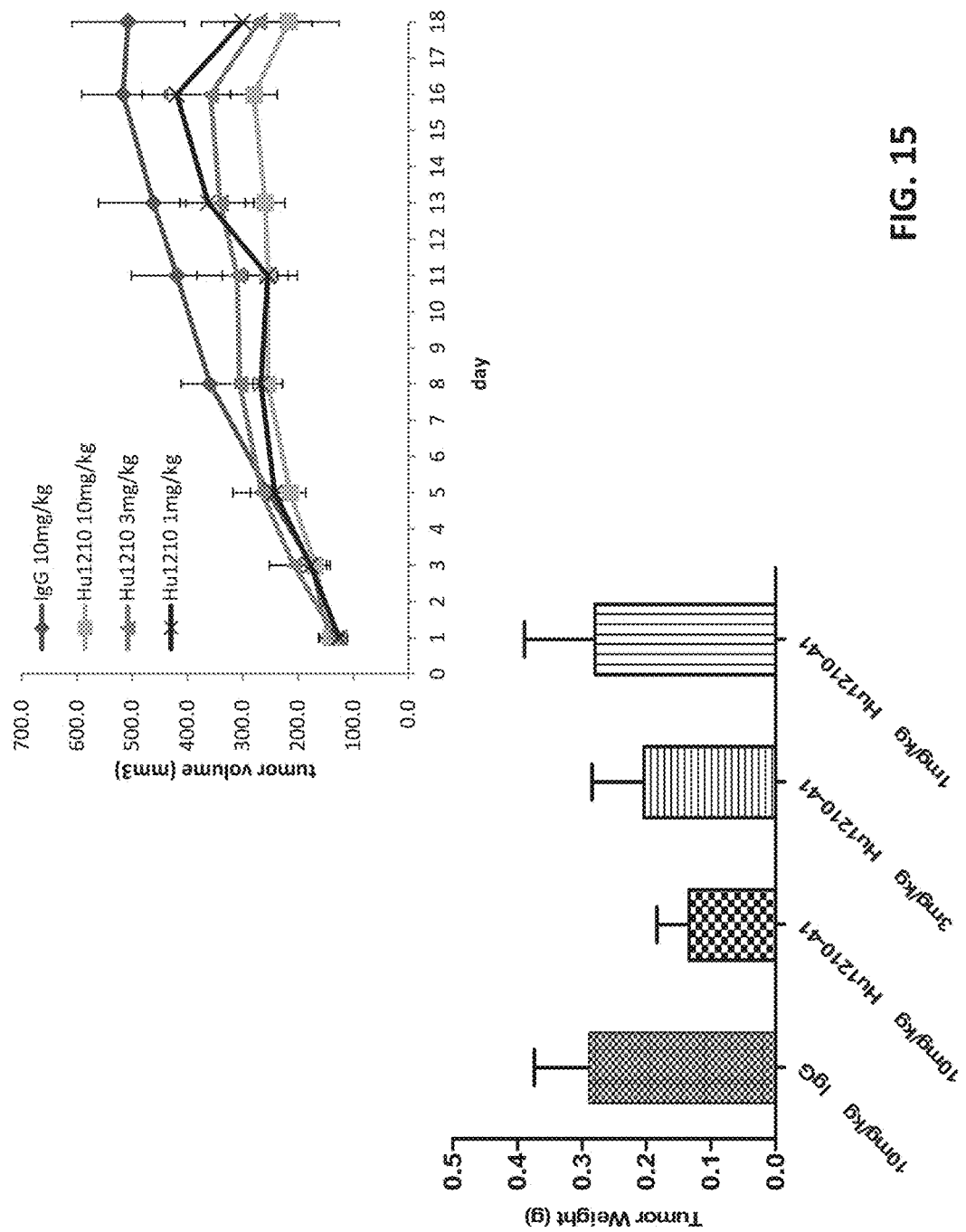
FIG. 15 shows that Hu1210-41 antibody can dose-dependently inhibit the tumor growth in HCC827-NSG-xenograft model, while the tumor weight was also dose-dependently suppressed by Hu1210-41 antibody.

Cells from the human lung adenocarcinoma cell line HCC827 will be grafted into NOD scid gamma (NSG) mice. NSG mice are NOD scid gamma deficient and the most immunodeficient mice making them ideal recipients for human tumor cell and PBMC grafting. 10 days post-graft, human PBMCs will be transplanted into the tumor-bearing mice. Approximately 20 days post-graft, once the tumor volume has reached 100-150 mm³, PD-L1 antibody will be administered to the mice every other day at 5 mg/kg. Tumor volume will be monitored every other day in conjunction with antibody administration. As shown in FIG. 14, Hu1210-31 can inhibit the tumor growth by 30% at 5 mg/kg. Hu1210-41 antibody can dose-dependently inhibit the tumor growth, while the tumor weight was also dose-dependently suppressed by Hu1210-41 antibody (FIG. 15).

Example 11. Computer Simulation of Further Variation and Optimization of the Humanized Antibodies It was contemplated that certain amino acid residues within the CDR regions or the framework regions could be changed to further improve or retain the activity and/or stability of the antibodies. Variants were tested, with a computational tool (VectorNTI, available at www.ebi.ac.uk/tools/msa/clustalo/), with respect to their structural, conformational and functional properties, and those (within the CDR regions) that showed promises are listed in the tables blow.

TABLE 13

VH and VL CDRs and their variants suitable for inclusion in humanized antibodies

| Name | Sequence | SEQ ID NO: |
|---|---|---|
| VH CDR1 | SYDMS | 1 |
| | TYDMS | 61 |
| | CYDMS | 62 |
| | SFDMS | 63 |
| | SHDMS | 64 |
| | SWDMS | 65 |
| | SYDMT | 66 |
| | SYDMC | 67 |

| Name | Sequence | SEQ ID NO: |
|---|---|---|
| VH CDR2 | TISDGGGYIYYSDSVKG | 2 |
| | TISDGGAYIYYSDSVKG | 68 |
| | TISDGGPYIYYSDSVKG | 69 |
| | TISDGGGFIYYSDSVKG | 70 |
| | TISDGGGHIYYSDSVKG | 71 |
| | TISDGGGWIYYSDSVKG | 72 |
| | TISDGGGYIYYSDTVKG | 73 |
| | TISDGGGYIYYSDCVKG | 74 |
| | TISDGGGYIYYSDSLKG | 75 |
| | TISDGGGYIYYSDSIKG | 76 |
| | TISDGGGYIYYSDSMKG | 77 |

| Name | Sequence | SEQ ID NO: |
|---|---|---|
| VH CDR3 | EFGKRYALDY | 3 |
| | QFGKRYALDY | 78 |
| | DFGKRYALDY | 79 |
| | NFGKRYALDY | 80 |
| | EYGKRYALDY | 81 |
| | EHGKRYALDY | 82 |
| | EWGKRYALDY | 83 |
| | EFAKRYALDY | 84 |
| | EFPKRYALDY | 85 |
| | EFGRRYALDY | 86 |
| | EFGKKYALDY | 87 |
| | EFGKRFALDY | 88 |
| | EFGKRHALDY | 89 |
| | EFGKRWALDY | 90 |

| Name | Sequence | SEQ ID NO: |
|---|---|---|
| VL CDR1 | KASQDVTPAVA | 4 |
| | KATQDVTPAVA | 91 |
| | KACQDVTPAVA | 92 |

| Name | Sequence | SEQ ID NO: |
|---|---|---|
| VL CDR2 | STSSRYT | 5 |
| | TTSSRYT | 93 |
| | CTSSRYT | 94 |
| | SSSSRYT | 95 |
| | SMSSRYT | 96 |

TABLE 13-continued

VH and VL CDRs and their variants suitable for inclusion in humanized antibodies

| | Sequence | SEQ ID NO: |
|---|---|---|
| | SV̲SSRYT | 97 |
| | STT̲SRYT | 98 |
| | STC̲SRYT | 99 |
| | STST̲RYT | 100 |
| | STSC̲RYT | 101 |
| | STSSK̲YT | 102 |
| | STSSRF̲T | 103 |
| | STSSRH̲T | 104 |
| | STSSRW̲T | 105 |

| Name | Sequence | SEQ ID NO: |
|---|---|---|
| VL CDR3 | QQ̲HYTTPLT | 6 |
| | E̲QHYTTPLT | 106 |
| | D̲QHYTTPLT | 107 |
| | N̲QHYTTPLT | 108 |
| | QE̲HYTTPLT | 109 |
| | QD̲HYTTPLT | 110 |
| | QN̲HYTTPLT | 111 |

Underline: hotspot mutation residues and their substitutes

Example 12: Identification of PD-L1 Epitope

This study was conducted to identify amino acid residues involved in the binding of PD-L1 to the antibodies of the present disclosure.

Figure 16:
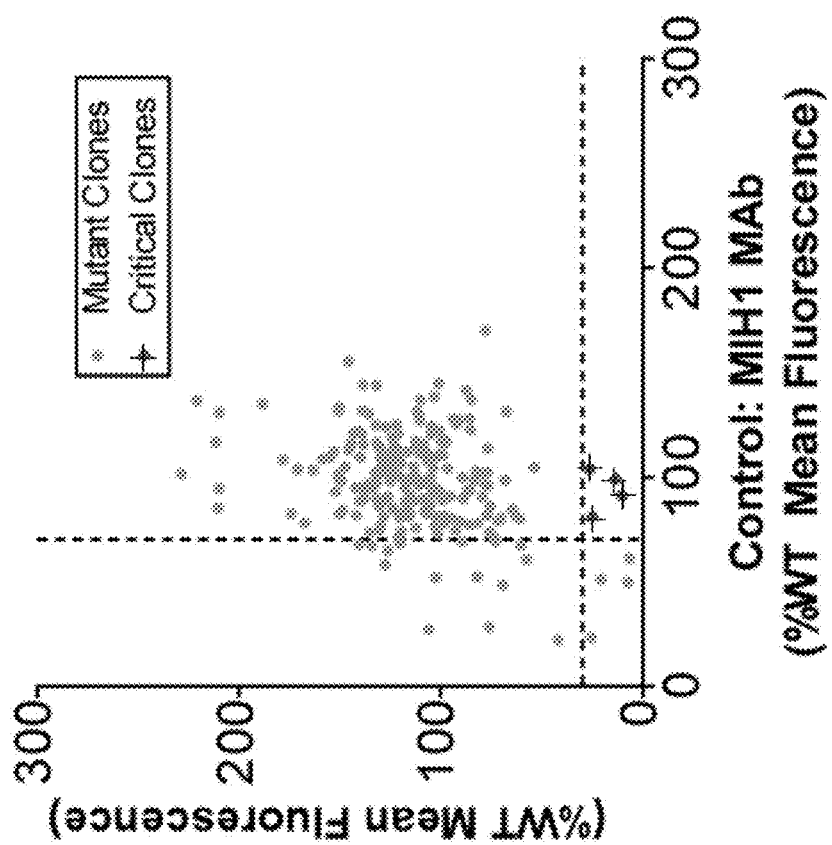
FIG. 16 plots, for each PD-L1 mutant, the mean binding value as a function of expression (control anti-PD-L1 mAb reactivity).

An alanine-scan library of PD-L1 was constructed. Briefly, 217 mutant clones of PD-L1 were generated on Integral Molecular's protein engineering platform. Binding of Hu1210-41 Fab to each variant in the PD-L1 mutation library was determined, in duplicate, by high-throughput flow cytometry. Each raw data point had background fluorescence subtracted and was normalized to reactivity with PD-L1 wild-type (WT). For each PD-L1 variant, the mean binding value was plotted as a function of expression (control anti-PD-L1 mAb reactivity). To identify preliminary critical clones (circles with crosses), thresholds (dashed lines) of >70% WT binding to control MAb and <30% WT reactivity to Hu1210-41 Fab were applied (FIG. 16). Y134, K162, and N183 of PDL1 were identified as required residues for Hu1210-41 binding. The low reactivity of N183A clone with Hu1210-41 Fab suggests that it is the major energetic contributor to Hu1210-41 binding, with lesser contributions by Y134 and K162.

Figure 17:
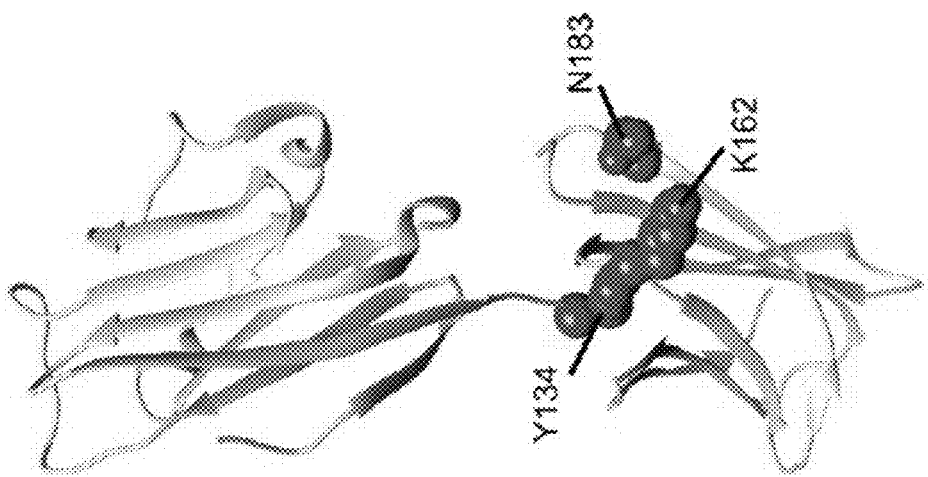
FIG. 17 illustrates the locations of Y134, K162, and N183, the residues (spheres) involved in binding to the anti-PD-L1 Hu1210-41 antibody.

The critical residues (spheres) were identified on a 3D PD-L1 structure (PDB ID#5JDR, Zhang et al., 2017), illustrated in FIG. 17. These residues, Y134, K162, and N183, therefore, constitute an epitope of PD-L1 responsible for binding to antibodies of various embodiments of the present disclosure.

It is interesting to note that Y134, K162, and N183 are all located within the IgC domain of the PD-L1 protein. Both PD-1 and PD-L1's extracellular portions have an IgV domain and an IgC domain. It is commonly known that PD-L1 binds to PD-1 through bindings between their IgV domains. Unlike such conventional antibodies, however, Hu1210-41 binds to the IgC domain, which would have been expected to be ineffective in inhibiting PD-1/PD-L1 binding. This different epitope of Hu1210-41, surprisingly, likely contributes to the excellent activities of Hu1210-41.

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference

---

What is claimed is:

1. An antibody or fragment thereof, wherein the antibody or fragment thereof has specificity to a human Programmed death-ligand 1 (PD-L1) protein and comprises a VH CDR1 comprising the amino acid sequence of SEQ ID NO: 1, a VH CDR2 comprising the amino acid sequence of SEQ ID NO: 2, a VH CDR3 comprising the amino acid sequence of SEQ ID NO: 3, a VL CDR1 comprising the amino acid sequence of SEQ ID NO: 4, a VL CDR2 comprising the amino acid sequence of SEQ ID NO: 5, and a VL CDR3 comprising the amino acid sequence of SEQ ID NO: 6.

2. The antibody or fragment thereof of claim 1, further comprising a heavy chain constant region, a light chain constant region, an Fc region, or the combination thereof.

3. The antibody or fragment thereof of claim 1, wherein the antibody or fragment thereof is a humanized antibody.

4. An antibody or fragment thereof, wherein the antibody or fragment thereof has specificity to a human Programmed death-ligand 1 (PD-L1) protein and comprises a heavy chain variable region comprising an amino acid sequence selected from the group consisting of SEQ ID NO: 7-26 and a light chain variable region comprising an amino acid sequence selected from the group consisting of SEQ ID NO: 27-33.

5. The antibody or fragment thereof of claim 4, comprising a heavy chain variable region comprising the amino acid sequence of SEQ ID NO: 20 and a light chain variable region comprising the amino acid sequence of SEQ ID NO: 28.

6. A composition comprising the antibody or fragment thereof of claim 1 and a pharmaceutically acceptable carrier.

7. An isolated cell comprising one or more polynucleotide encoding the antibody or fragment thereof of claim 1.

8. An isolated antibody or fragment thereof, wherein the antibody or fragment thereof has specificity to a human PD-L1 protein and comprises:
   (a) a VH CDR1 of SEQ ID NO: 1, or a variant of SEQ ID NO: 1 having a single substitution, deletion or insertion at location 1, 2 or 5 of SEQ ID NO: 1;
   (b) a VH CDR2 of SEQ ID NO: 2, or a variant of SEQ ID NO: 2 having a single substitution, deletion or insertion at location 7, 8, 14 or 15 of SEQ ID NO: 2;
   (c) a VH CDR3 of SEQ ID NO: 3, or a variant of SEQ ID NO: 3 having a single substitution, deletion or insertion at location 1, 2, 3, 4, 5 or 6 of SEQ ID NO: 3;
   (d) a VL CDR1 of SEQ ID NO: 4, or a variant of SEQ ID NO: 4 having a single substitution, deletion or insertion at location 3 of SEQ ID NO: 4;
   (e) a VL CDR2 of SEQ ID NO: 5, or a variant of SEQ ID NO: 5 having a single substitution, deletion or insertion at location 1, 2, 3, 4, 5 or 6 of SEQ ID NO: 5 and
   (f) a VL CDR3 of SEQ ID NO: 6, or a variant of SEQ ID NO: 6 having a single substitution, deletion or insertion at location 11 or 2 of SEQ ID NO: 6.

9. The antibody or fragment thereof of claim 8, wherein the variant of SEQ ID NO: 1 is selected from the group consisting of SEQ ID NO: 61-67.

10. The antibody or fragment thereof of claim 8, wherein the variant of SEQ ID NO: 2 is selected from the group consisting of SEQ ID NO: 68-77.

11. The antibody or fragment thereof of claim 8, wherein the variant of SEQ ID NO: 3 is selected from the group consisting of SEQ ID NO: 78-90.

12. The antibody or fragment thereof of claim 8, wherein the variant of SEQ ID NO: 4 is selected from the group consisting of SEQ ID NO: 91-92.

13. The antibody or fragment thereof of claim 8, wherein the variant of SEQ ID NO: 5 is selected from the group consisting of SEQ ID NO: 93-105.

14. The antibody or fragment thereof of claim 8, wherein the variant of SEQ ID NO: 6 is selected from the group consisting of SEQ ID NO: 106-111.

15. An isolated bispecific antibody comprising a fragment of claim 8 and a second antigen-binding fragment having specificity to a molecular on an immune cell.

16. The bispecific antibody of claim 15, wherein the molecule is selected from the group consisting of PD-1, CTLA-4, LAG-3, CD28, CD122, 4-1BB, TIM3, OX-40, OX40L, CD40, CD40L, LIGHT, ICOS, ICOSL, GITR, GITRL, TIGIT, CD27, VISTA, B7H3, B7H4, HEVM, BTLA, KIR, and CD47.

17. The bispecific antibody of claim 15, wherein the fragment and the second fragment each is independently selected from a Fab fragment, a single-chain variable fragment (scFv), or a single-domain antibody.

18. The bispecific antibody of claim 15, further comprising a Fc fragment.

* * * * *